US010736648B2

(12) United States Patent
Denzinger et al.

(10) Patent No.: US 10,736,648 B2
(45) Date of Patent: Aug. 11, 2020

(54) SURGICAL INSTRUMENT WITH REMOVABLE PORTION TO FACILITATE CLEANING

(71) Applicant: Ethicon LLC, Guaynabo, PR (US)

(72) Inventors: Kristen G. Denzinger, Cincinnati, OH (US); Qinlin Gu, Shanghai (CN); Wei Guo, Shanghai (CN); Timothy S. Holland, Cincinnati, OH (US); Patrick J. Minnelli, Harrison, OH (US); Daniel J. Mumaw, Liberty Township, OH (US); Yachuan Yu, Shanghai (CN); Monica L. Zeckel, Zionsville, IN (US)

(73) Assignee: Ethicon LLC, Guaynabo, PR (US)

( * ) Notice: Subject to any disclaimer, the term of this patent is extended or adjusted under 35 U.S.C. 154(b) by 160 days.

(21) Appl. No.: 15/798,902

(22) Filed: Oct. 31, 2017

(65) Prior Publication Data

US 2018/0132884 A1 May 17, 2018

Related U.S. Application Data

(60) Provisional application No. 62/519,482, filed on Jun. 14, 2017, provisional application No. 62/508,720, (Continued)

(51) Int. Cl.

| | |
|---|---|
| ***A61B 17/32*** | (2006.01) |
| ***A61B 17/34*** | (2006.01) |

(Continued)

(52) U.S. Cl.

CPC ...... *A61B 17/2804* (2013.01); *A61B 18/1442* (2013.01); *A61B 18/1206* (2013.01); (Continued)

(58) Field of Classification Search

CPC ........ A61B 17/2804; A61B 17/320068; A61B 2017/320069; A61B 2017/320064; A61B 18/1442

See application file for complete search history.

(56) References Cited

U.S. PATENT DOCUMENTS

| | | | |
|---|---|---|---|
| 5,322,055 | A | 6/1994 | Davison et al. |
| 5,873,873 | A | 2/1999 | Smith et al. |

(Continued)

FOREIGN PATENT DOCUMENTS

| | | |
|---|---|---|
| JP | 2004-033565 A | 2/2004 |
| JP | 2005-176905 A | 7/2005 |

(Continued)

OTHER PUBLICATIONS

U.S. Appl. No. 15/284,819.

(Continued)

*Primary Examiner* — Tuan V Nguyen

(74) *Attorney, Agent, or Firm* — Frost Brown Todd LLC

(57) ABSTRACT

A surgical instrument has an ultrasonic blade that connects to a distal end of an ultrasonic waveguide. A clamp arm assembly is moveable from an opened position for receiving a tissue, toward a closed position for clamping the tissue. A clamp arm actuator connected to the clamp arm assembly directs the clamp arm assembly from the opened position toward the closed position. An outer sheath surrounds at least a portion of the ultrasonic waveguide. The outer sheath includes a cover removably received against a sheath body, and a sheath securement feature able to detachably couple the cover to the sheath body such that the cover can be detached from the sheath body for accessing the ultrasonic waveguide within the outer sheath.

21 Claims, 53 Drawing Sheets

Related U.S. Application Data filed on May 19, 2017, provisional application No. 62/422,698, filed on Nov. 16, 2016.

(51) Int. Cl.

| | |
|---|---|
| ***A61B 17/28*** | (2006.01) |
| ***A61B 18/14*** | (2006.01) |
| *A61B 18/00* | (2006.01) |
| *A61B 90/00* | (2016.01) |
| *A61B 17/00* | (2006.01) |
| *A61B 18/12* | (2006.01) |

(52) U.S. Cl.

CPC ................. *A61B 2017/0046* (2013.01); *A61B 2017/00106* (2013.01); *A61B 2017/00424* (2013.01); *A61B 2017/00477* (2013.01); *A61B 2017/00876* (2013.01); *A61B 2017/2825* (2013.01); *A61B 2017/2845* (2013.01); *A61B 2017/320074* (2017.08); *A61B 2017/320082* (2017.08); *A61B 2017/320084* (2013.01); *A61B 2017/320088* (2013.01); *A61B 2017/320093* (2017.08); *A61B 2017/320094* (2017.08); *A61B 2017/320095* (2017.08); *A61B 2018/0063* (2013.01); *A61B 2018/0094* (2013.01); *A61B 2018/00642* (2013.01); *A61B 2018/00666* (2013.01); *A61B 2018/00672* (2013.01); *A61B 2018/00755* (2013.01); *A61B 2018/00875* (2013.01); *A61B 2018/00916* (2013.01); *A61B 2018/00958* (2013.01); *A61B 2018/00994* (2013.01); *A61B 2090/034* (2016.02); *A61B 2090/065* (2016.02); *A61B 2090/0811* (2016.02); *A61B 2090/0813* (2016.02)

(56) References Cited

U.S. PATENT DOCUMENTS

| | | | |
|---|---|---|---|
| 5,935,144 | A | 8/1999 | Estabrook |
| 5,980,510 | A | 11/1999 | Tsonton et al. |
| 6,129,735 | A | 10/2000 | Okada et al. |
| 6,139,561 | A | 10/2000 | Shibata et al. |
| 6,325,811 | B1 | 12/2001 | Messerly |
| 6,773,444 | B2 | 8/2004 | Messerly |
| 6,783,524 | B2 | 8/2004 | Anderson et al. |
| 7,563,269 | B2 | 7/2009 | Hashiguchi |
| 8,048,074 | B2 | 11/2011 | Masuda |
| 8,461,744 | B2 | 6/2013 | Wiener et al. |
| 8,591,536 | B2 | 11/2013 | Robertson |
| 8,623,027 | B2 | 1/2014 | Price et al. |
| 8,768,435 | B2 | 7/2014 | Andrus et al. |
| 8,905,935 | B2 | 12/2014 | Akagane |
| 8,926,610 | B2 | 1/2015 | Hafner et al. |
| 8,986,302 | B2 | 3/2015 | Aldridge et al. |
| 9,023,071 | B2 | 5/2015 | Miller et al. |
| 9,050,120 | B2 | 6/2015 | Swarup et al. |
| 9,072,523 | B2 | 7/2015 | Houser et al. |
| 9,084,878 | B2 | 7/2015 | Kawaguchi et al. |
| 9,095,367 | B2 | 8/2015 | Olsen et al. |
| 9,326,787 | B2 | 5/2016 | Sanai et al. |
| 9,351,753 | B2 | 5/2016 | Balanev et al. |
| 9,381,058 | B2 | 7/2016 | Houser et al. |
| 9,393,037 | B2 | 7/2016 | Olson et al. |
| 9,510,891 | B2 | 12/2016 | Allen, IV et al. |
| 9,566,084 | B2 | 2/2017 | Katsumata |
| 9,572,622 | B2 | 2/2017 | Shelton, IV et al. |
| 9,901,360 | B2 | 2/2018 | Neurohr et al. |
| 9,949,785 | B2 | 4/2018 | Price et al. |
| 10,543,383 | B2 | 1/2020 | Kase |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2012/0116265 | A1 | 5/2012 | Houser et al. |
| 2013/0303949 | A1* | 11/2013 | Kawaguchi .......... A61B 17/282 601/2 |
| 2014/0135804 | A1 | 5/2014 | Weisenburgh, II et al. |
| 2014/0221994 | A1 | 8/2014 | Reschke |
| 2015/0080924 | A1 | 3/2015 | Stulen et al. |
| 2015/0080925 | A1 | 3/2015 | Schulte et al. |
| 2015/0148835 | A1* | 5/2015 | Faller ............. A61B 17/320092 606/169 |
| 2015/0265305 | A1 | 9/2015 | Stulen et al. |
| 2016/0030076 | A1 | 2/2016 | Faller et al. |
| 2016/0175001 | A1 | 6/2016 | Hibner et al. |
| 2017/0105754 | A1 | 4/2017 | Boudreaux et al. |
| 2017/0105755 | A1 | 4/2017 | Boudreaux et al. |
| 2017/0105788 | A1 | 4/2017 | Boudreaux |
| 2018/0132883 | A1 | 5/2018 | Asher et al. |
| 2018/0132884 | A1 | 5/2018 | Denzinger et al. |
| 2018/0132887 | A1 | 5/2018 | Asher et al. |
| 2018/0132888 | A1 | 5/2018 | Asher et al. |
| 2018/0132926 | A1 | 5/2018 | Asher et al. |

FOREIGN PATENT DOCUMENTS

| | | | |
|---|---|---|---|
| JP | 2005-253674 | A | 9/2005 |
| WO | WO 2011/008672 | A2 | 1/2011 |
| WO | WO 2016/015233 | A1 | 2/2016 |

OTHER PUBLICATIONS

U.S. Appl. No. 15/284,837.
U.S. Appl. No. 15/284,855.
U.S. Appl. No. 15/798,680.
U.S. Appl. No. 15/798,703.
U.S. Appl. No. 15/798,720; and.
U.S. Appl. No. 15/798,835.
U.S. Appl. No. 15/798,680, filed Oct. 31, 2017.
U.S. Appl. No. 15/798,703, filed Oct. 31, 2017.
U.S. Appl. No. 15/798,720, filed Oct. 31, 2017.
U.S. Appl. No. 15/798,835, filed Oct. 31, 2017.
U.S. Appl. No. 61/410,603, filed Nov. 5, 2010.
U.S. Appl. No. 62/363,411, filed Jul. 18, 2016.
U.S. Appl. No. 62/422,698, filed Nov. 16, 2016.
U.S. Appl. No. 62/508,720, filed May 19, 2017.
U.S. Appl. No. 62/519,482, filed Jun. 14, 2017.
International Search Report and Written Opinion dated Jan. 30, 2018 for PCT/US2017/061995, 11 pgs.
International Search Report and Written Opinion dated Jun. 20, 2018 for PCT/US2017/062010, 16 pgs.
International Search Report and Written Opinion dated Apr. 13, 2018 for PCT/US2017/062016, 17 pgs.
International Search Report and Written Opinion dated Feb. 1, 2018 for PCT/US2017/062023, 13 pgs.
International Search Report and Written Opinion dated Apr. 3, 2018 for PCT/US2017/062025, 18 pgs.

* cited by examiner

SURGICAL INSTRUMENT WITH REMOVABLE PORTION TO FACILITATE CLEANING

PRIORITY

This application claims priority to: (1) U.S. Provisional Patent Application Ser. No. 62/422,698, filed Nov. 16, 2016, entitled "Ultrasonic Surgical Shears with Contained Compound Lever Clamp Arm Actuator," the disclosure of which is incorporated by reference herein; (2) U.S. Provisional Patent Application Ser. No. 62/508,720, filed May 19, 2017, entitled "Ultrasonic and Electrosurgical Instrument with Replaceable End Effector Features," the disclosure of which is incorporated by reference herein; and (3) U.S. Provisional Patent Application Ser. No. 62/519,482, filed Jun. 14, 2017, entitled "Ultrasonic and Electrosurgical Instrument with Removable Features," the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,023,071, entitled "Ultrasonic Device for Fingertip Control," issued May 5, 2015, the disclosure of which is incorporated by reference herein; and U.S. Pat. No. 8,461,744, entitled "Rotating Transducer Mount for Ultrasonic Surgical Instruments," issued Jun. 11, 2013, the disclosure of which is incorporated by reference herein; and U.S. Pat. No. 8,591,536, entitled "Ultrasonic Surgical Instrument Blades," issued Nov. 26, 2013, the disclosure of which is incorporated by reference herein.

Some of ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, entitled "Surgical Instruments with Articulating Shafts," issued Jul. 19, 2016, the disclosure of which is incorporated by reference herein; and U.S. Pat. No. 9,095,367, entitled "Flexible Harmonic Waveguides/Blades for Surgical Instruments," issued Aug. 4, 2015 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1A:
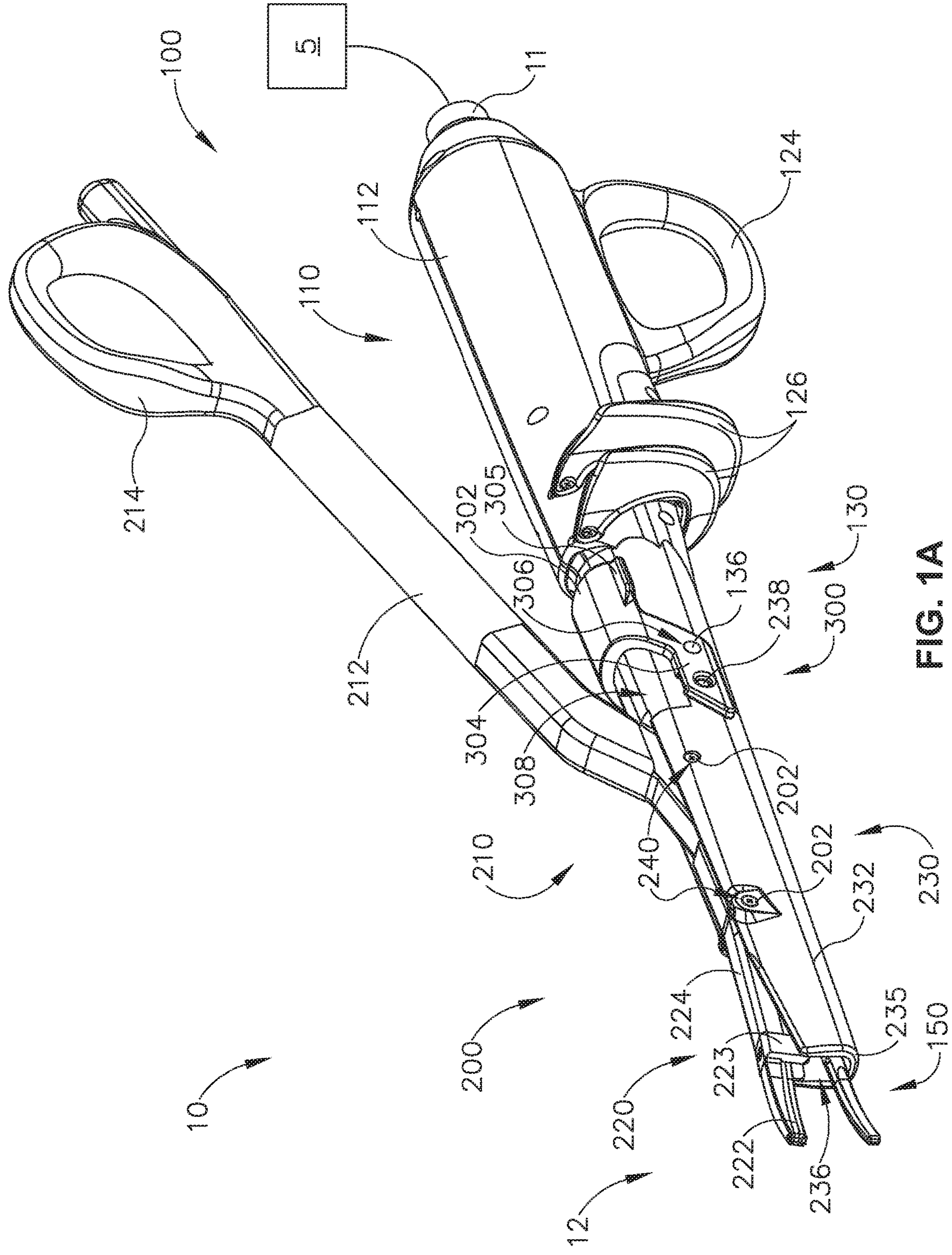
FIG. 1A depicts a perspective view of a first exemplary surgical instrument, with an end effector of the instrument in an open configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," and "top" are relative terms to provide additional clarity to the figure descriptions provided below. The terms "upper," "lower," "lateral," "transverse," "bottom," and "top" are thus not intended to unnecessarily limit the invention described herein.

I. First Exemplary Ultrasonic Surgical Instrument for Open Surgical Procedures FIGS. 1A-2 and FIGS. 13A-13C illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pat. Nos. 8,623,027; 9,023,071; 8,461,744; 9,381,058; U.S. Pub. No. 2012/0116265; U.S. Pat. Nos. 9,393,037; 9,095,367; U.S. Pat. App. No. 61/410,603; and/or U.S. Pub. No. 2015/0080924. The disclosures of each of the foregoing patents, publications, and applications are incorporated by reference herein. In addition, or in the alternative, at least part of instrument (10) may be constructed and operable in accordance with at least some of the teachings of U.S. Pub. No. 2017/0105755, entitled "Surgical Instrument with Dual Mode End Effector and Compound Lever with Detents," published on Apr. 20, 2017, the disclosure of which is incorporated by reference herein; and/or U.S. Pat. App. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Figure 1B:
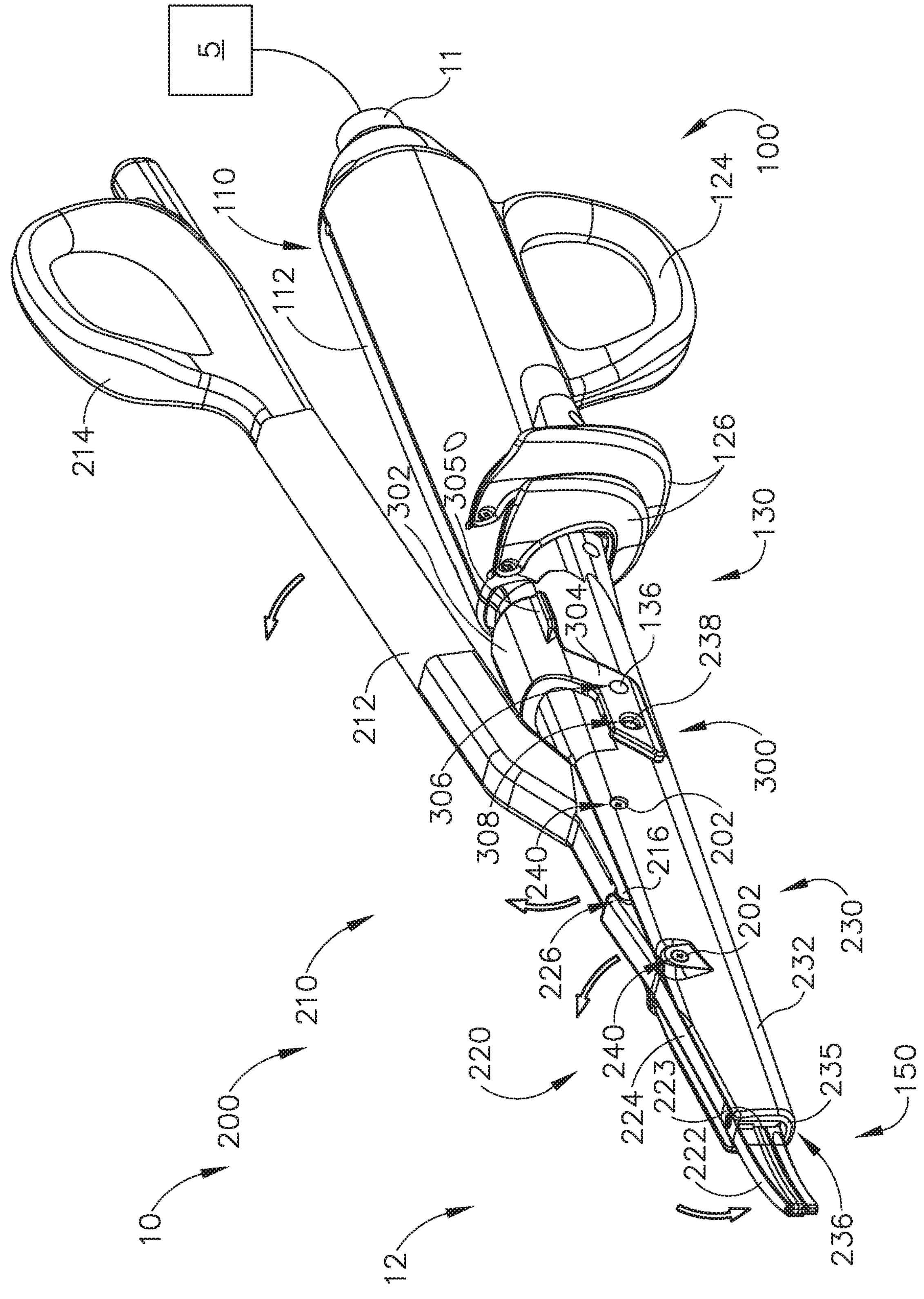
FIG. 1B depicts a perspective view of the instrument of FIG. 1A, with the end effector in a closed configuration.
Figure 2:
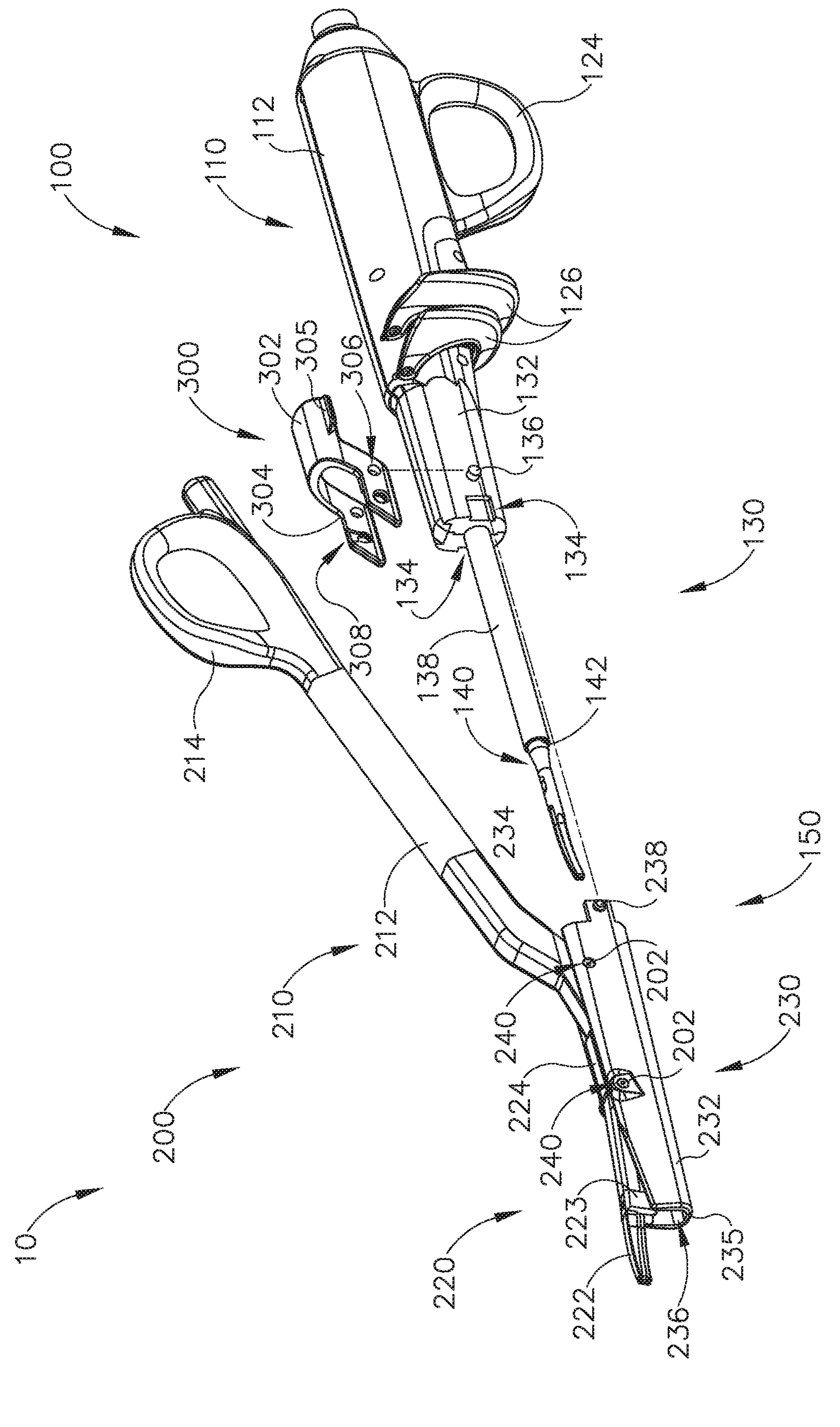
FIG. 2 depicts an exploded perspective view of the instrument of FIG. 1A.
Figure 3:
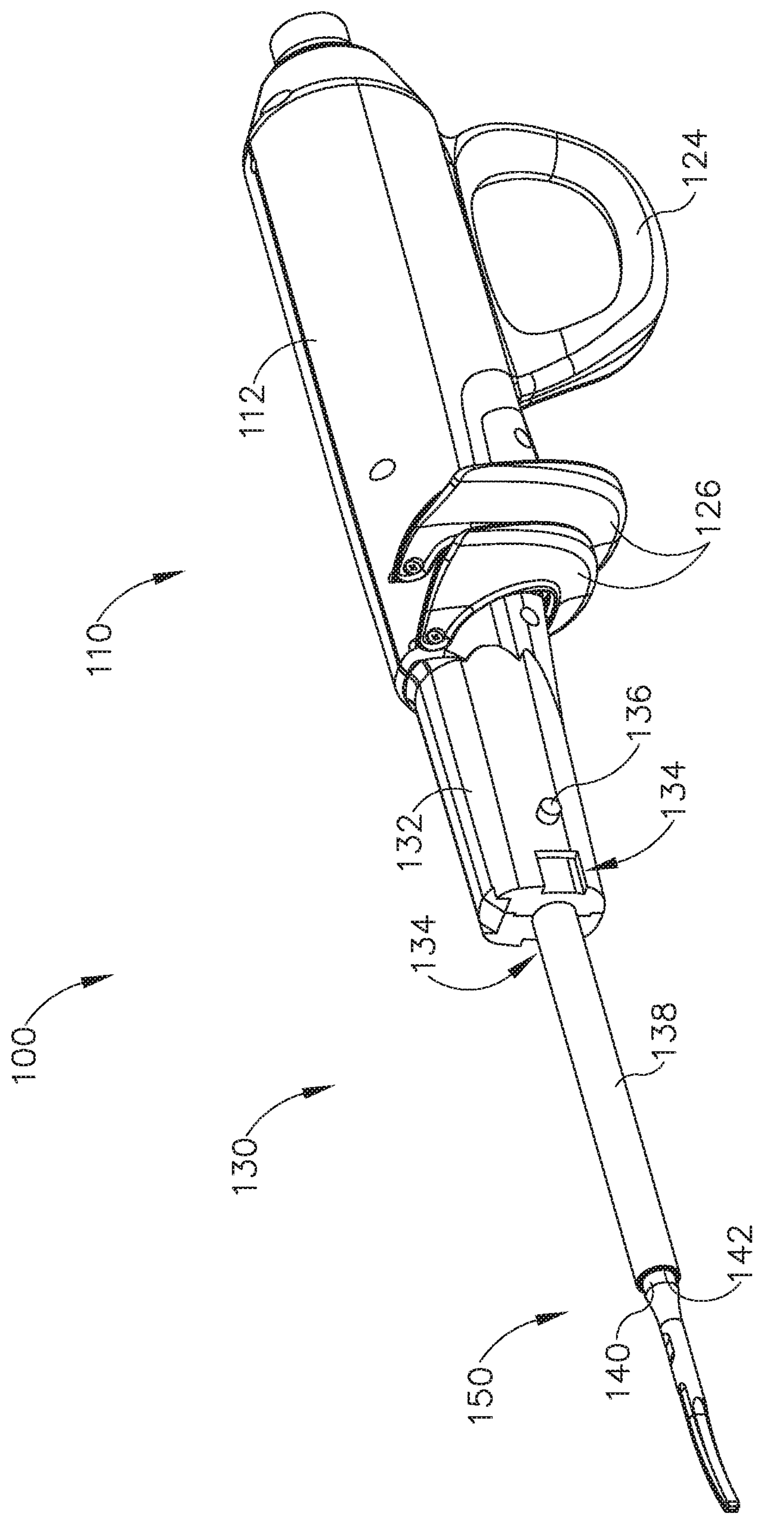
FIG. 3 depicts a perspective view of a first modular assembly of the instrument of FIG. 1A.

Instrument (10) in the present example includes a first modular assembly (100), a second modular assembly (200), and a coupling member (300). As will be described in greater detail below, coupling member (300) may selectively attach first modular assembly (100) with second modular assembly (200) in order to form instrument (10) with an end effector (12). As best seen in FIGS. 1A-1B, end effector (12) comprises an ultrasonic blade (150) and a clamp pad (222) of a clamp pad assembly (220).

Figure 16A:
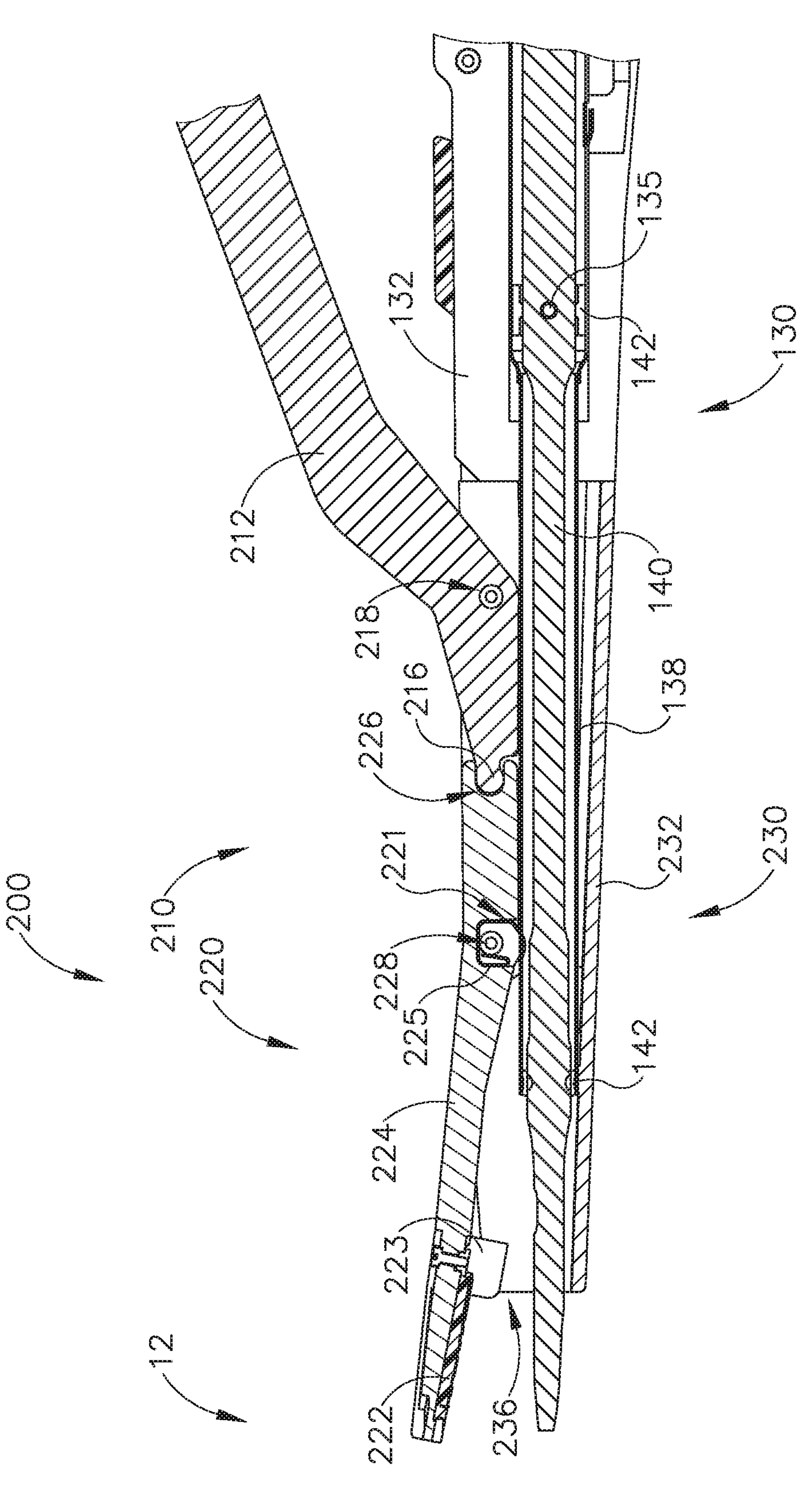
FIG. 16A depicts a cross-sectional side view of the second modular assembly of FIG. 8 coupled with the shaft assembly of FIG. 5, where the end effector is in an open configuration.
Figure 16B:
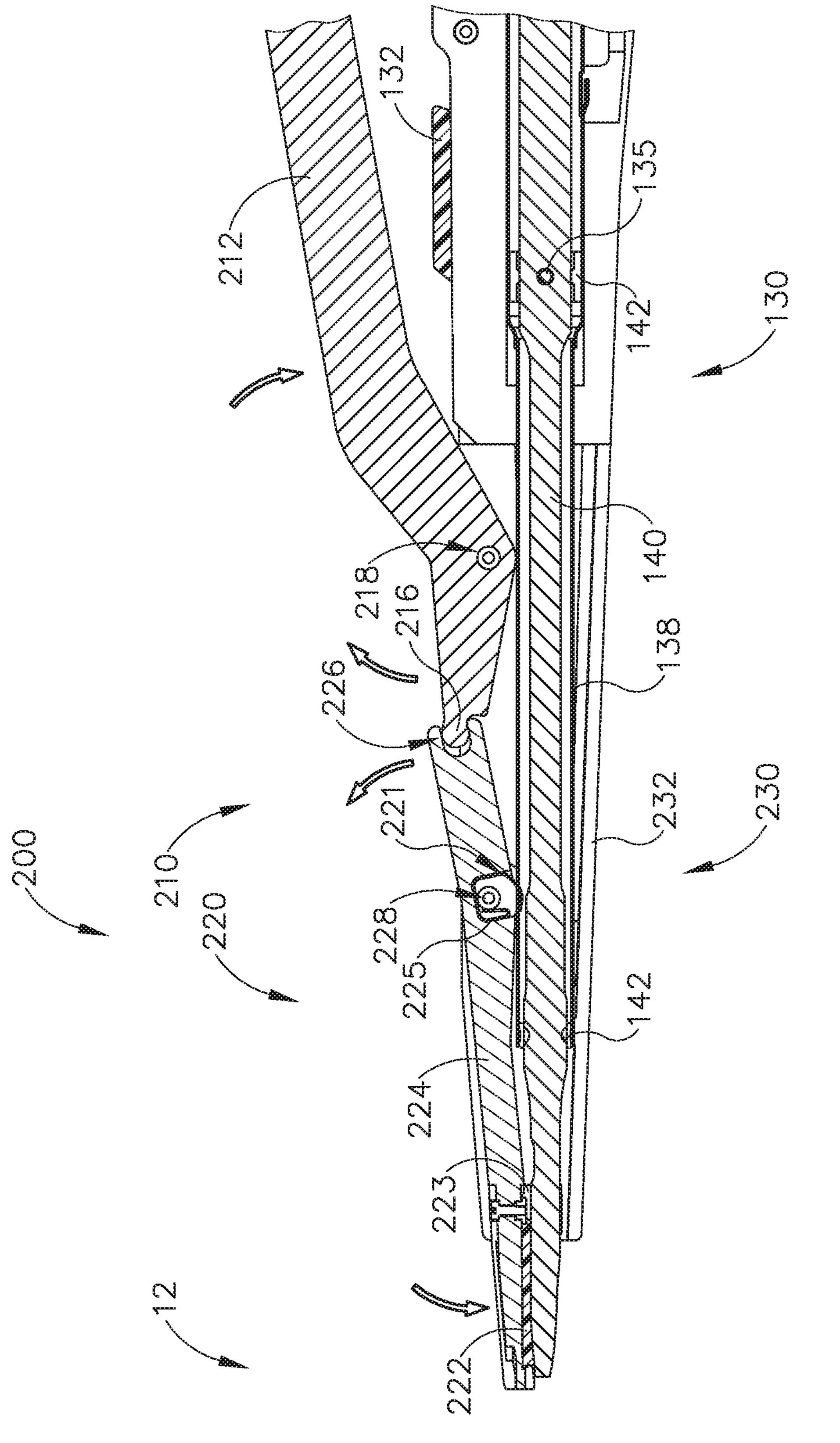
FIG. 16B depicts a cross-sectional side view of the second modular assembly of FIG. 8 coupled with the shaft assembly of FIG. 5, where the end effector is in a closed configuration.

Additionally, as will be described in greater detail below, selected portions of second modular assembly (200) may actuate relative to first modular assembly (100), when properly attached with each other, in order to actuate end effector (12) from an open configuration (FIGS. 1A and 16A), to a closed configuration (FIGS. 1B and 16B). The ability to selectively attach and detach second modular assembly (200) with first modular assembly (100) may provide additional benefits of reusability of either modular assembly (100, 200). For instance, different kinds of first modular assemblies (100) may be used with second modular assembly (200) to provide different kinds of surgical instruments. Similarly, different kinds of second modular assemblies (200) may be used with first modular assembly (100) to provide different kinds of surgical instruments. Additionally, moving components of second modular assembly (200) may be housed within static components of second modular assembly (200), which may provide additional advantages, some of which are described below while others will be apparent to one having ordinary skill in the art in view of the teachings herein.

First modular assembly (100) includes a handle assembly (110), a shaft assembly (130) extending distally from handle assembly (110), and an ultrasonic blade (150) extending distally from shaft assembly (130). Handle assembly (110) includes a body (112), a finger grip ring (124), a pair of buttons (126) distal to finger grip ring (124), and an ultrasonic transducer assembly (30) housed within body (112).

Shaft assembly (130) includes a proximal outer sheath (132) extending distally from body (112), a tube (138) extending distally from proximal outer sheath (132), and a waveguide (140) extending within and through both proximal outer sheath (132) and tube (138). Proximal outer sheath (132) includes a pair of protrusions (136). Additionally, proximal outer sheath (132) defines a pair of recesses (134). As will be described in greater detail below, recesses (134) are dimensioned to mate with a portion of distal outer sheath (230) while protrusions (136) are configured to pivotally couple proximal outer sheath (132) with coupling member (300). Both recesses (134) and protrusions (136) may help couple first modular assembly (100) with coupling member (300).

Proximal outer sheath (132) may be fixed relative to body (112), while tube (138) may be fixed relative to proximal outer sheath (132). As will be described in greater detail below, waveguide (140) may attach to transducer assembly (30) and be supported by portions proximal outer sheath (132) and tube (138). Ultrasonic blade (150) may be unitarily connected to waveguide (140), and also extend distally from waveguide (140). As will be described in greater detail below, waveguide (140) is operable to connect to ultrasonic transducer assembly (30) in order to provide acoustic communication between ultrasonic blade (150) and transducer assembly (30).

Figure 4:
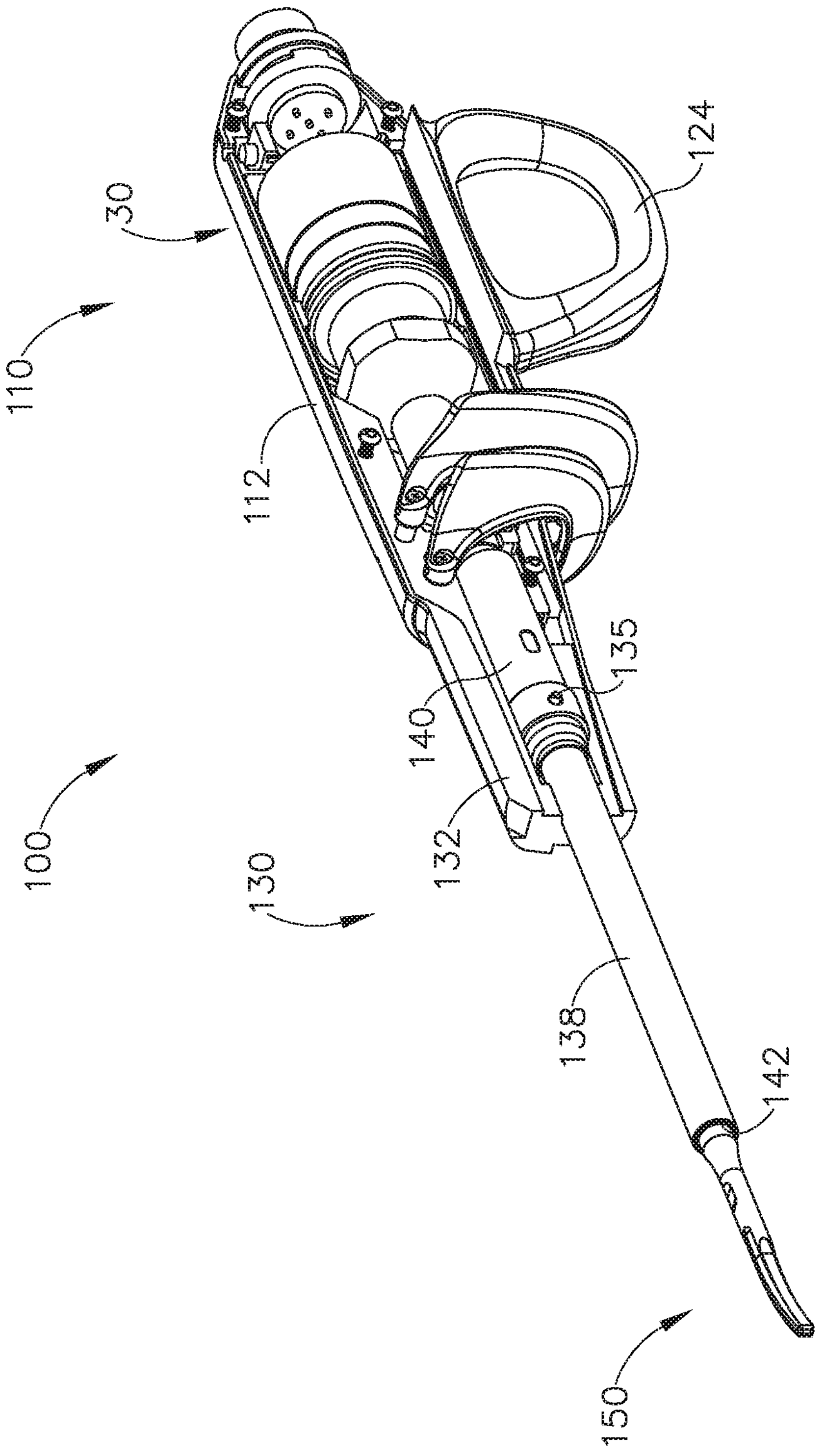
FIG. 4 depicts a perspective view of the first modular assembly of FIG. 3, with selected portions purposefully omitted for clarity.
Figure 5:
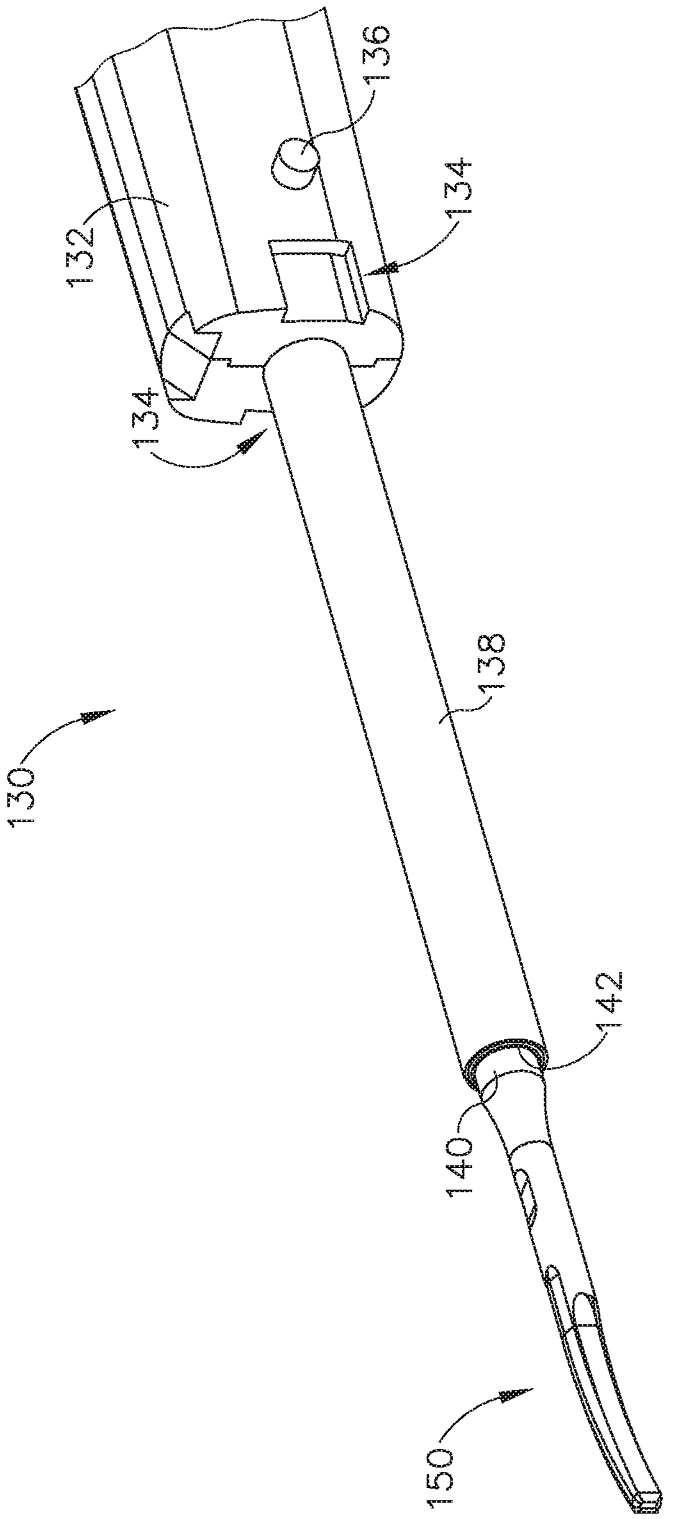
FIG. 5 depicts a perspective view of a shaft assembly and a blade assembly of the first modular assembly of FIG. 3.

Referring to FIG. 4, ultrasonic transducer assembly (30) is housed within body (112) of handle assembly (110). As seen in FIGS. 1A-1B, transducer assembly (30) is coupled with a generator (5) via a plug (11). Transducer assembly (30) receives electrical power from generator (5) and converts that power into ultrasonic vibrations through piezoelectric principles. Generator (5) may include a power source and control module that is configured to provide a power profile to transducer assembly (30) that is particularly suited for the generation of ultrasonic vibrations through transducer assembly (30). Generator (5) may also be configured to provide a power profile that enables end effector (12) to apply RF electrosurgical energy to tissue.

By way of example only, generator (5) may comprise a GEN 300 sold by Ethicon Endo-Surgery, Inc. of Cincinnati, Ohio. In addition or in the alternative, generator (not shown) may be constructed in accordance with at least some of the teachings of U.S. Pat. No. 8,986,302, entitled “Surgical Generator for Ultrasonic and Electrosurgical Devices,” published Apr. 14, 2011, the disclosure of which is incorporated by reference herein. It should also be understood that at least some of the functionality of generator (5) may be integrated into handle assembly (110), and that handle assembly (110) may even include a battery or other on-board power source such that plug (11) is omitted. Still other suitable forms that generator (5) may take, as well as various features and operabilities that generator (5) may provide, will be apparent to those of ordinary skill in the art in view of the teachings herein.

Ultrasonic vibrations that are generated by transducer assembly (30) are communicated along acoustic waveguide (140) when properly coupled. Waveguide (140) is mechanically and acoustically coupled with transducer assembly (30). Waveguide (140) extends through shaft assembly (130) to reach ultrasonic blade (150). Waveguide (140) may be secured to proximal outer sheath (132) and/or body (112) via a pin (135) extending through waveguide (140) and proximal outer sheath (132). Pin (135) may help ensure waveguide (140) remains longitudinally and rotationally fixed relative to the rest of shaft assembly (130) when waveguide (140) is in a deactivated state (i.e. not vibrating ultrasonically).

Additionally, waveguide (140) may be supported by tube (138) via seals (142) located between an interior of tube (138) and an exterior of waveguide (140). Seals (142) may also prevent unwanted matter and fluid from entering portions of tube (138) housing waveguide (140). Pin (135) and seals (142) are located at positions along the length of waveguide (140) corresponding to nodes associated with resonant ultrasonic vibrations communicated through waveguide (140). Therefore, contact between waveguide (140) and pin (135), as well as contact between waveguide (140) and seals (142) may not affect ultrasonic vibrations communicated through waveguide (154).

When ultrasonic blade (150) is in an activated state (i.e., vibrating ultrasonically), ultrasonic blade (150) is operable to effectively cut through and seal tissue, particularly when the tissue is being clamped between clamp pad (222) and ultrasonic blade (150). It should be understood that waveguide (140) may be configured to amplify mechanical vibrations transmitted through waveguide (140). Furthermore, waveguide (140) may include features operable to control the gain of the longitudinal vibrations along waveguide (140) and/or features to tune waveguide (140) to the resonant frequency of the system.

In the present example, the distal end of ultrasonic blade (150) is located at a position corresponding to an anti-node associated with resonant ultrasonic vibrations communicated through waveguide (140), in order to tune the acoustic assembly to a preferred resonant frequency $f_o$ when the acoustic assembly is not loaded by tissue. When transducer assembly (30) is energized, the distal end of ultrasonic blade (150) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through the waveguide to (140) reach ultrasonic blade (150), thereby providing oscillation of ultrasonic blade (150) at the resonant ultrasonic frequency. Thus, when tissue is secured between ultrasonic blade (150) and clamp pad (222), the ultrasonic oscillation of ultrasonic blade (150) may simultaneously sever the tissue and denature the proteins in adjacent tissue cells, thereby providing a coagulative effect with relatively little thermal spread.

In some versions, an electrical current may also be provided through ultrasonic blade (150) and/or clamp pad (222) to also seal the tissue. It should therefore be understood that instrument (10) may also be configured to provide radiofrequency (RF) energy to a surgical site via end effector (12). By way of example only, an operator may rely mainly on the use of ultrasonic energy from blade (150) to sever tissue that is captured between ultrasonic blade (150) and clamp pad (222). The operator may further rely on the use of RF energy from end effector (12) to seal the severed tissue. Of course, it will be understood that the ultrasonic energy from blade (150) may seal tissue to some degree, such that the RF energy from end effector (12) may supplement the sealing that would already be provided from the ultrasonic energy. It will also be understood that there may be instances where the operator may wish to simply use end effector (12) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (126) to selectively activate transducer assembly (30) to thereby activate ultrasonic blade (150). In the present example, two buttons (126) are provided. In some versions, one button (126) is provided for activating ultrasonic blade (150) at a first power profile (e.g., a first frequency and/or first amplitude) and another button (126) is provided for activating ultrasonic blade (150) at a second power profile (e.g., a second frequency and/or second amplitude). In some other versions, one button (126) is provided for activating ultrasonic blade (150) with ultrasonic energy, and the other button (126) is provided for activating end effector (12) with RF energy. In some other versions, one button (126) is operable to activate ultrasonic blade (150) with ultrasonic energy while simultaneously activating end effector (12) with RF energy; while the other button (126) is only operable to activate ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while still activating ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while ceasing activation of ultrasonic blade (150) with ultrasonic energy. In some other versions, at least one button (126) is operable to initially activate end effector (12) with RF energy, then based on one or more other conditions (e.g., time, measured impedance, etc.) while button (126) remains activated, eventually activating ultrasonic blade (150) with ultrasonic energy while ceasing activation of end effector (12) with RF energy.

It should be understood that any other suitable number of buttons and/or otherwise selectable power levels and/or power modalities may be provided. For instance, a foot pedal may be provided to selectively activate transducer assembly (30).

Buttons (126) of the present example are positioned such that an operator may readily fully operate instrument (10) with a single hand. For instance, when first and second modular assemblies (100, 200) are coupled, the operator may position their thumb in thumb grip ring (214), position their ring finger in finger grip ring (124), position their middle finger about body (112), and manipulate buttons (126) using their index finger. Of course, any other suitable techniques may be used to grip and operate instrument (10); and buttons (126) may be located at any other suitable positions.

Figure 7:
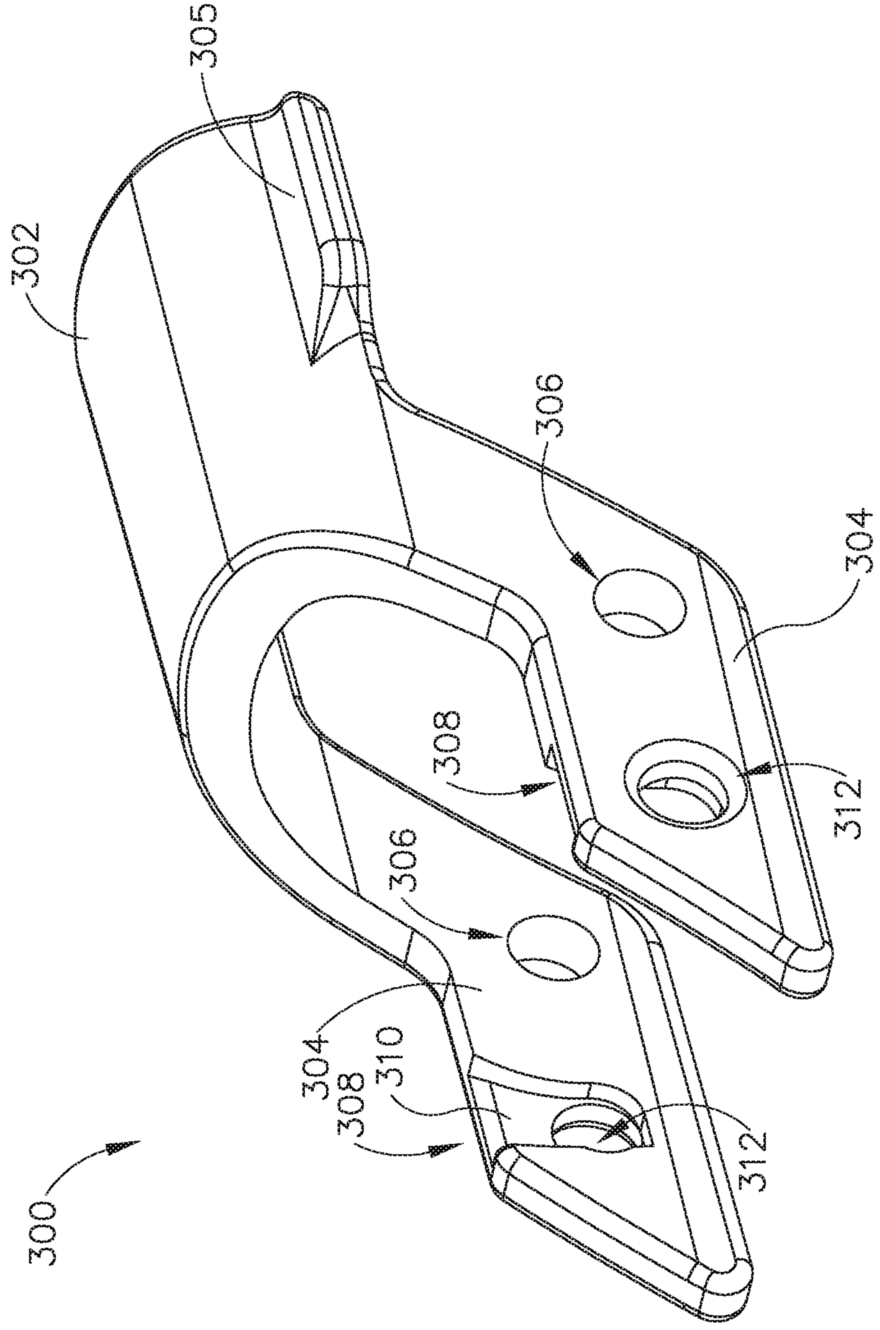
FIG. 7 depicts a perspective view of a coupling member of the instrument of FIG. 1A.
Figure 8:
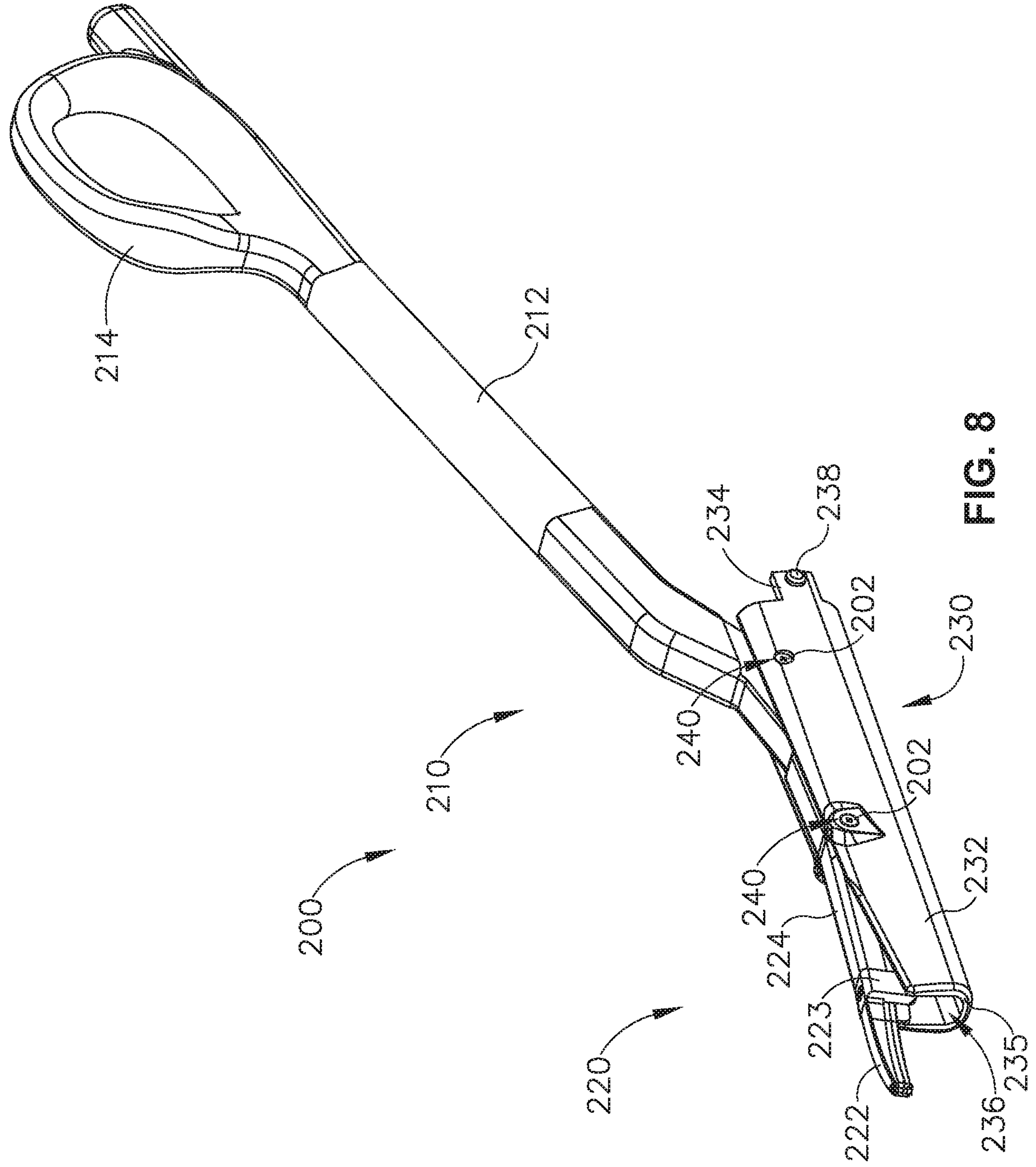
FIG. 8 depicts a perspective view of a second modular assembly of the instrument of FIG. 1A.
Figure 9:
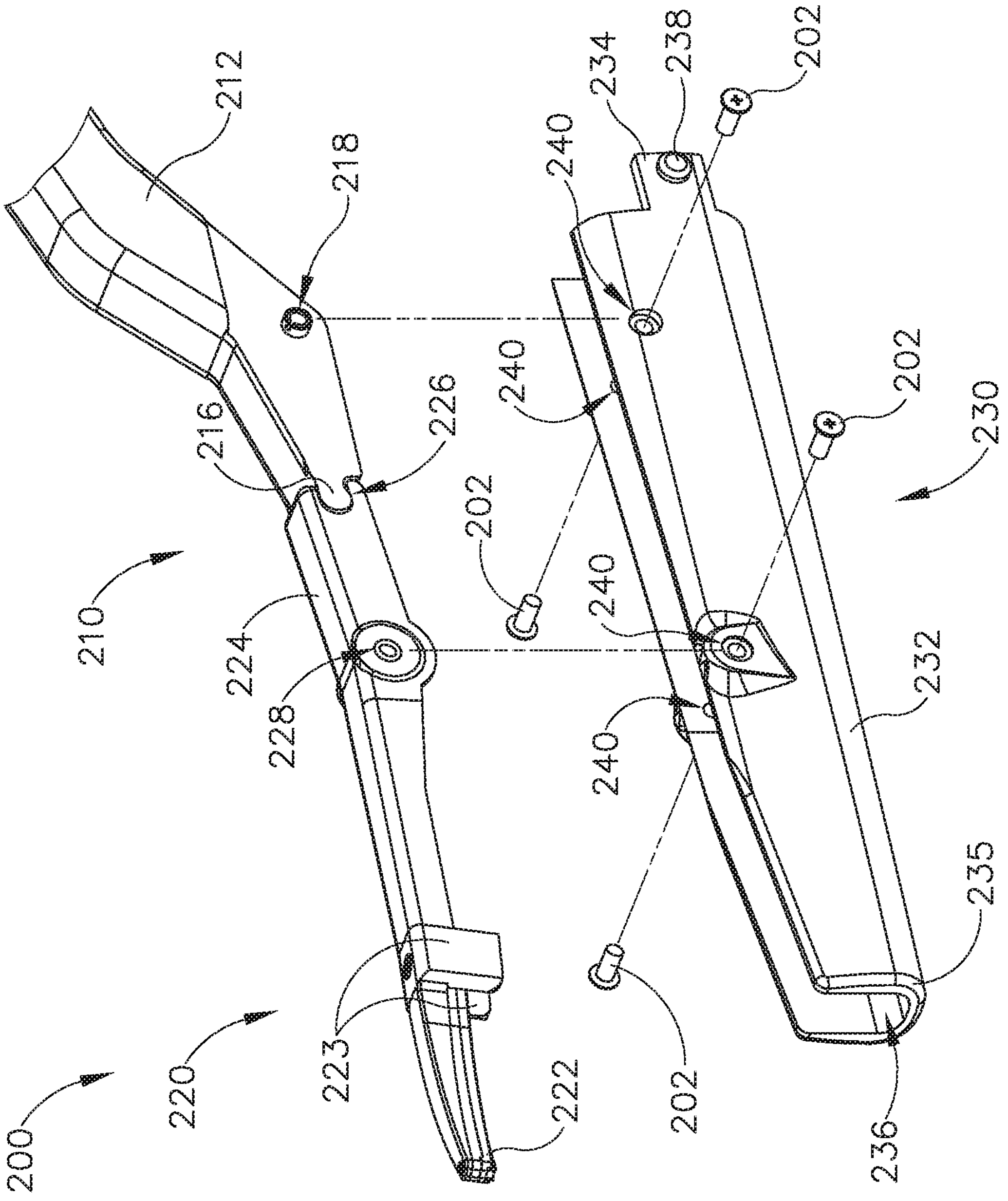
FIG. 9 depicts an exploded perspective view of the second modular assembly of FIG. 8.
Figure 10:
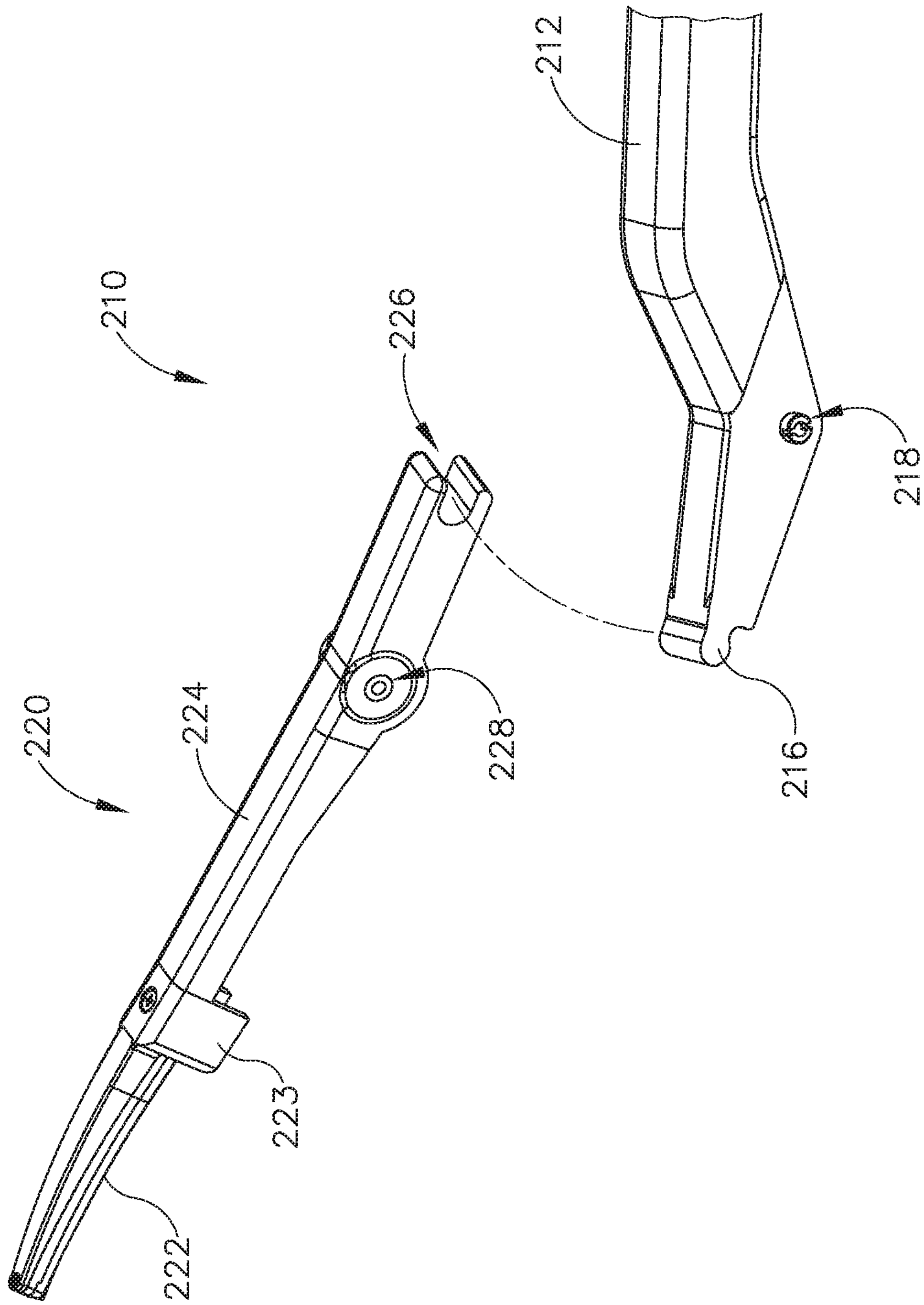
FIG. 10 depicts an exploded perspective view of a clamp arm assembly and a clamp pad assembly of the second modular assembly of FIG. 8.
Figure 11:
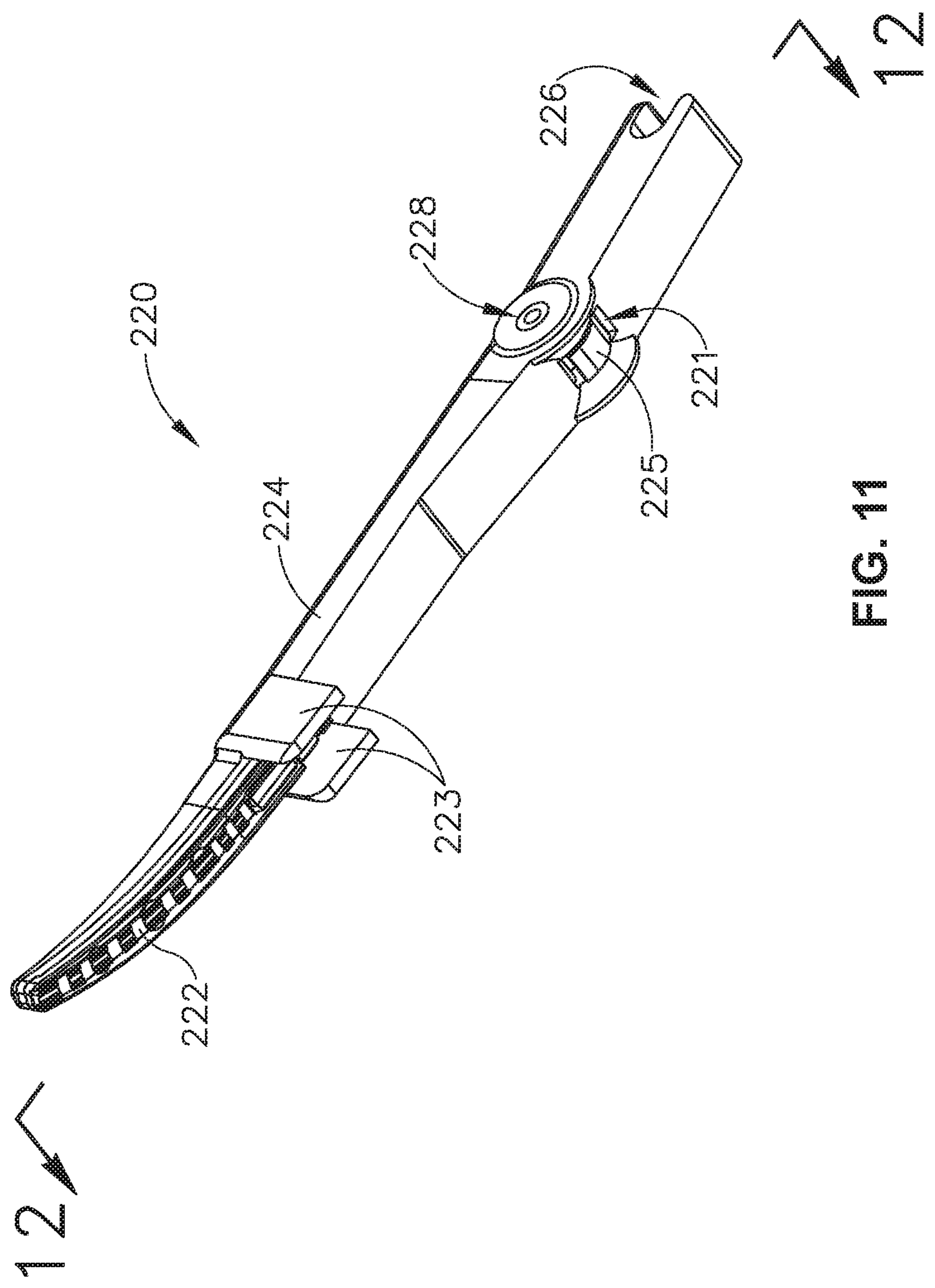
FIG. 11 depicts a perspective view of the clamp arm assembly of FIG. 10.
Figure 12:
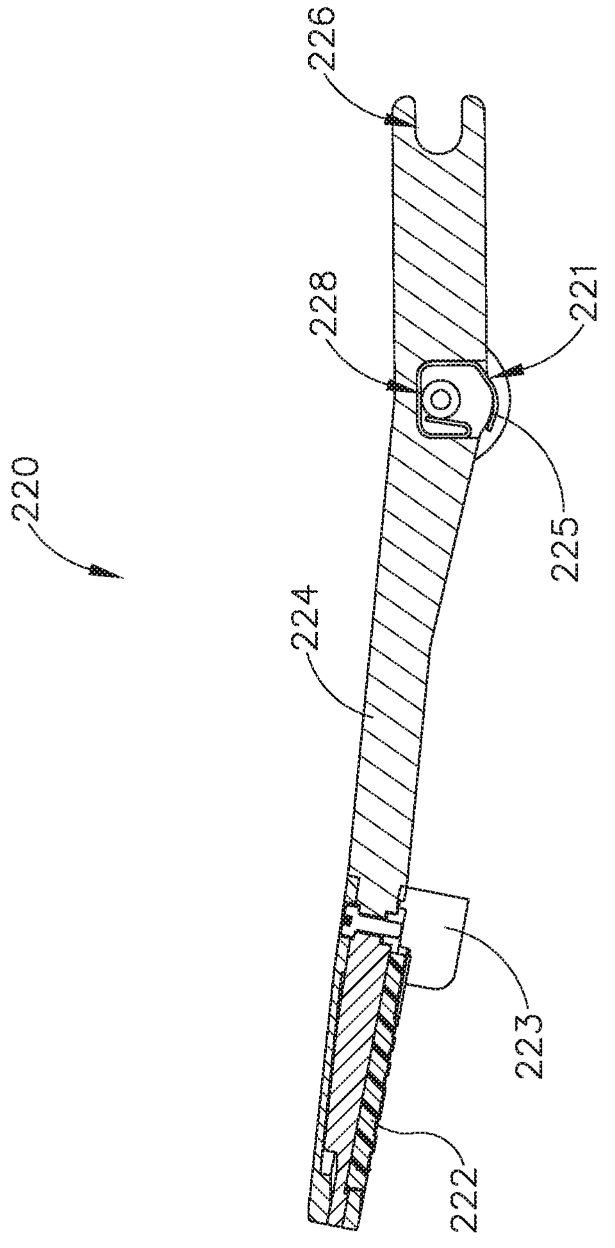
FIG. 12 depicts a cross-sectional side view of the clamp arm assembly of FIG. 10, taken along line 12-12 of FIG. 11.

As mentioned above, and as will be described below, coupling member (300) is configured to selectively couple first modular assembly (100) with second modular assembly (200). As best seen in FIG. 7, coupling member (300) comprises a body (302), a pair of resilient arms (304) extending from body (302), and a pair of grips (305) extending from body (302). Resilient arms (304) each define a respective pivot bore (306) and locking assembly (308). Resilient arms (304) are spaced apart from each other in order to receive proximal outer sheath (132) and to snap-fit pivot bores (306) with respective protrusions (136). Therefore, as shown between FIGS. 13B-13C and 14B-14C, coupling member (300) is configured to pivotally connect with proximal outer sheath (132) via pivot bores (306) and protrusions (136). While in the current example, coupling member (300) and proximal outer sheath (132) are pivotally coupled via snap-fitting, any other type of suitable connection may be used as would be apparent to one having ordinary skill in the art in view of the teachings herein. For example, protrusions (136) may be extendable relative to proximal outer sheath (132) in order to pivotally couple with pivot bore (306) of coupling member (300). Grips (305) may be positioned on body (302) such that an operator may easily rotate coupling member (300) relative to outer sheath (132) via grips (305).

Each locking assembly (308) includes an interior contact wall (310) facing toward each other and a coupling recess (312). As will be described in greater detail below, locking assembly (308) is configured to rotate about pivot bore (306) and protrusions (136) in order to selectively couple with portions of second modular assembly (200).

While coupling member (300) in the current example is used to connect first modular assembly (100) with second modular assembly (200), it should be understood that coupling member (300) may be incorporated into any suitable type of modular assembly that would be apparent to one having ordinary skill in the art in view of the teachings herein. For example, coupling assembly (300) may be modified to couple different modular clamp arm assemblies with first modular assembly (100) where the different modular clamp arm assemblies include clamp arm assemblies such as those taught in U.S. Pub. No. 2017/0105788, entitled "Surgical Instrument with Dual Mode End Effector and Modular Clamp Arm Assembly," published on Apr. 20, 2017, the disclosure of which is incorporated by reference herein. Thus, one modular clamp arm assembly that may be coupled with first modular assembly (100) may provide pivotal motion of a clamp arm at one side of ultrasonic blade (150) while the other modular clamp arm assembly that may be coupled with first modular assembly (100) may provide pivotal motion of a clamp arm at the other side of ultrasonic blade (150). Other suitable kinds of clamp arm assemblies that may be used to provide different kinds of second modular assemblies (200) will be apparent to those of ordinary skill in the art in view of the teachings herein.

Second modular assembly (200) includes a clamp arm assembly (210), a clamp pad assembly (220), and a distal outer sheath (230). As will be described in greater detail below, distal outer sheath (230) is configured to couple with both coupling member (300) and proximal outer sheath (132) in order to selectively couple first modular assembly (100) with second modular assembly (200). It other words, when properly coupled, proximal outer sheath (132) and distal outer sheath (230) may be fixed relative to one another. As will also be described in greater detail below, clamp arm assembly (210) and clamp pad assembly (220) are both pivotally coupled with distal outer sheath (230). Additionally, clamp arm assembly (210) and clamp pad assembly (220) are dimensioned to mesh with each other such that rotation of one assembly (210, 220) relative to distal outer sheath (230) causes rotation of the other assembly (210, 220) relative to distal outer sheath (230). In other words, clamp arm assembly (210) and clamp pad assembly (220) are capable of rotating each other relative to distal outer sheath (230).

Distal outer sheath (230) includes a U-shaped body (232) extending from a distal face (235) and terminating in a pair of proximally presented projections (234). Proximally presented projections (234) each include a lateral protrusion (238) extending away from U-shaped body (232). U-shaped body (232) defines a longitudinal pathway (236) and a plurality of bores (240). U-shaped body (232) and longitudinal pathway (236) are dimensioned to receive tube (138) and to rotationally house a portion of clamp arm assembly (210) and clamp pad assembly (220). In particular, as best shown between FIGS. 13A-13B, U-shaped body (232) may be inserted over ultrasonic blade (150) and tube (138) such that tube (138) will rest under clamp arm assembly (210) and clamp pad assembly (220). Tube (138) may protect waveguide (140) such that clamp arm assembly (210) and clamp pad assembly (220) do not contact adjacent portions of waveguide (140).

Figure 13A:
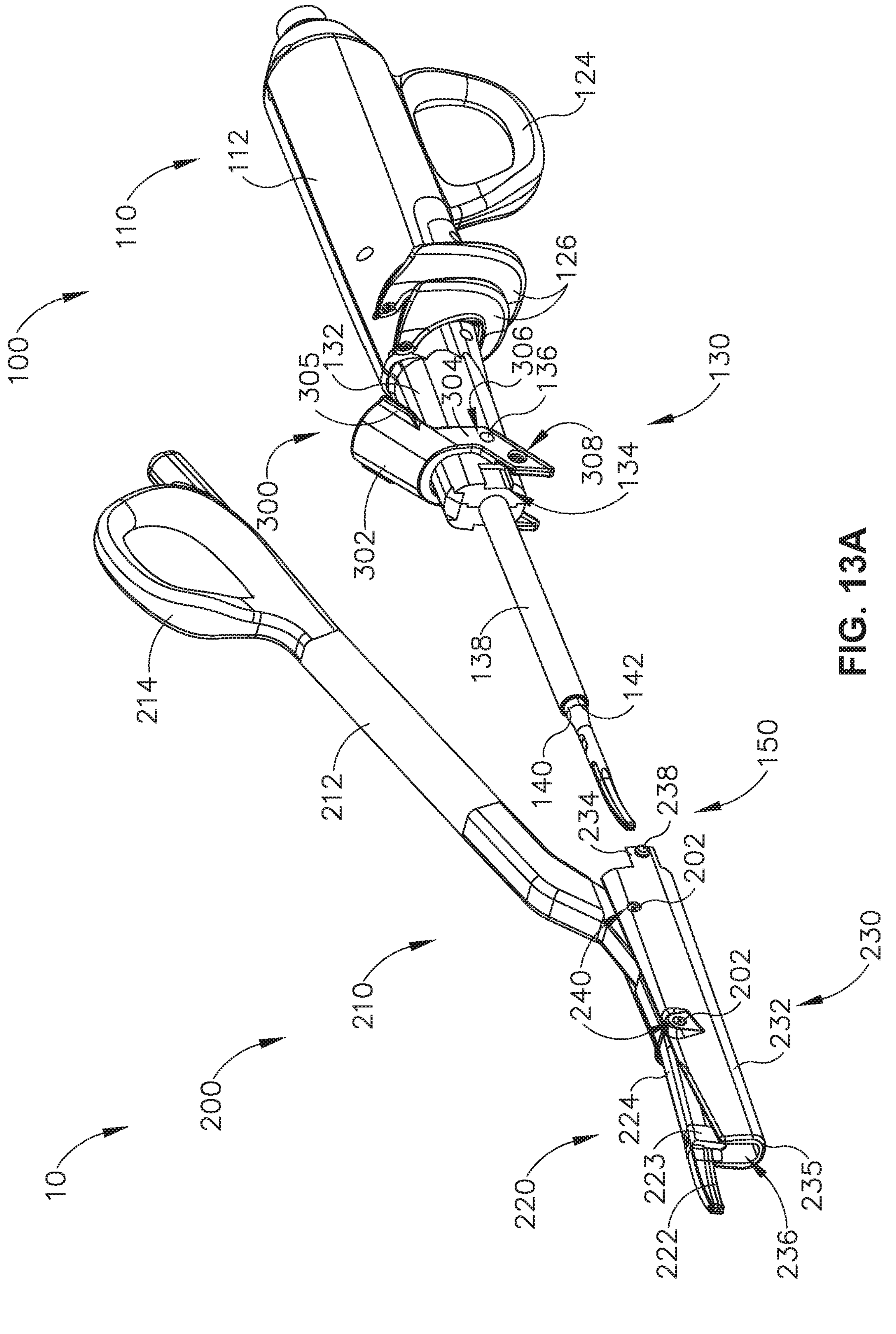
FIG. 13A depicts a perspective view of the second modular assembly of FIG. 8 aligned with the shaft assembly of FIG. 5 in order to couple the modular assemblies together.
Figure 13B:
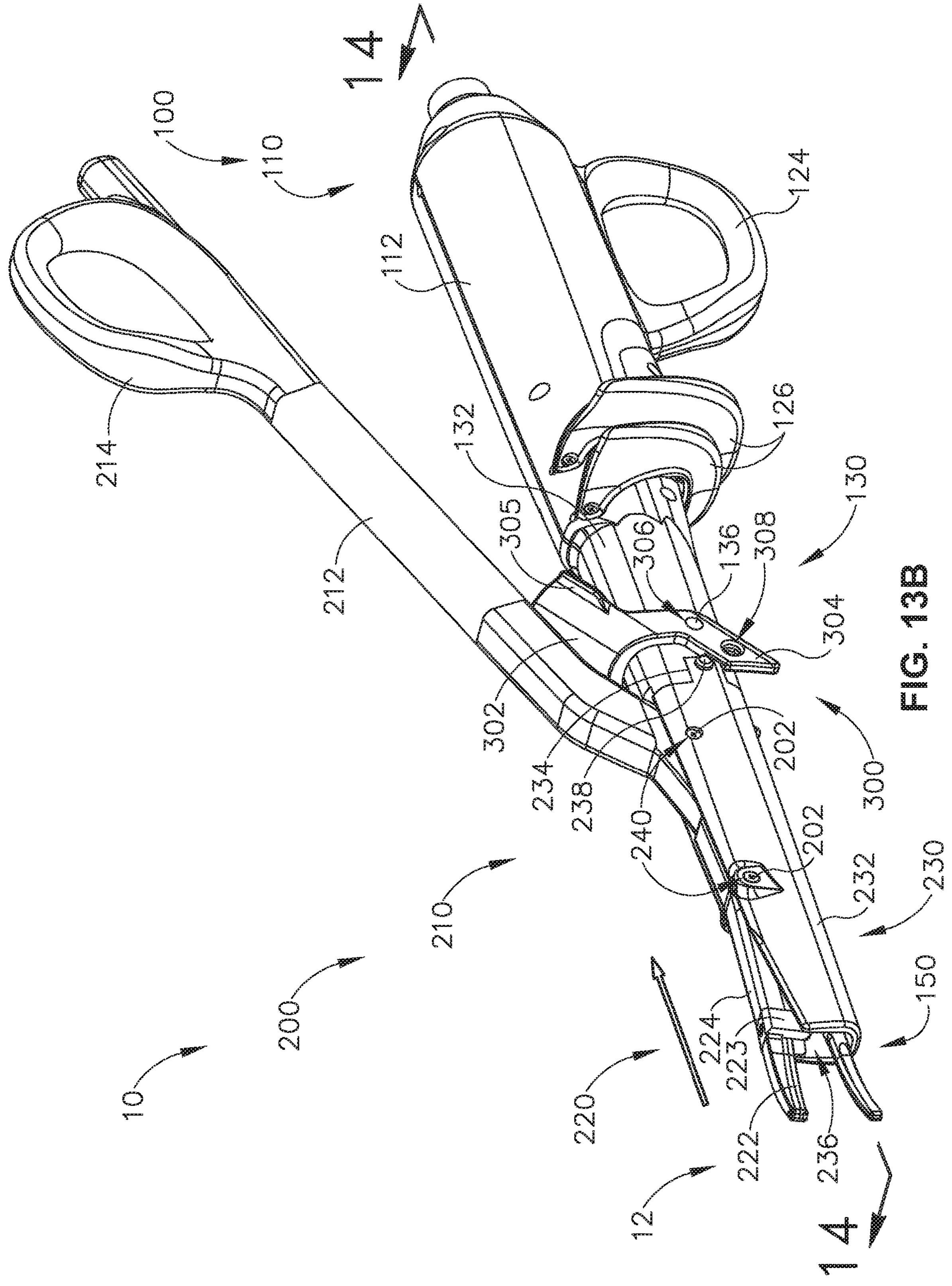
FIG. 13B depicts a perspective view of the second modular assembly of FIG. 8 inserted over the shaft assembly of FIG. 5.
Figure 14A:
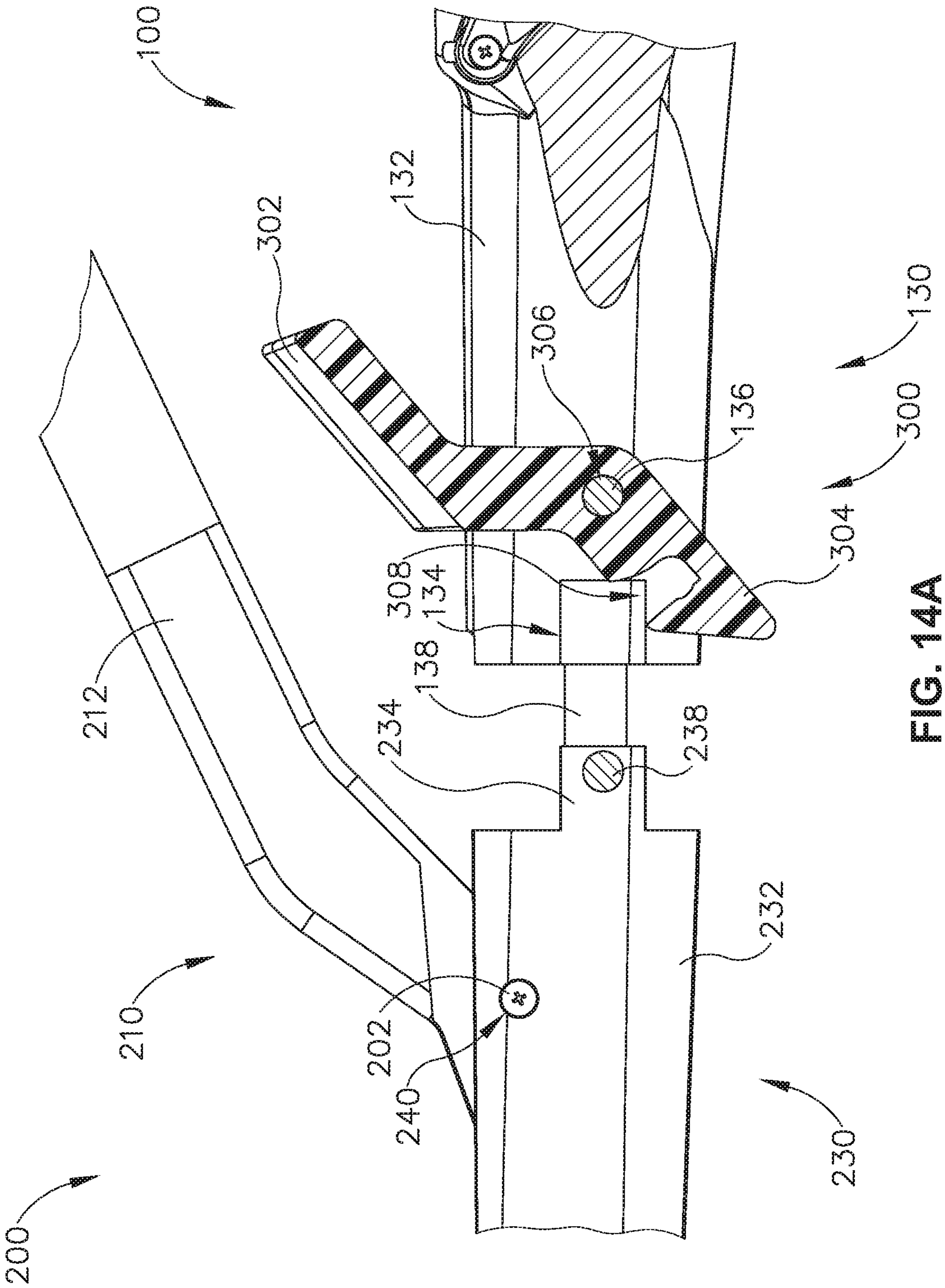
FIG. 14A depicts a cross-sectional side view of the second modular assembly of FIG. 8 partially inserted over the shaft assembly of FIG. 5, taken along line 14-14 of FIG. 13B.
Figure 14B:
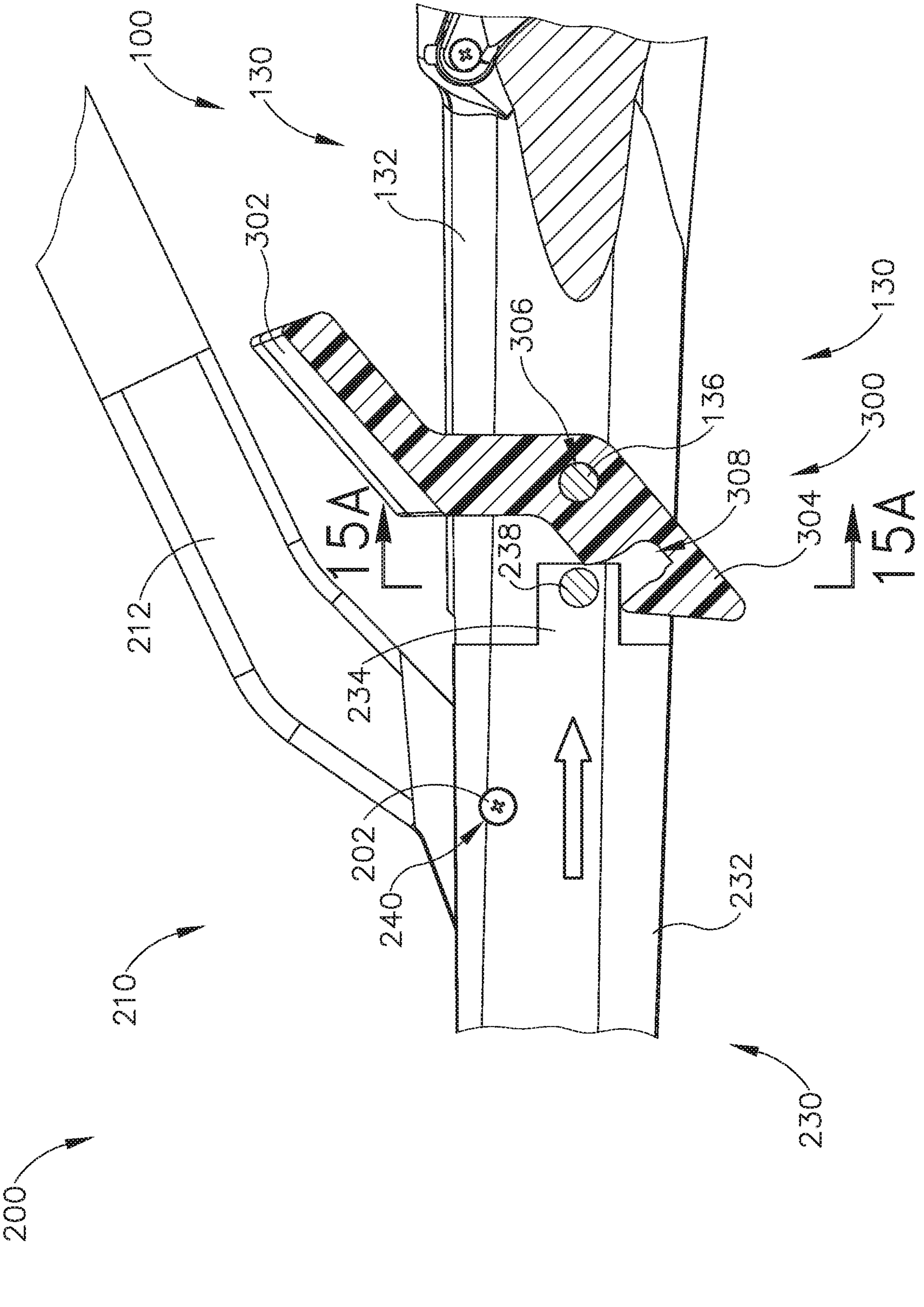
FIG. 14B depicts a cross-sectional side view of the second modular assembly of FIG. 8 further inserted over the shaft assembly of FIG. 5, taken along line 14-14 of FIG. 13B.

As shown between FIGS. 13A-13B and between FIGS. 14A-14B, proximally presented projections (234) are configured to be inserted into recesses (134) defined by proximal outer sheath (132). When proximally presented projections (234) are inserted into recesses (134), distal outer sheath (230) may not rotate relative to proximal outer sheath (132) about a longitudinal axis defined by tube (138). Therefore, proximally presented projections (234) may mate with recesses (134) in order to rotationally fix distal outer sheath (230) relative to proximal outer sheath (132).

Figure 13C:
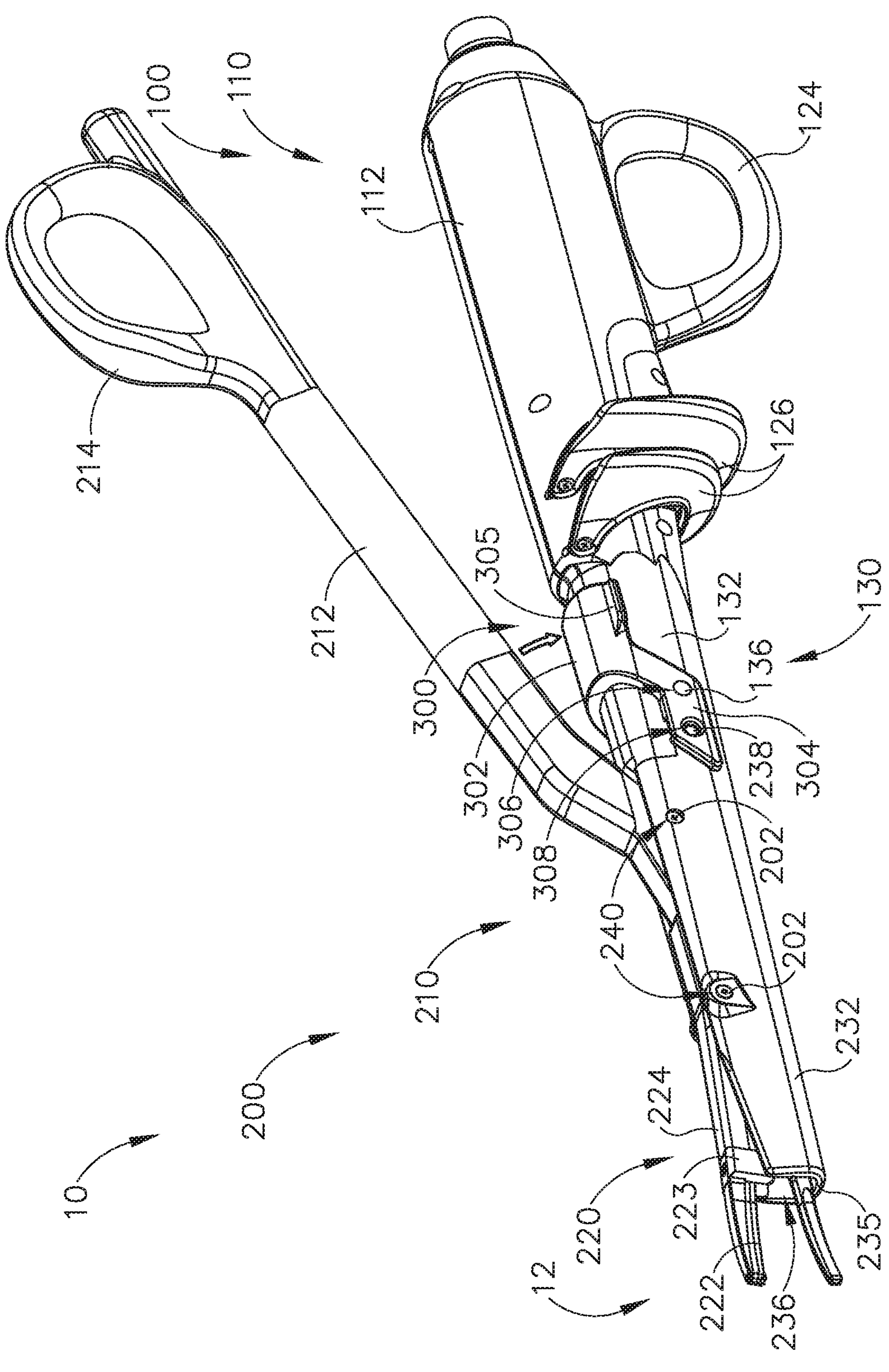
FIG. 13C depicts a perspective view of the second modular assembly of FIG. 8 coupled with the shaft assembly of FIG. 5 via the coupling member of FIG. 7.
Figure 14C:
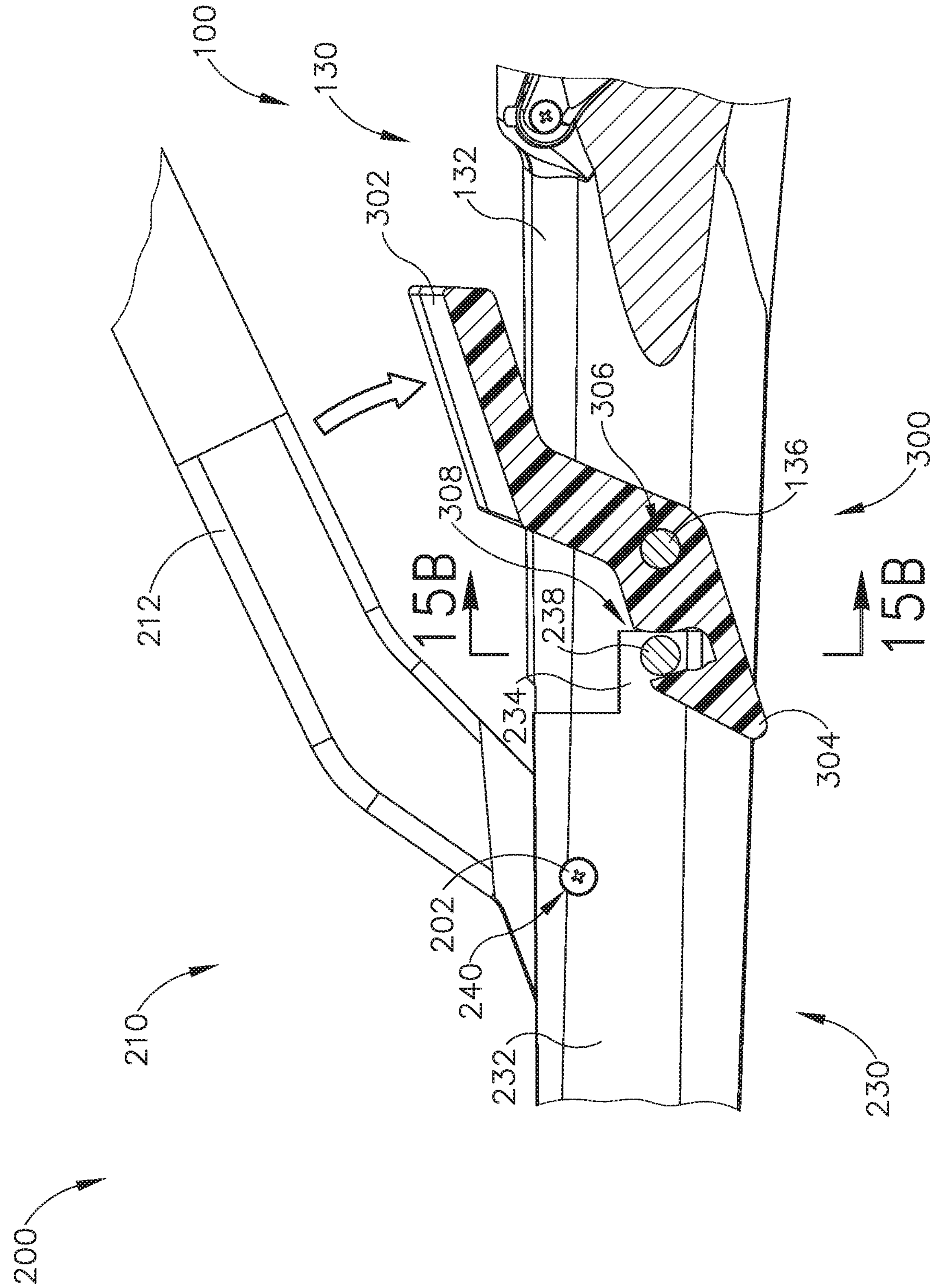
FIG. 14C depicts a cross-sectional side view of the second modular assembly of FIG. 8 inserted over the shaft assembly of FIG. 5 while the coupling member of FIG. 7 is rotated toward a configuration to couple the shaft assembly with the second modular assembly, taken along line 14-14 of FIG. 13B.
Figure 14D:
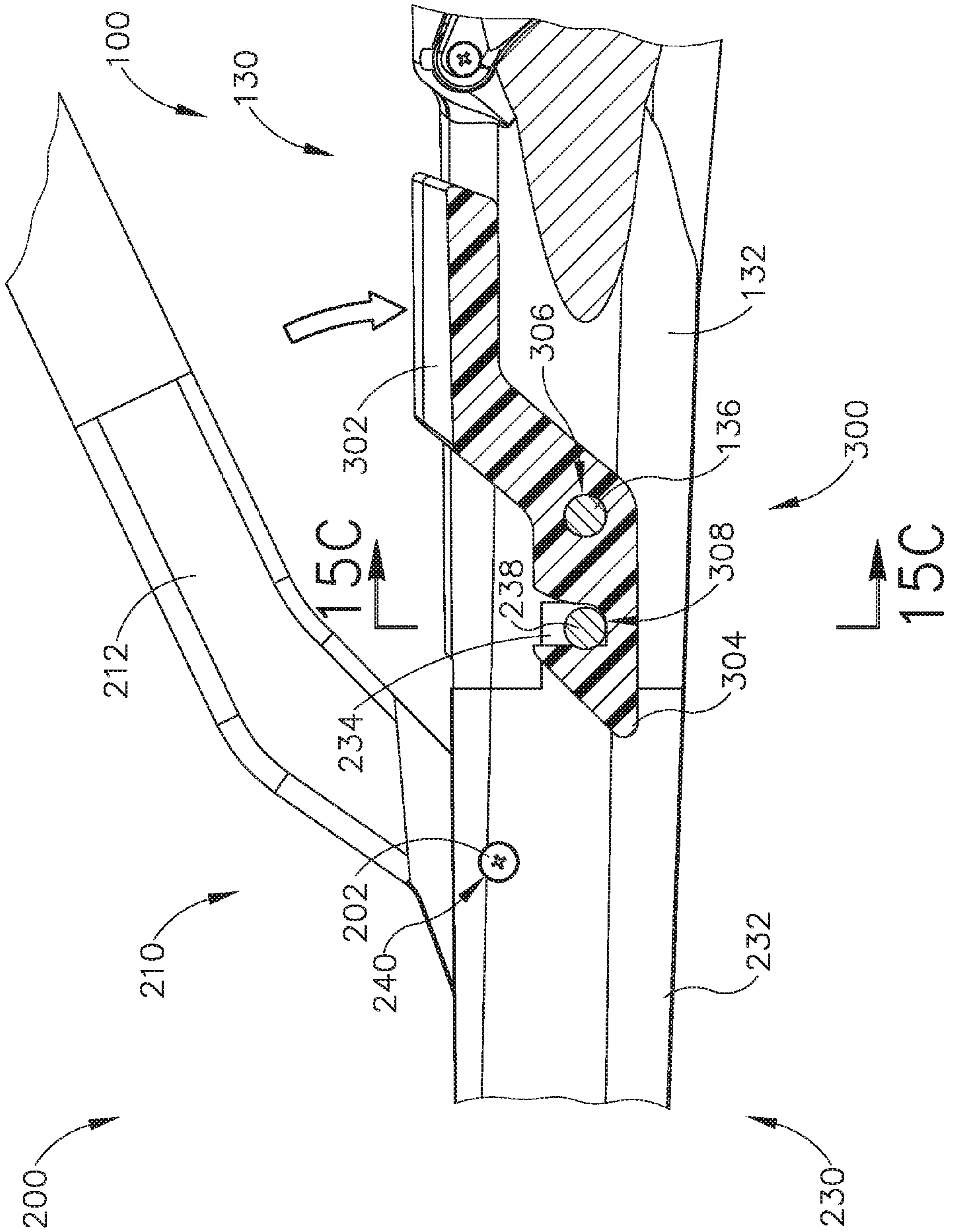
FIG. 14D depicts a cross-sectional side view of the coupling member of FIG. 7 connecting the second modular assembly of FIG. 8 and the shaft assembly of FIG. 5, taken along line 14-14 of FIG. 13B.
Figure 15A:
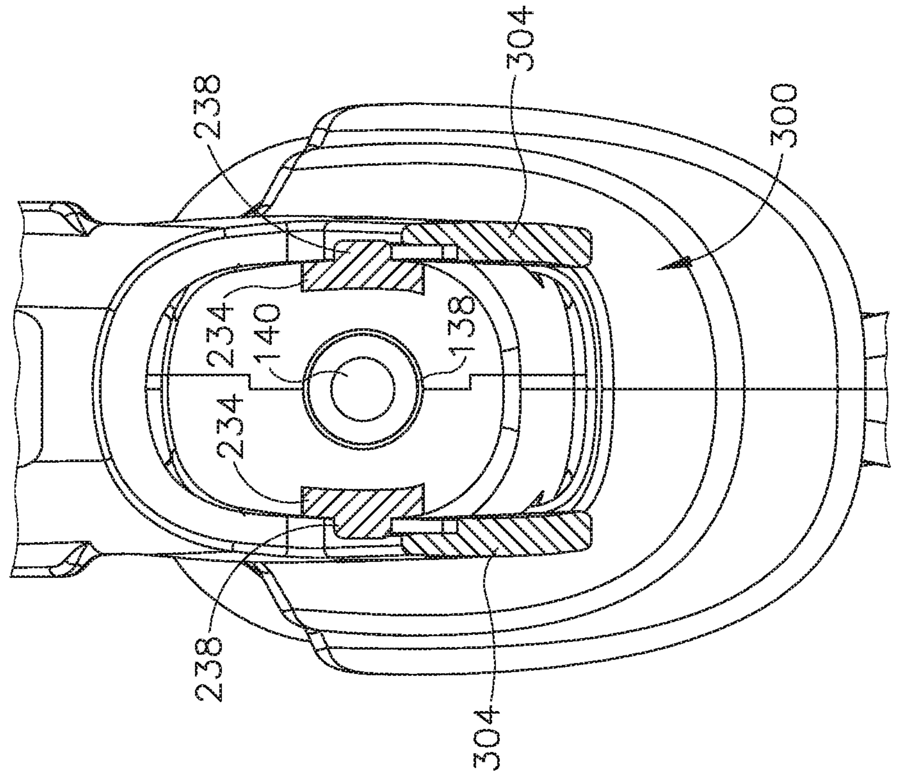
FIG. 15A depicts a cross-sectional front view of the second modular assembly of FIG. 8 inserted over the shaft assembly of FIG. 5, taken along line 15A-15A of FIG. 14B.
Figure 15B:
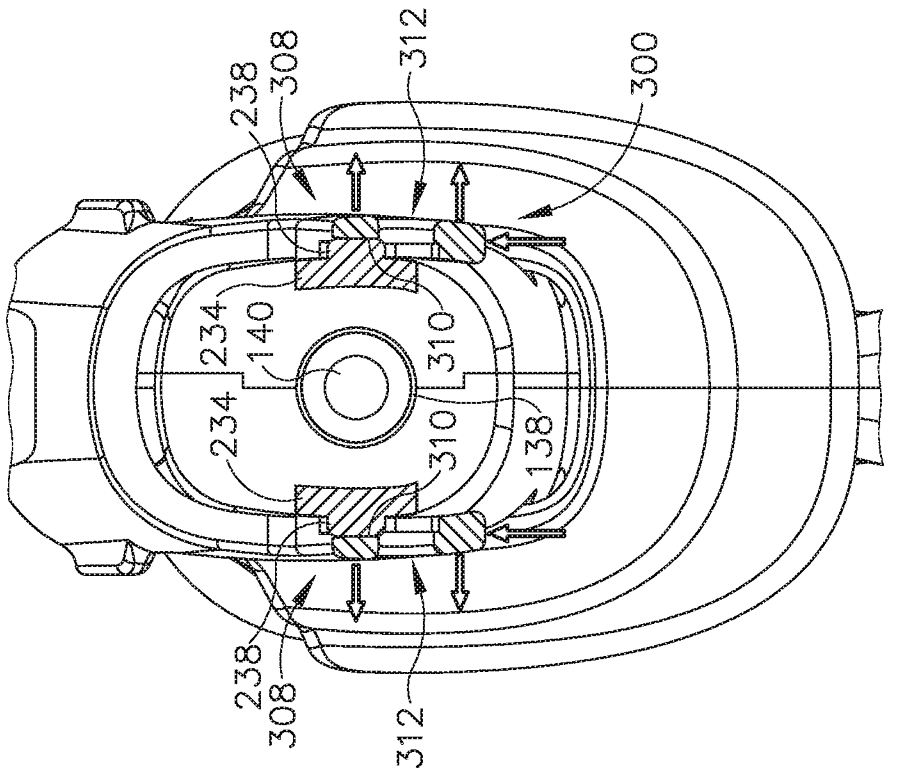
FIG. 15B depicts of cross-sectional front view of the second modular assembly of FIG. 8 inserted over the shaft assembly of FIG. 5 while the coupling member of FIG. 7 is rotated toward a configuration to couple the shaft assembly with the second modular assembly, taken along line 15B-15B of FIG. 14C.
Figure 15C:
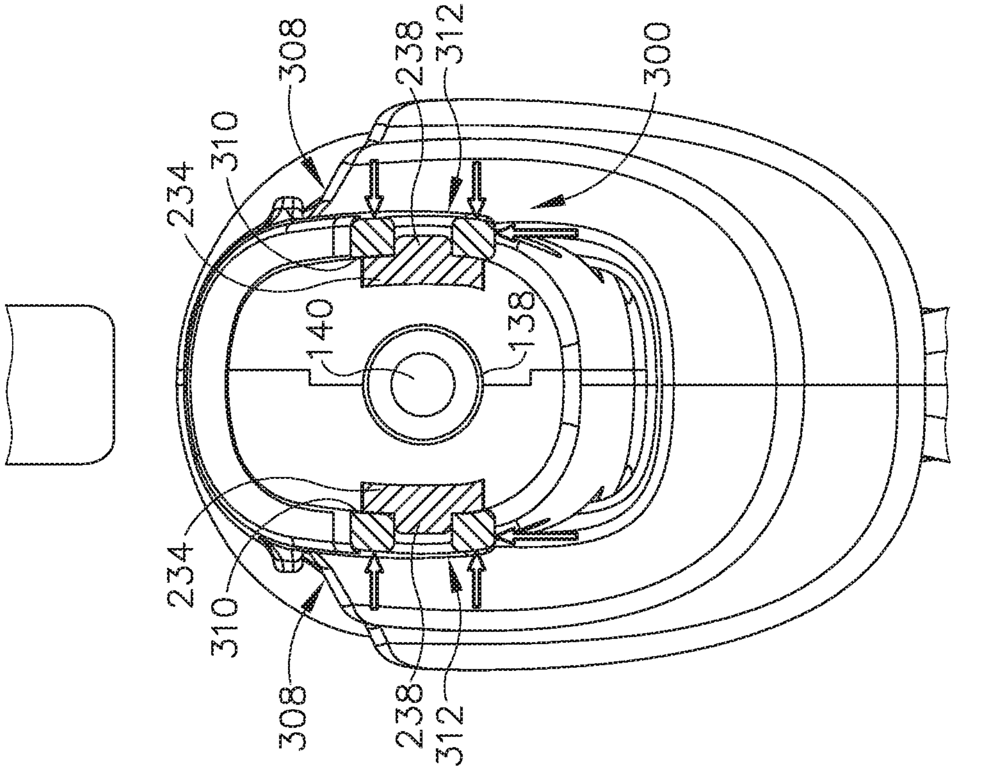
FIG. 15C depicts a cross-sectional front view of the coupling member of FIG. 7 connecting the second modular assembly of FIG. 8 and the shaft assembly of FIG. 5, taken along line 15C-15C of FIG. 14D.

As shown between FIGS. 13B-13C, between FIGS. 14B-14D, and between FIGS. 15A-15C, once distal outer sheath (230) is rotationally fixed relative to proximal outer sheath (132), an operator may rotate coupling member (300) such that locking assembly (308) snap-fits with lateral protrusions (238). In particular, an operator may rotate coupling member (300) about protrusion (136) such that lateral protrusions (238) cam against contact walls (310) of resilient arms (304). As a result, as best seen in FIG. 15B, contact between contact walls (310) and lateral protrusions (238) flex resilient arms (304) outwardly away from proximally presented projections (234). An operator may further rotate coupling member (300) about protrusions (136) such that lateral protrusions (238) no longer abut against contact wall (310), as shown in FIGS. 13C, 14C, and 15C. The resilient nature of resilient arms (304) allows resilient arms (304) to return to a relaxed position such that lateral protrusions (238) rest within coupling recess (312) of locking assembly (308). With locking assembly (308) of coupling member (300) fully attached, and shown in FIGS. 13C, 14D, and 15C, distal outer sheath (230) is longitudinally fixed relative to proximal outer sheath (132), thereby coupling first modular assembly (100) with second modular assembly (200).

If an operator wishes to decouple first modular assembly (100) with second modular assembly (200), an operator may grasp grips (305) to rotate coupling member (300) in the opposite direction about protrusions (136) in order to flex resilient arms (304) to pop out lateral protrusions (238) from coupling recess (312).

As mentioned above, clamp arm assembly (210) and clamp pad assembly (220) are both pivotally coupled with distal outer sheath (230) such that rotation of one assembly (210, 220) relative to distal outer sheath (230) causes rotation of the other assembly (210, 220) relative to distal outer sheath (230).

Clamp arm assembly (210) includes an elongated arm (212), a thumb grip ring (214), a camming protrusion (216), and a pivot coupling (218). Thumb grip ring (214) and elongated arm (212) together provide a scissor grip type configuration in combination with body (112) and finger grip ring (124). Pivot coupling (218) pivotally couples clamp arm assembly (210) with distal outer sheath (230) via pins (202). As will be described in greater detail below, camming protrusion (216) interacts with clamp pad assembly (220) in order to rotate clamp pad assembly (220) in response to rotation of clamp arm assembly (210).

Clamp pad assembly (220) includes a clamp pad (222) facing ultrasonic blade (150), a pair of tissue stops (223) located adjacent to ultrasonic blade (150) and proximal to clamp pad (222), an arm (224) defining both a camming recess (226) and a spring recess (221), a pivot coupling (228), and a leaf spring (225) housed within spring recess (221). In some versions, clamp pad assembly (220) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (220) may incorporate one or more electrodes that is/are operable to apply RF electrosurgical energy to tissue will be apparent to those of ordinary skill in the art in view of the teachings herein.

In the current example, tissue stops (223) longitudinally align with distal face (235) when end effector (12) is in the closed position. Tissue stops (223) and distal face (235) may cooperate to consistently and simply prevent tissue from inadvertently reaching a proximal position within end effector (12) where ultrasonic energy from blade (150) may not adequately sever or seal the tissue. In providing such prevention, tissue stop (223) may eliminate the need for an operator to visualize proximal region of end effector (12) in order to determine whether the tissue has reached an undesirably proximal position within end effector (12).

Camming protrusion (216) is dimensioned to rotate within camming recess (226) while also contacting camming recess (226). Camming protrusion (216) and camming recess (226) are positioned within distal outer sheath (230) such that both are located between pivot couplings (218, 228) while clamp arm assembly (210) and clamp pad assembly (220) are pivotally coupled to distal outer sheath (230). Therefore, as shown between FIGS. 1A-1B and 16A-16B, when an operator rotates elongated arm (212) about pivot coupling (218) toward distal outer sheath (230), camming protrusion (216) rotates away from distal outer sheath (230) about pivot coupling (218). Because camming protrusion (216) is housed within camming recess (226), upward movement of camming protrusion (216) about pivot coupling (218) causes upward movement of camming recess (226) about pivot coupling (228). Upward movement of camming recess (226) about pivot coupling (228) rotates arm (224) such that clamp pad (222) rotates toward ultrasonic blade (150). Therefore, closure of elongated arm (212) of clamp arm assembly (210) toward handle assembly (110) leads to closure of clamp pad (222) toward ultrasonic blade (150). It should therefore be understood that when first modular assembly (100) and second modular assembly (200) are connected, an operator may squeeze thumb grip ring (214) toward body (112) to thereby clamp tissue between clamp pad assembly (220) and ultrasonic blade (150) to compress tissue against ultrasonic blade (150). When ultrasonic blade (150) is activated during such compression, clamp pad assembly (220) and ultrasonic blade (150) cooperate to transect and/or seal the compressed tissue.

As mentioned above, leaf spring (225) is housed within spring recess (221). As best seen in FIGS. 16A-16B, leaf spring (225) is dimensioned such that a portion of leaf spring (225) extends out of spring recess (221) to make contact against tube (138) in order to provide electrical continuity between the one or more RF electrodes of end effector (12) and the source of electrical power. It should be understood that leaf spring (225) maintains this electrical continuity throughout the range of motion of clamp pad assembly (220). It should also be understood that any other suitable kinds of features may be used to provide electrical continuity between the one or more RF electrodes of end effector (12) and the source of electrical power.

In some versions, one or more resilient members are used to bias clamp pad assembly (220) toward the open position shown in FIGS. 1A and 16A. Of course, any other suitable kind of resilient member may be used as would be apparent to one having ordinary skill in the art in view of the teachings herein, such as a torsion spring. Alternatively, clamp pad assembly (220) need not necessarily be biased toward the open position.

Pivot couplings (218, 228) of clamp arm assembly (210) and clamp pad assembly (220) being located within longitudinal pathway (236) of distal outer sheath (230) may provide certain desirable advantages as compared to clamp arm assembly (210) and clamp pad assembly (220) pivotally coupling with an exterior of distal outer sheath (230). For instance, there may be a reduced chance of inadvertently pinching tissue due to rotation of clamp arm assembly (210) and clamp pad assembly (220) with pivot couplings (218, 228) being housed within U-shaped body (232). In other words, U-shaped body (232) may protect tissue from being inadvertently pinched by rotation of clamp arm assembly (210) and clamp pad assembly (220) relative to distal outer sheath (230). Additionally, the width of second modular assembly (200) may be reduced due to pivot couplings (218, 228) being housed within longitudinal pathway (236) of distal outer sheath (230). It may also be easier to fabricate desired components due to the simplified shapes of clamp arm assembly (210) and clamp pad assembly (220). A reduction of tolerance stack may also be an advantage to storing pivot couplings (218, 228) within the interior of distal outer sheath (230).

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pat. Nos. 9,023,071; 8,461,744; 9,381,058; U.S. Pub. No. 2012/0116265; U.S. Pat. Nos. 9,393,037; 9,095,367; and/or U.S. Pub. No. 2015/0080925, entitled "Alignment Features for Ultrasonic Surgical Instrument," published Mar. 19, 2015, the disclosure of which is incorporated by reference herein.

Figure 17:
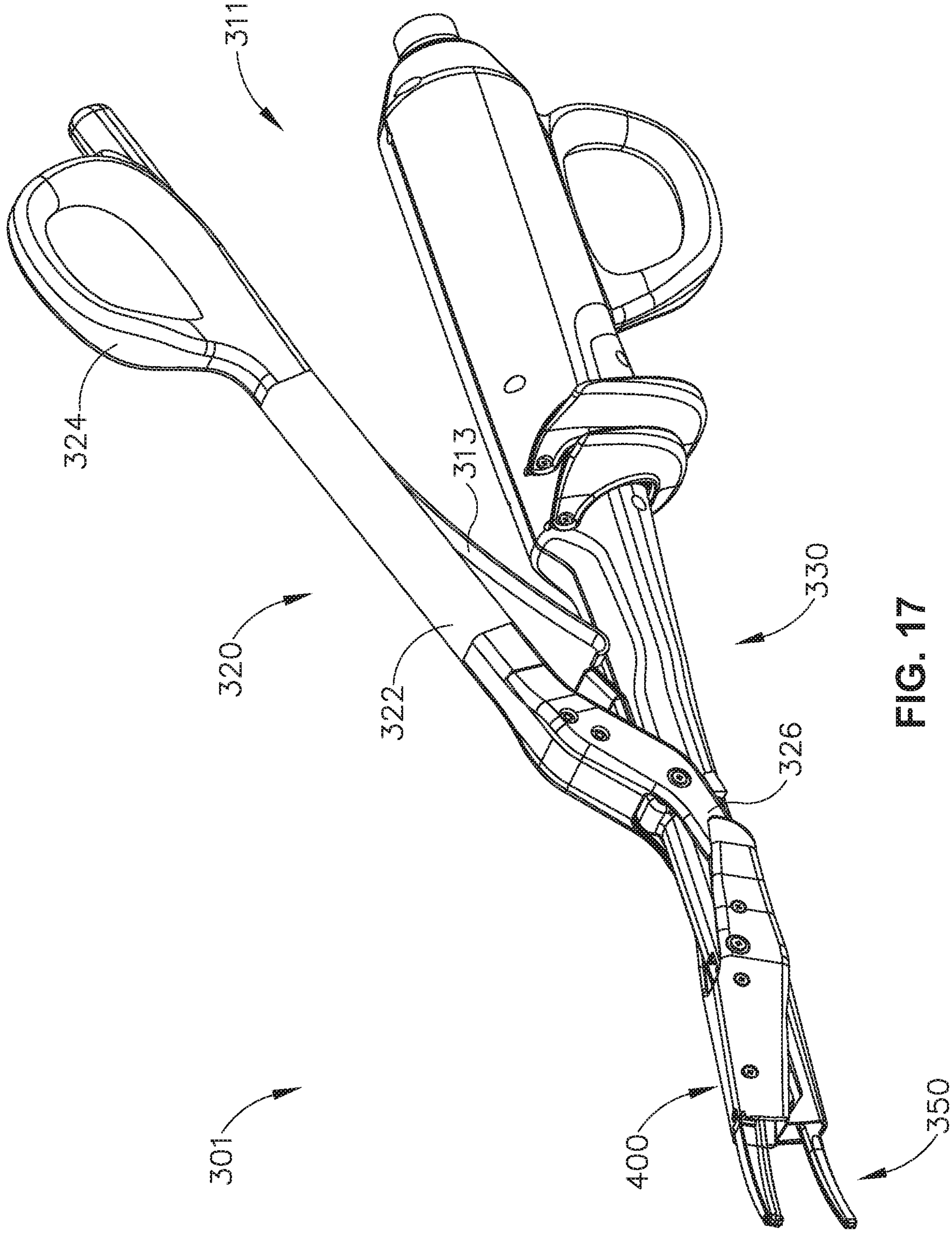
FIG. 17 depicts a perspective view of a second exemplary surgical instrument, with an end effector of the instrument in an open configuration.
Figure 18:
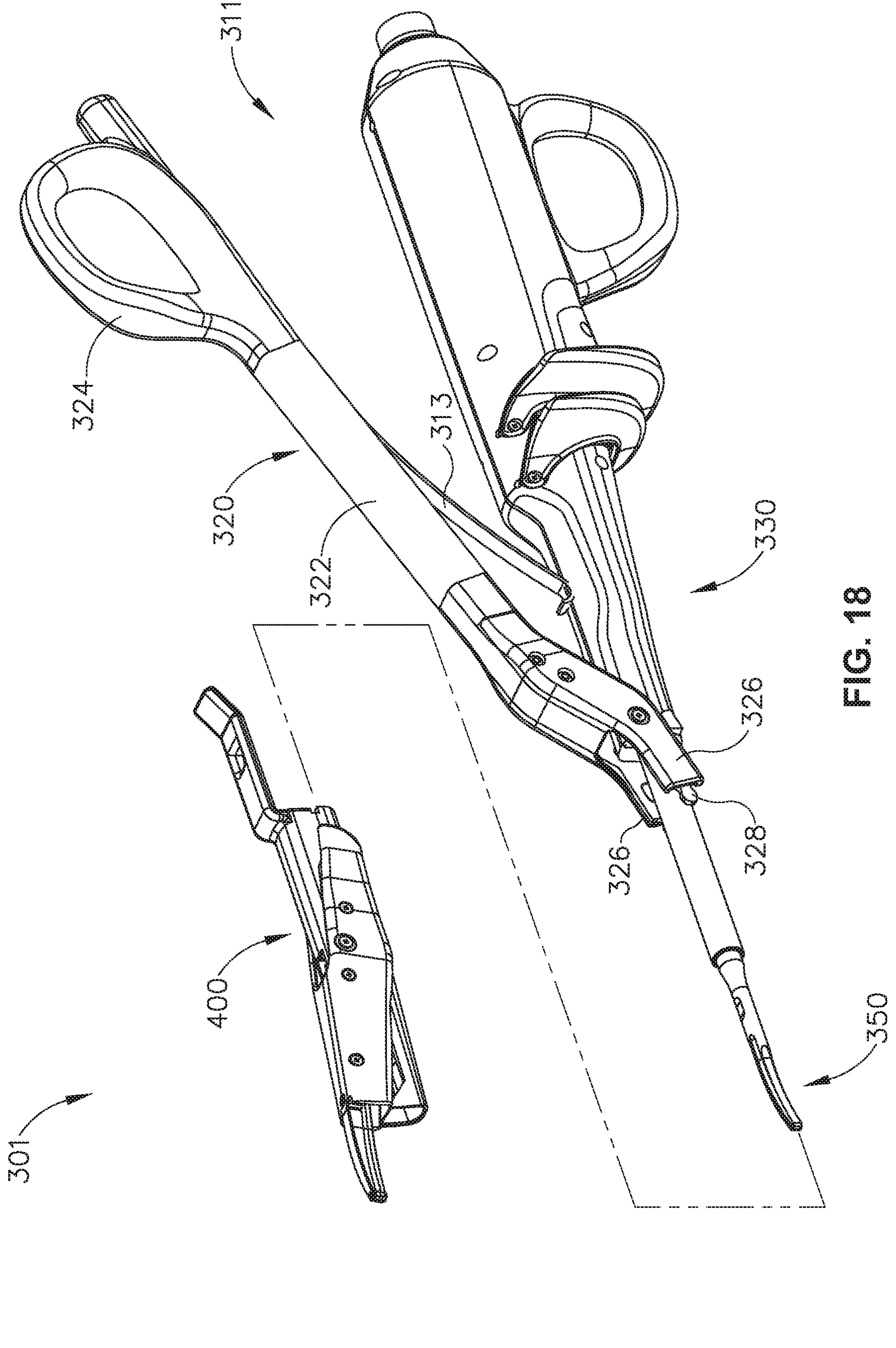
FIG. 18 depicts a partially exploded perspective view of the instrument of FIG. 17.

II. Second Exemplary Ultrasonic Surgical Instrument for Open Surgical Procedures FIGS. 17-18 show a second exemplary ultrasonic surgical instrument (301). Except as otherwise described below, instrument (301) of this example may be constructed and operable just like instrument (10) described above. Certain details of instrument (301) will therefore be omitted from the following description, it being understood that such details are already provided above in the description of instrument (10).

Instrument (301) of the present example comprises a handle assembly (311), a clamp arm actuator (320), a shaft assembly (330), and a clamp arm assembly (400). Handle assembly (311) of this example is configured and operable just like handle assembly (110) described above, such that details of handle assembly (311) will not be reiterated here.

Figure 19:
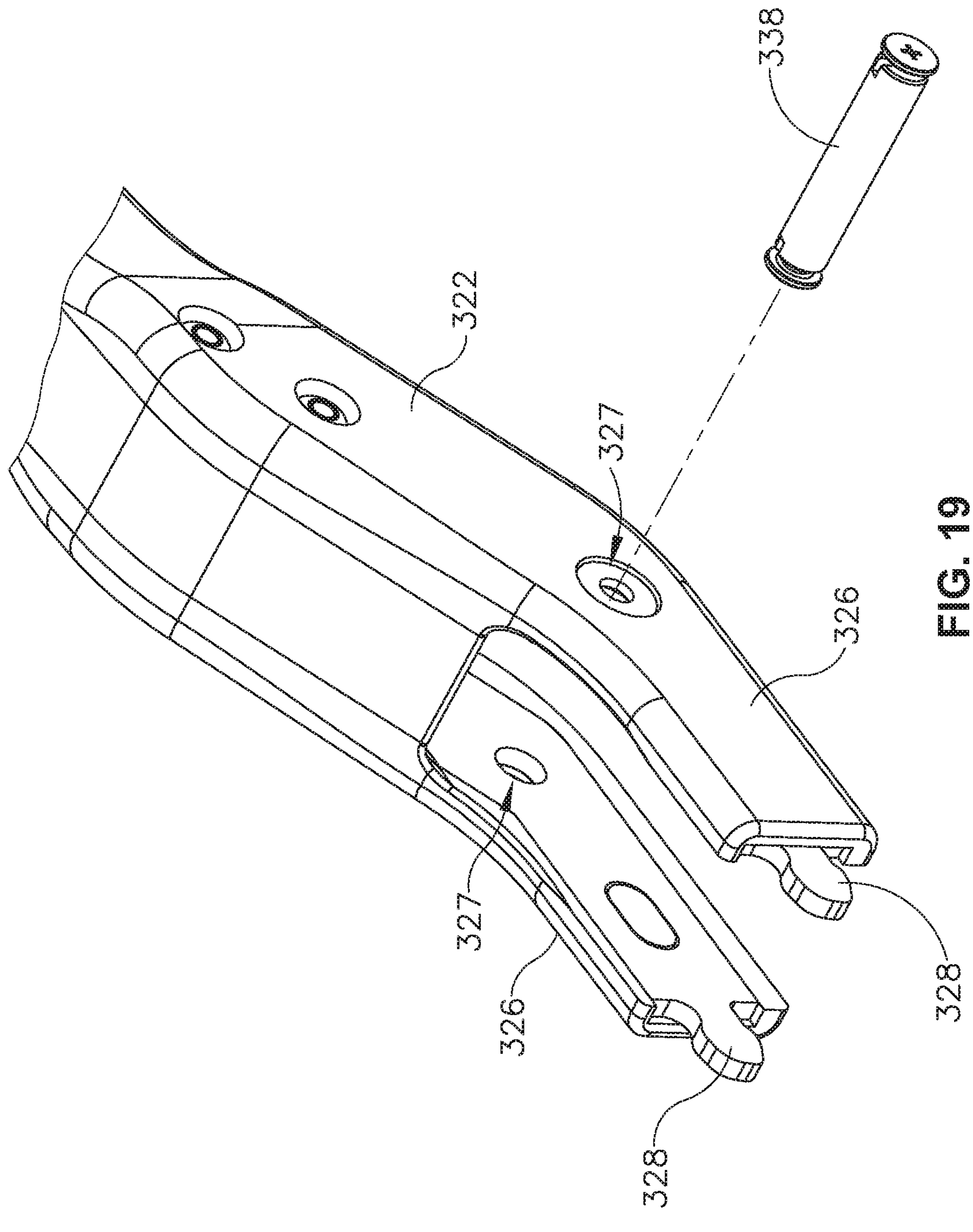
FIG. 19 depicts a partial perspective view of the distal end of a clamp arm actuator of the instrument of FIG. 17.

Clamp arm actuator (320) is pivotably coupled with shaft assembly (330). In the present example, clamp arm actuator (320) is not removable from shaft assembly (330). Clamp arm actuator (320) of the present example comprises a shaft (322). A thumb ring (324) is positioned at the proximal end of shaft (322). As best seen in FIGS. 18-19, pair of projections (326) extend distally from shaft (322). Projections (326) are laterally spaced apart from each other and extend parallel to each other. As best seen in FIG. 19, the distal end of each projection (326) includes a camming protrusion (328). Camming protrusions (328) are configured to cooperate with clamp arm assembly (400), in a manner similar to camming protrusions (216), as will be described below. As also best seen in FIG. 19, projections (326) also define a pair of pin openings (327), which are configured to receive pin (338). Pin (338) provides a pivotable coupling between clamp arm actuator (320) and shaft assembly (330).

Figure 20:
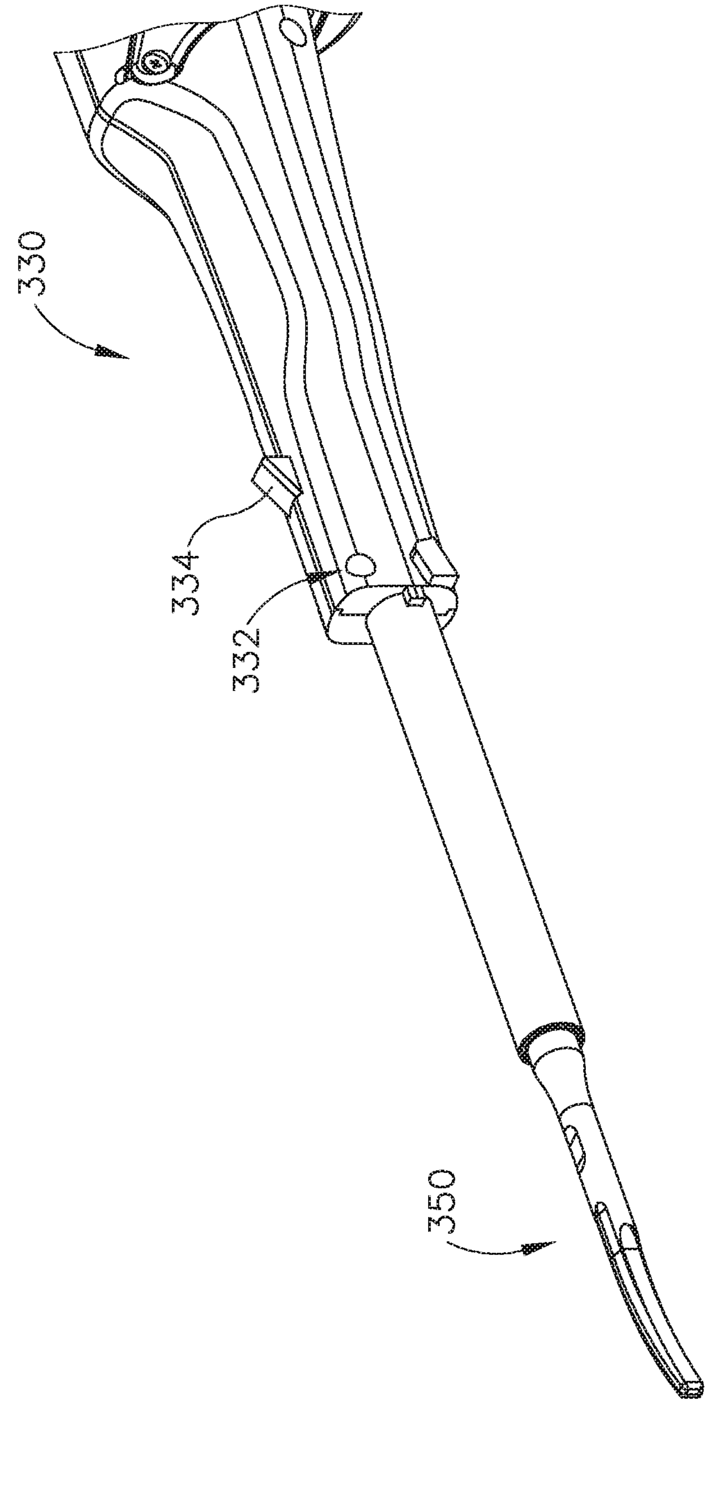
FIG. 20 depicts a perspective view of a shaft assembly and ultrasonic blade of the instrument of FIG. 17.

Shaft assembly (330) extends distally from handle assembly (311) and is substantially identical to shaft assembly (130) described above except for the differences described below. An ultrasonic blade (350), which is identical to ultrasonic blade (150) described above, is positioned at the distal end of shaft assembly (130). As best seen in FIG. 20, shaft assembly (330) defines an opening (332) that is configured to receive pin (338) to thereby provide a pivotable coupling between clamp arm actuator (320) and shaft assembly (330). As also shown in FIG. 20, shaft assembly (330) includes a ramped latch protrusion (334), which is configured to engage clamp arm assembly (400) as will be described in greater detail below.

Figure 21:
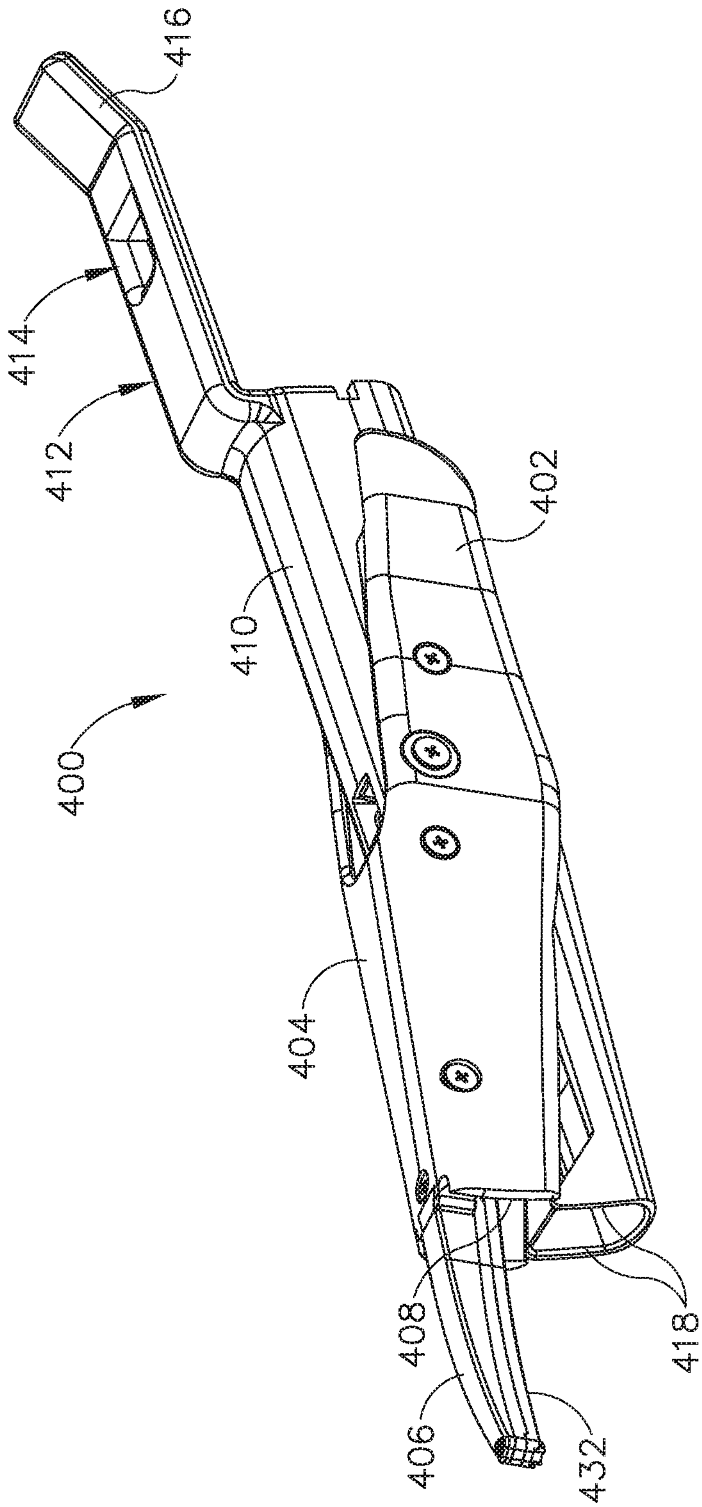
FIG. 21 depicts a perspective view of a removable clamp arm assembly of the instrument of FIG. 17.
Figure 22:
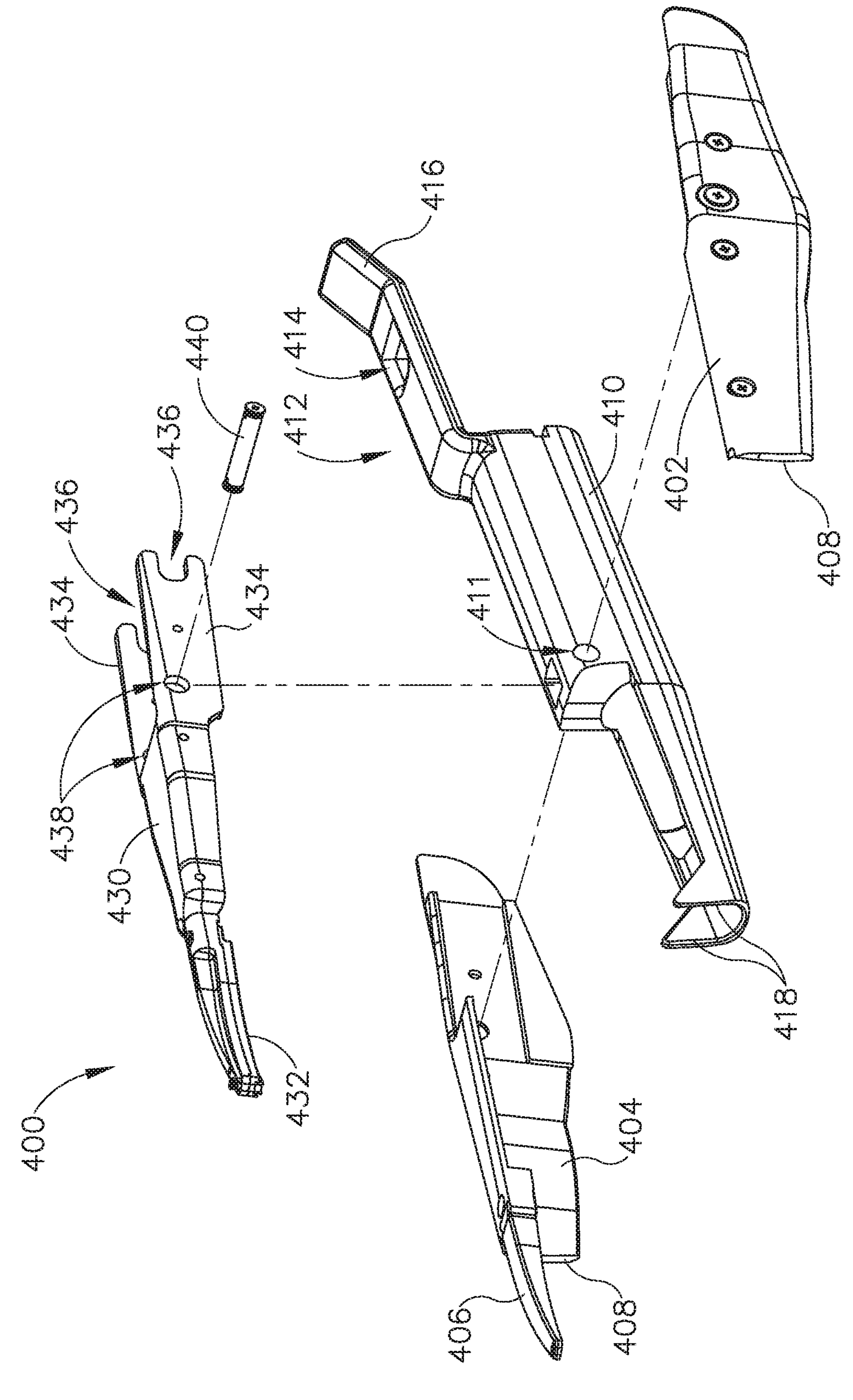
FIG. 22 depicts an exploded perspective view of the clamp arm assembly of FIG. 21.

As shown in FIGS. 21-22, clamp arm assembly (400) of the present example comprises a pair of shrouds (402, 404) partially encompassing a clamp arm body (430), which is pivotally coupled with a stationary body (410). Each shroud includes a distally presented tissue stop edge (408). Stationary body (410) also includes a pair of distally presented tissue stop edges (418). Edges (408, 418) are configured to cooperate to consistently and restrict proximal positioning of tissue like tissue stops (223) and distal face (235) described above. Shroud (404) of the present example also includes a distally projecting shield member (406).

Stationary body (410) of the present example further includes a pin opening (411) and a proximally projecting latch member (412). Latch member (412) defines a latch opening (414) and a ramp (416). Latch member (412) is configured to cooperate with latch protrusion (334) of shaft assembly (330) to selectively secure clamp arm assembly (400) to shaft assembly (330). In particular, when clamp arm assembly (400) is initially provided separately from shaft assembly (330), an operator may align clamp arm assembly (400) with shaft assembly (330) along a common axis, and then insert blade (350) and the remaining distal portion of shaft assembly (330) into clamp arm assembly (400). Ramp (416) will eventually engage latch protrusion (334), which will provide a camming action that causes latch member (412) to deflect away from the longitudinal axis. As the operator continues to insert shaft assembly (330) through clamp arm assembly (400), latch protrusion (334) eventually reaches latch opening (414), at which point latch member (412) resiliently returns to a straight, non-deflected state. At this stage, latch protrusion (334) is disposed in latch opening (414) and thereby secures clamp arm assembly (400) to shaft assembly (330). When the operator wishes to remove clamp arm assembly (400) from shaft assembly (330), the operator may simply engage ramp (416) and thereby urge latch member (412) to a deflected state where latch member (412) can clear latch protrusion (334); then pull clamp arm assembly (400) away from shaft assembly (330). Other suitable structures and techniques that may be used to secure clamp arm assembly (400) to shaft assembly (330), and to remove clamp arm assembly (400) from shaft assembly (330), will be apparent to those of ordinary skill in the art in view of the teachings herein.

Clamp arm body (430) of the present example comprises a clamp pad (432) and a pair of proximal projections (434). Clamp pad (432) is positioned and configured to compress tissue against ultrasonic blade (350) when clamp arm assembly (400) is secured to shaft assembly (330). Shield member (406) of shroud (404) is configured to extend over the exterior of the distal end of clamp arm body (430), without covering clamp pad (432). Shield member (406) thus enables clamp pad (432) to contact tissue directly. Projections (438) each comprise a respective proximally presented recess (436) and a pair of pin openings (438). A pin (440) is positioned in pin openings (411, 438) to thereby pivotally couple clamp arm body (430) with stationary body (410). Shrouds (402, 404) are fixedly secured to clamp arm body (430) such that shrouds (402, 404) pivot with clamp arm body (430) relative to stationary body (410).

Figure 23:
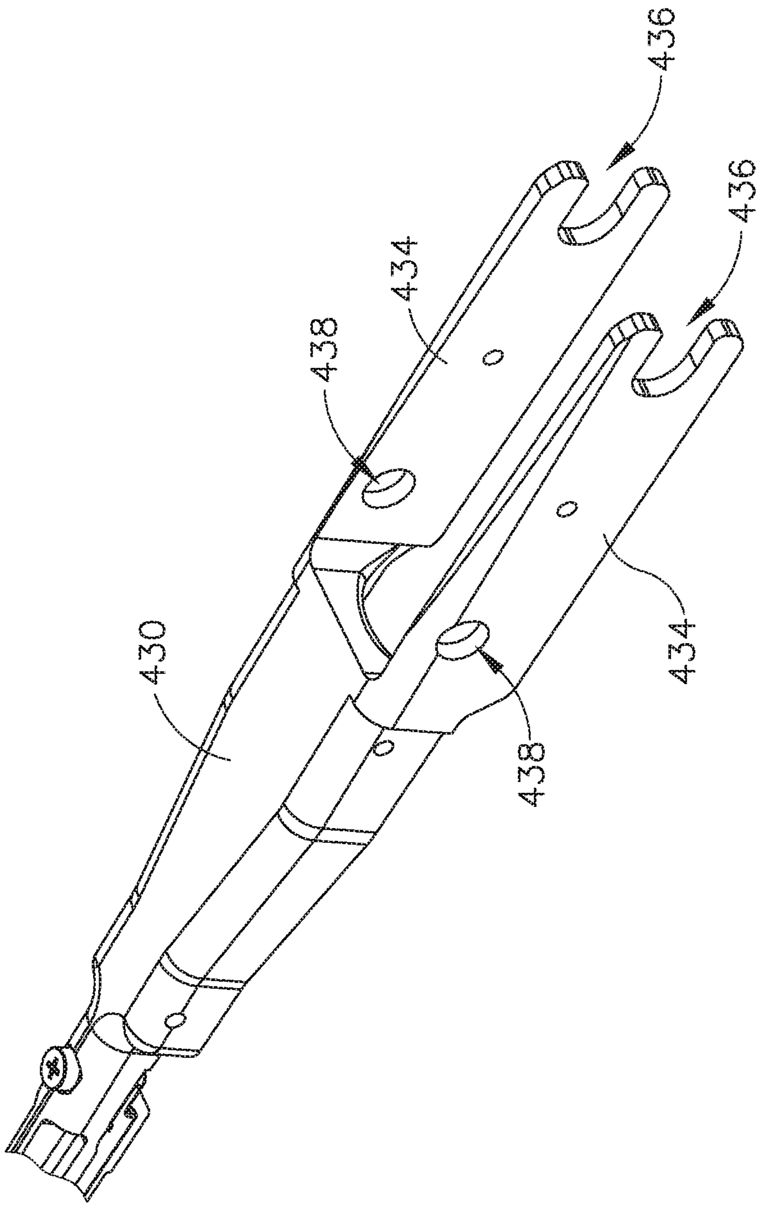
FIG. 23 depicts a partial perspective view of a proximal end of a clamp arm body of the clamp arm assembly of FIG. 22.
Figure 24:
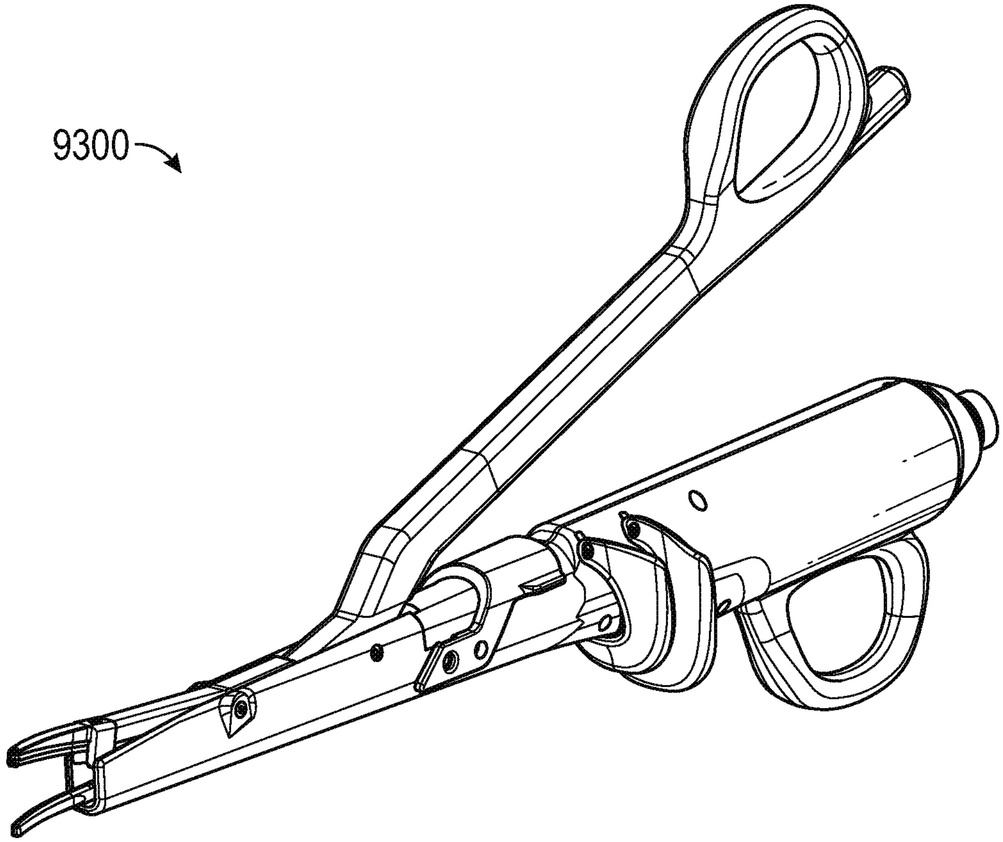
FIG. 24 depicts a perspective view of a third exemplary surgical instrument, similar to the surgical instrument of FIG. 1A.
Figure 25:
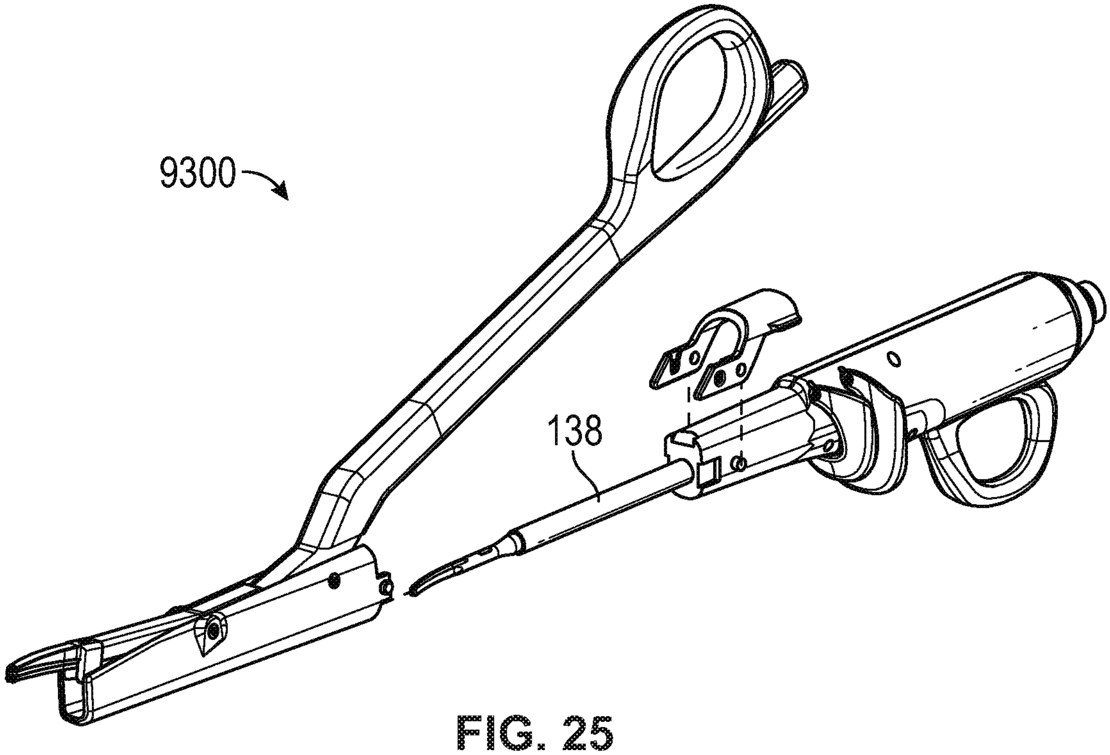
FIG. 25 depicts an exploded perspective view of the surgical instrument of FIG. 24.
Figure 26:
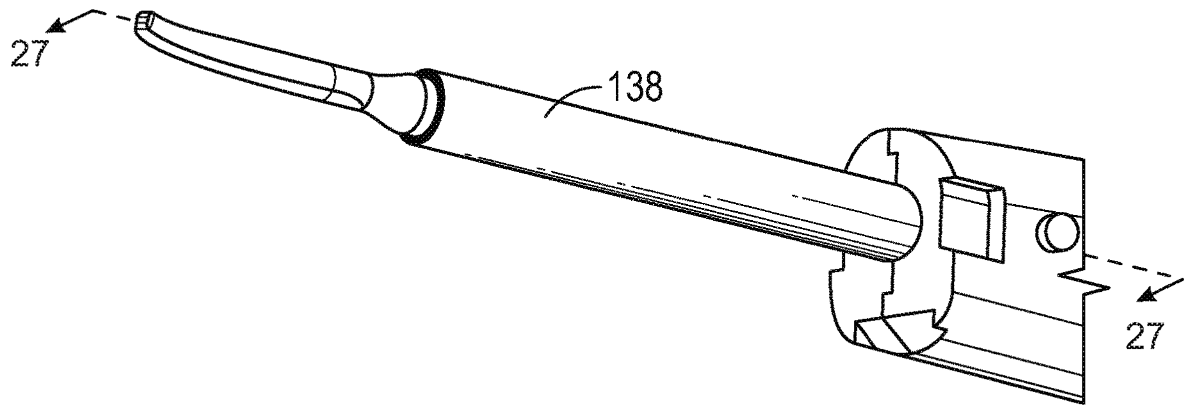
FIG. 26 depicts a perspective view of a waveguide of the surgical instrument of FIG. 25.
Figure 27:
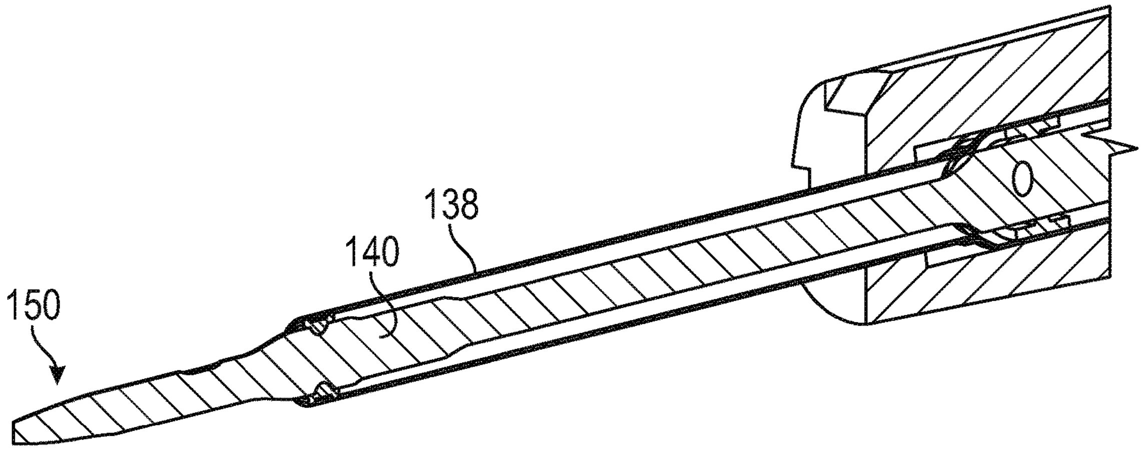
FIG. 27 depicts a cross-sectional view taken along line 27-27 of FIG. 26.

As shown in FIG. 23, recesses (436) have a generally U-shaped configuration. Recesses (436) are configured to receive camming protrusions (328) of clamp arm actuator (320). In other words, when shaft assembly (330) is inserted into clamp arm assembly (400) as described above, camming protrusions (328) will enter recesses (436) when latch member (412) reaches the point at which latch member (412) secures clamp arm assembly (400) to shaft assembly (330). When the operator removes clamp arm assembly (400) from shaft assembly (330), camming protrusions (328) may freely exit recesses (436), as clamp arm actuator (320) remains secured to shaft assembly (330). As best seen in FIG. 17, shrouds (402, 404) are configured to cover the interfaces between recesses (436) and camming protrusions (328). It should be understood that the relationship between recesses (436) and camming protrusions (328) is substantially identical to the relationship between camming protrusion (216) and camming recess (226) described above. Thus, recesses (436) and camming protrusions (328) provide a pivoting coupling between clamp arm body (430) and clamp arm actuator (320).

As noted above, clamp arm actuator (320) is pivotally coupled with shaft assembly (330) via pin (338); and clamp arm body (430) is pivotally coupled with stationary body (410) via pin (440); while stationary body (410) is fixedly secured to shaft assembly (330). The pivoting interface between recesses (436) and camming protrusions (328) is longitudinally positioned between the longitudinal positions of pins (338, 440). It should therefore be understood that clamp arm actuator (320) and clamp arm body (430) cooperate to provide a compound lever assembly. When an operator pivots thumb ring (324) toward handle assembly (311), the compound lever action provides corresponding pivotal movement of clamp pad (432) toward ultrasonic blade (350).

In the present example, a resilient beam (313) is secured to clamp arm actuator (320) and slidably bears against shaft assembly (330), such that resilient beam (313) resiliently urges clamp arm actuator (320) away from handle assembly (311). Thus, when an operator relaxes their grip on thumb ring (324), resilient beam (313) will urge thumb ring (324) away from handle assembly (311), thereby urging clamp pad (432) away from ultrasonic blade (350). Of course, any other suitable components and arrangements may be used to provide a resilient bias to clamp arm actuator (320). Alternatively, such resilient bias may simply be omitted.

III. Sealing Interface Between Tube and Waveguide

Figure 6:
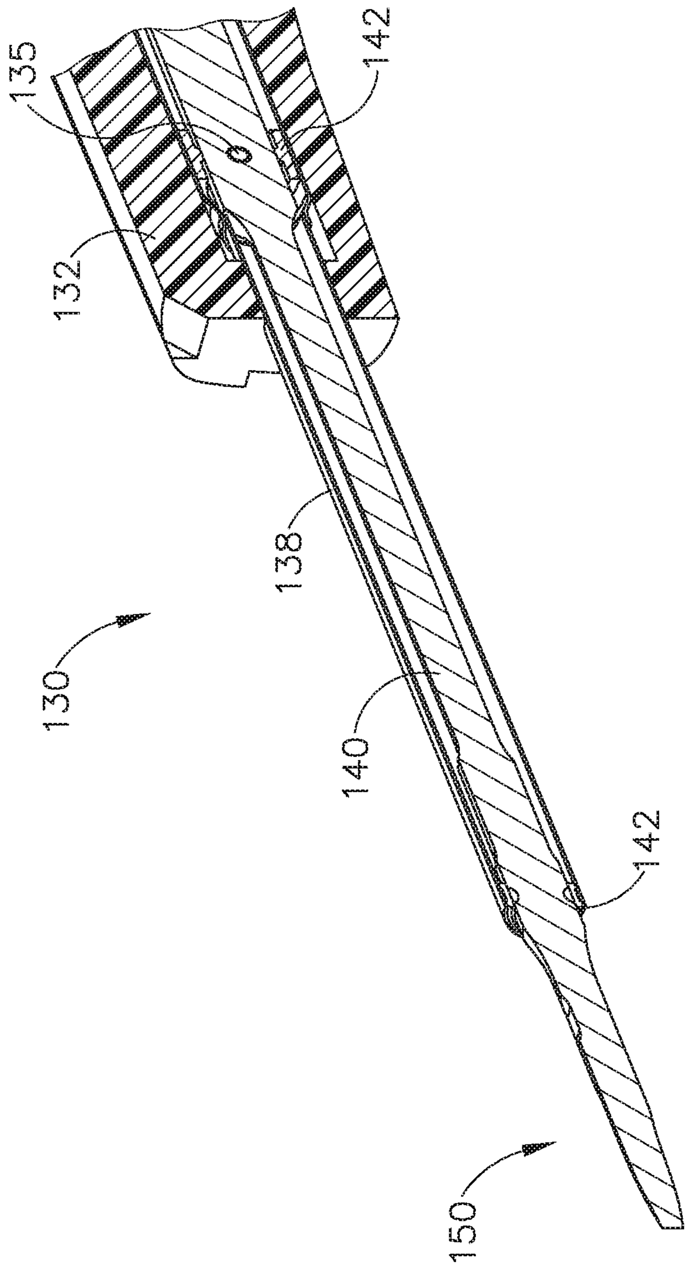
FIG. 6 depicts a cross-sectional perspective view of the shaft assembly and blade assembly of FIG. 5.

As shown in FIG. 6, waveguide (140) may be supported by tube (138) via seals (142) located between an interior of tube (138) and an exterior of waveguide (140). Seals (142) may also prevent unwanted matter and fluid from entering portions of tube (138) housing waveguide (140). In those versions of instrument (10) illustrated in FIG. 6, the most distal seal (142) is manually placed onto waveguide (140) such as by rolling seal (142) onto waveguide (140) after passing ultrasonic blade (15) through seal (142). This manual manipulation and placement of seal (142) may degrade the material of seal (142), leading to either early degradation of seal (142) or even an unsealed fit between waveguide (140) and seal (142).

FIGS. 24-28E illustrate a third exemplary surgical instrument (9300), similar to instrument (10), with like elements having like numbering. In some versions of instrument (9300), rather than physically applying an o-ring style seal such as seal (142) onto waveguide (140), instrument (9300) include a seal (9302) molded directly onto waveguide (140). In some versions of instrument (9300), seal (9302) is overmolded onto waveguide (140) in situ to allow the material of seal (9302) to bond with both the exterior of waveguide (140) and the interior of tube (138), thus creating a tightfitting seal therebetween to prevent unwanted matter and fluid from entering tube (138).

As shown in FIGS. 24-28E, within instrument (9300), tube (138) and waveguide (140) define a cavity (9304) therebetween. A form (9306) is assembled within cavity (9304) to overmold seal (9302) in situ to tube (138) and waveguide (140). Form (9306) includes a proximal form portion (9308) and a distal form portion (9310) which may be brought together to define a mold space (9312) therebetween.

Proximal form portion (9308) is an elongated tamper style device which enters cavity (9304) from the proximal end of tube (138). Proximal form portion (9308) includes a shutoff portion (9314) which generally matches the space between tube (138) and waveguide (140) in order to prevent the seal forming material from expanding past proximal form portion (9308). Proximal form portion (9308) further includes a sleeve portion (9316) which may be flexible to adjust to the contours or angles of tube (138). In operation, a user or machine extends proximal form portion (9308) into cavity (9304) in the direction of Arrow (9300A) by manipulating sleeve portion (9316) to extend shutoff portion (9314) to the proper placement within tube (138). As positioned, shutoff portion (9314) is configured to prevent any seal forming material from moving beyond shutoff portion (9314) and into the proximal area of tube (138).

Distal form potion (9310) is a capping style device, a portion of which is configured to enter into cavity (9304) from the distal end of tube (138). Distal form portion (9310) includes an internal portion (9318) and an external portion (9320). Internal portion (9318) is configured to extend into cavity (9304), while external portion (9320) is configured to abut the outermost end of tube (138). Distal form portion (9310) also defines an internal channel (9322), which is sized to fit waveguide (140) therein. In operation, a user or machine extends distal form portion (9310) over waveguide (140) in the direction of Arrow (9300B), with waveguide (140) disposed within internal channel (9322) and until external portion (9320) abuts the outer end of tube (138). This orients internal portion (9318) in cavity (9304), distal to proximal form portion (9308). As distal form portion (9310) is pressed against tube (138), form (9306) is created and mold space (9312) is defined.

Figure 28A:
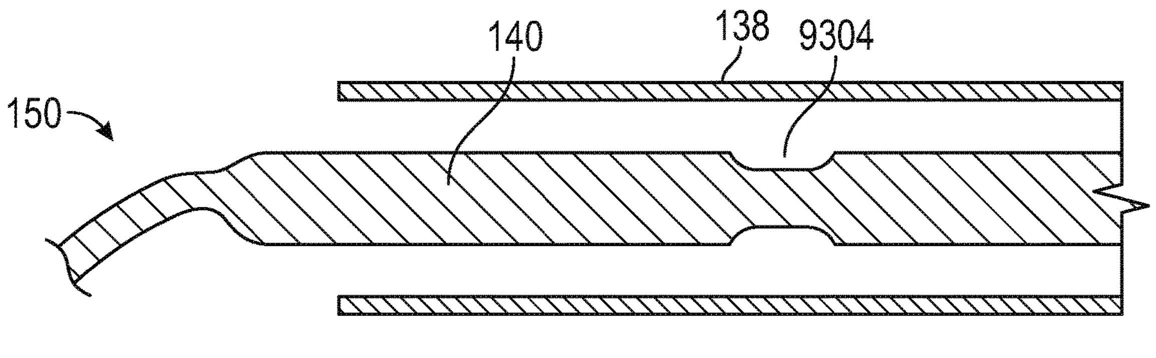
FIG. 28A depicts a cross-sectional view similar to FIG. 27, with the waveguide disposed within an exemplary tube.
Figure 28B:
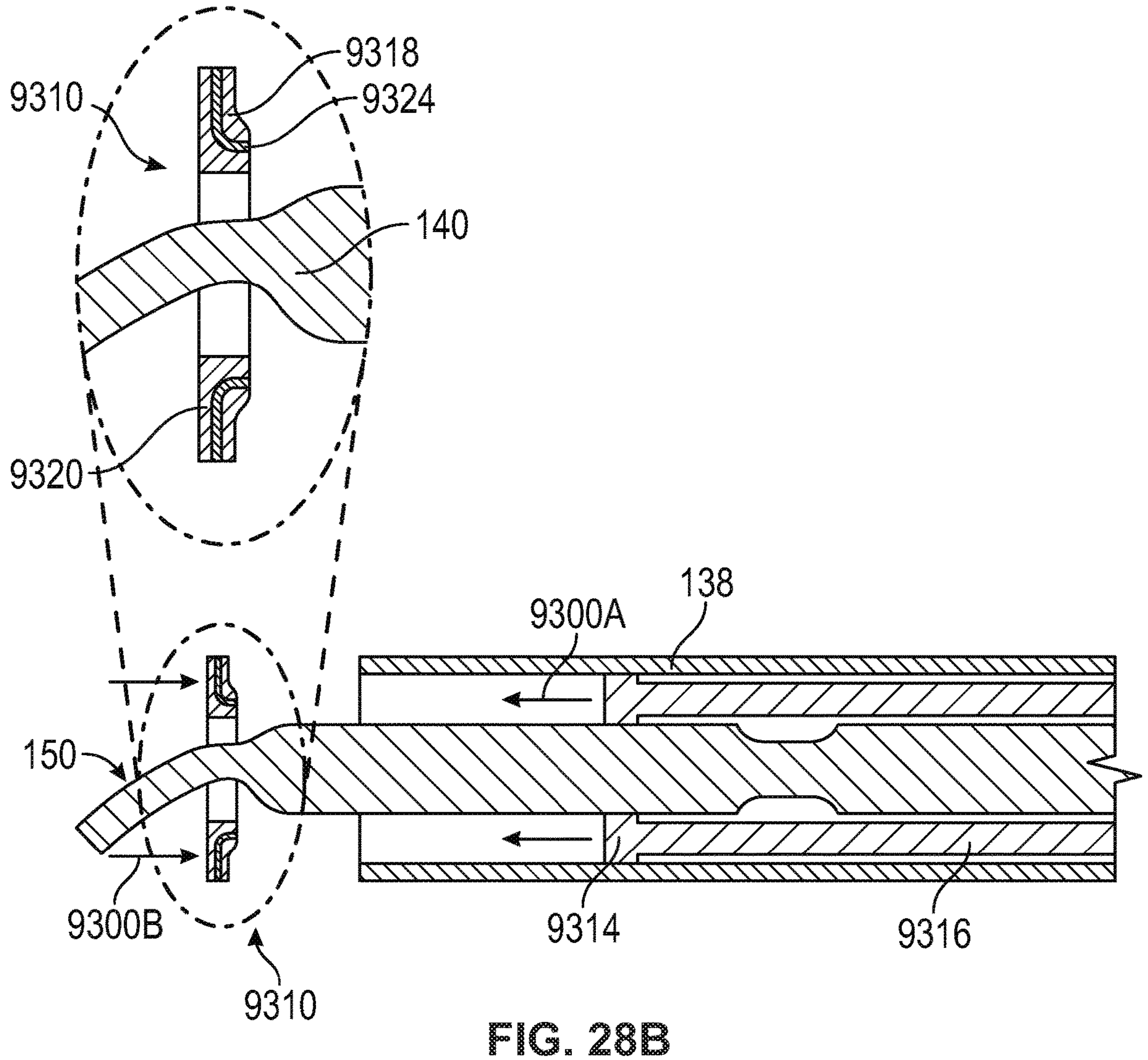
FIG. 28B depicts a cross-sectional view similar to FIG. 28A, with an exemplary distal form portion of an exemplary form disposed on the waveguide and an exemplary proximal form portion extended into a cavity defined by the tube and the waveguide.
Figure 28C:
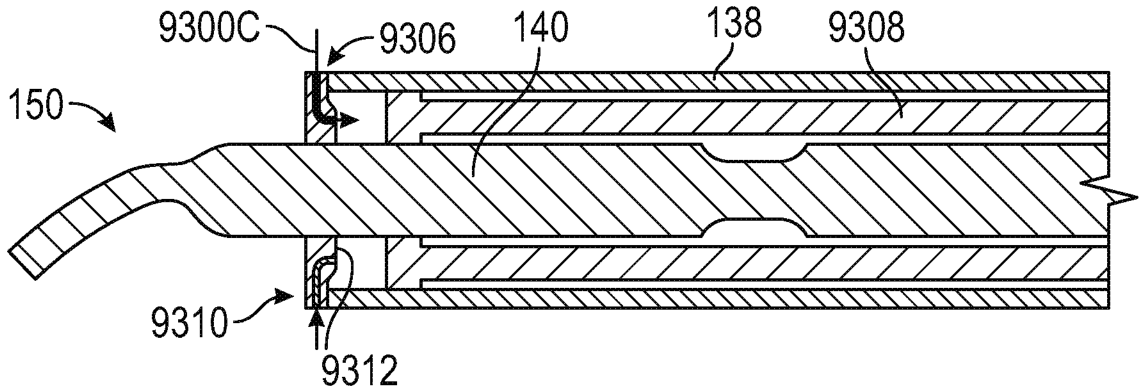
FIG. 28C depicts a cross-sectional view similar to FIG. 28B, with the distal form portion connected to the tube and cooperating with the proximal form portion and tube to define a mold space therein.
Figure 28D:
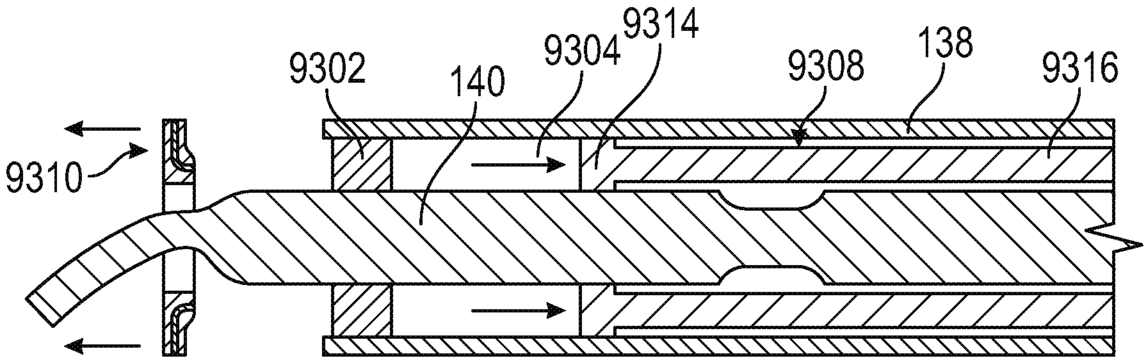
FIG. 28D depicts a cross-sectional view similar to FIG. 28C, with the proximal form portion and distal form portion being removed from the cavity and leaving a seal disposed in the mold space.
Figure 28E:
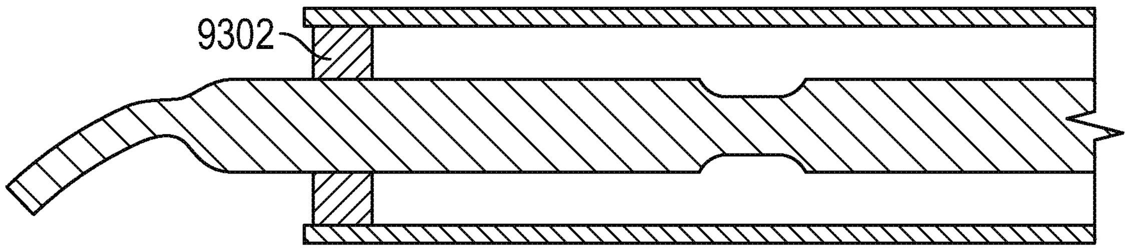
FIG. 28E depicts a cross-sectional view similar to FIG. 28A with the seal disposed between the tube and the waveguide.

As shown in FIG. 28B, distal form portion (9310) defines a material channel (9324). Material channel (9324) extends from the exterior of external portion (9320) to the exterior of internal portion (9322). Material channel (9324) allows material used in forming seal (9302) to travel through distal form portion (9310) in the direction of Arrow (9300C) and into mold space (9312) while distal form portion (9310) is held against tube (138). This allows seal (9302) to be formed through distal form portion (9310) while distal form portion (9310) is coupled with tube (138).

With particular reference to FIGS. 28A-28E, once the material used to create seal (9302) is poured into form (9306), seal (9302) is allowed to set and/or cure. After seal (9302) is sufficiently cured, both proximal form portion (9308) and distal form portion (9310) are removed from tube (138), leaving seal (9302) adhered to both tube (138) and waveguide (140) to prevent liquid and debris from entering cavity (9304).

In some versions of instrument (9300), seal (9302) is located at a position along the length of waveguide (140) corresponding to a node associated with resonant ultrasonic vibrations communicated through waveguide (140). Therefore, contact between waveguide (140) and seal (9302) may not affect ultrasonic vibrations communicated through waveguide (140).

IV. Surgical Instrument with an Accessible Outer Sheath

As discussed above with respect to FIGS. 1A-16B, distal outer sheath (230) is configured to reduce the likelihood of inadvertently pinching tissue due to rotation of clamp arm assembly (210) and clamp pad assembly (220) and may thus protect tissue. While such protection may be beneficial to the patient in some instances, distal outer sheath (230) also inhibits access within surgical instrument (10) and, more particular, access about tube (138) and ultrasonic blade (150). In some uses, blood and other bodily fluids and tissues may travel proximally along ultrasonic blade and about tube (138), thus hindering cleaning and effective sterilization of one or more portions of surgical instrument (10) for reuse.

It may thus be desirable in some instances to provide surgical instrument (10), or any such instrument as those described herein, with an accessible outer sheath (9612, 9712, 9812, 9912, 10012) configured to provide access within surgical instrument (10) for cleaning and, more particularly, sterilizing, surgical instrument (10). Of course, alternative access for uses other than cleaning may similarly be performed. The invention is thus not intended to be unnecessarily limited to use for cleaning. Furthermore, while the following accessible outer sheaths (9612, 9712, 9812, 9912, 10012) are shown in distinct positions with distinct securements (9620, 9720, 9820, 9920, 10020), it will be appreciated that accessible outer sheaths (9612, 9712, 9812, 9912, 10012) with one or more securements (9620, 9720, 9820, 9920, 10020) may be incorporated into any surgical instrument described herein, exchanged, or moved so as to make one or more portions of outer sheaths detachable from a remainder of the surgical instrument. To this end, like reference numeral indicate like features.

A. A Hinge Cover for a First Accessible Outer Sheath

Figure 29:
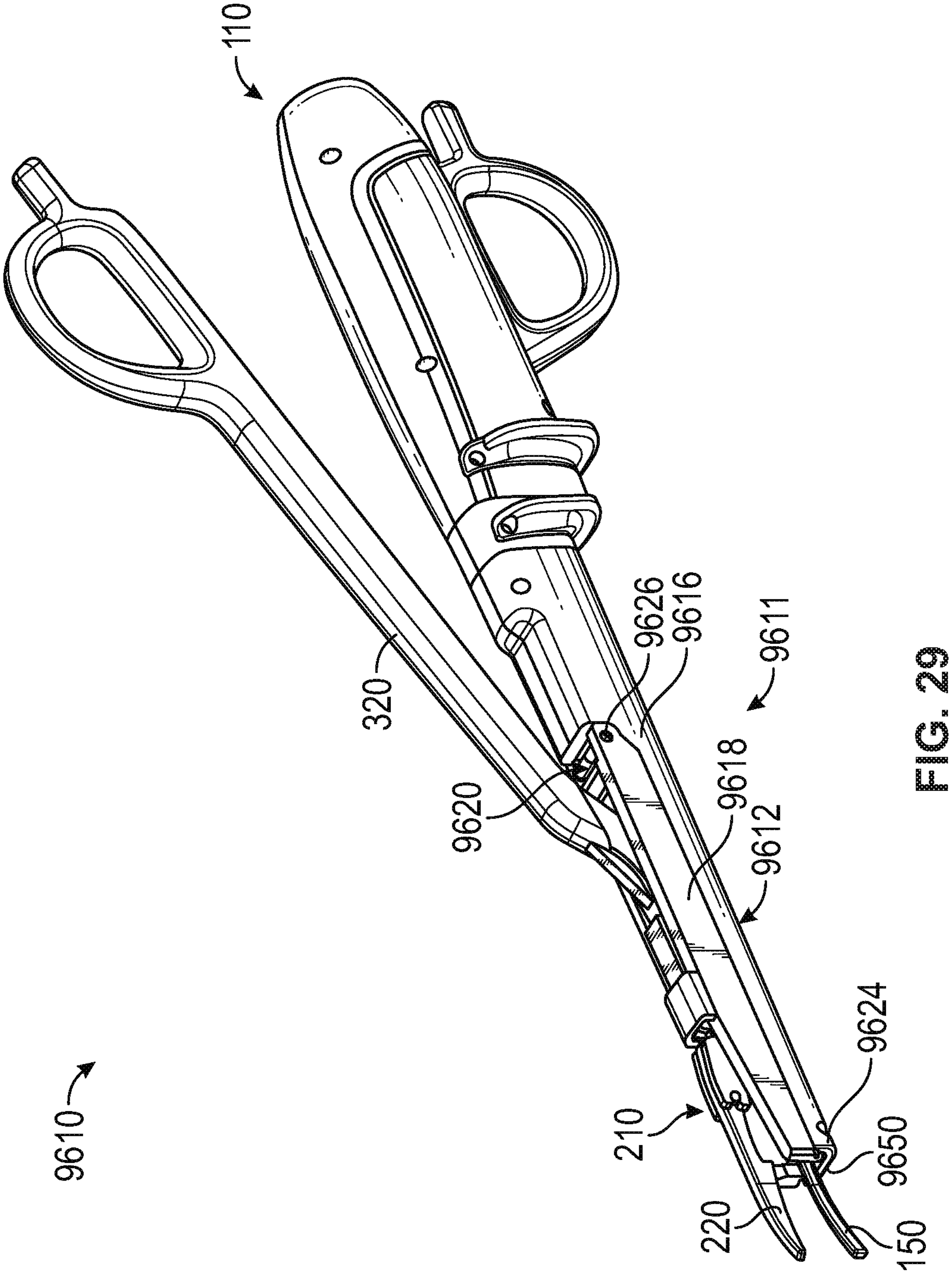
FIG. 29 depicts a perspective view of a fourth exemplary surgical instrument having a first accessible outer sheath with a detachable hinge cover.
Figure 30:
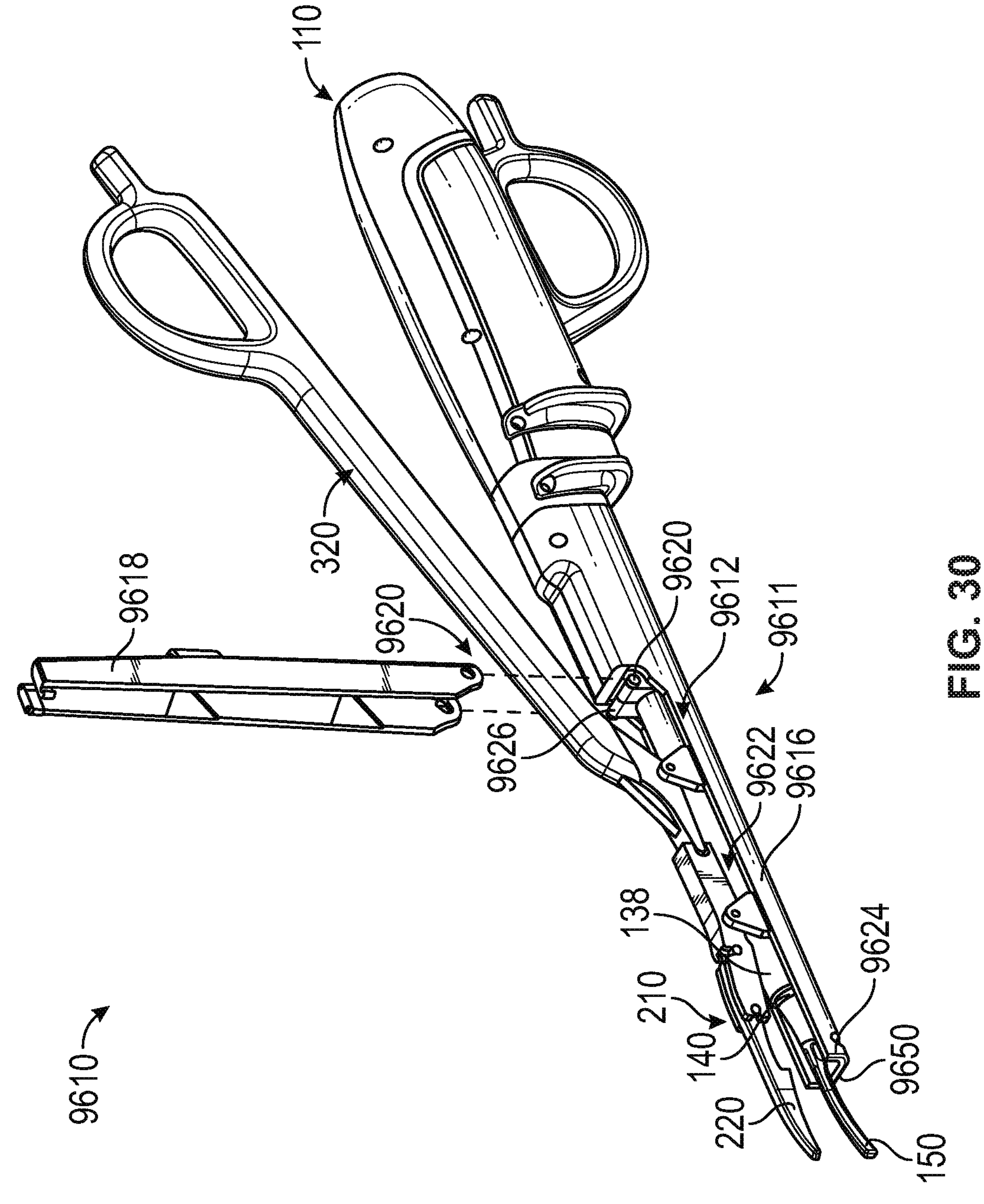
FIG. 30 depicts a partially exploded perspective view of the surgical instrument of FIG. 29.
Figure 31:
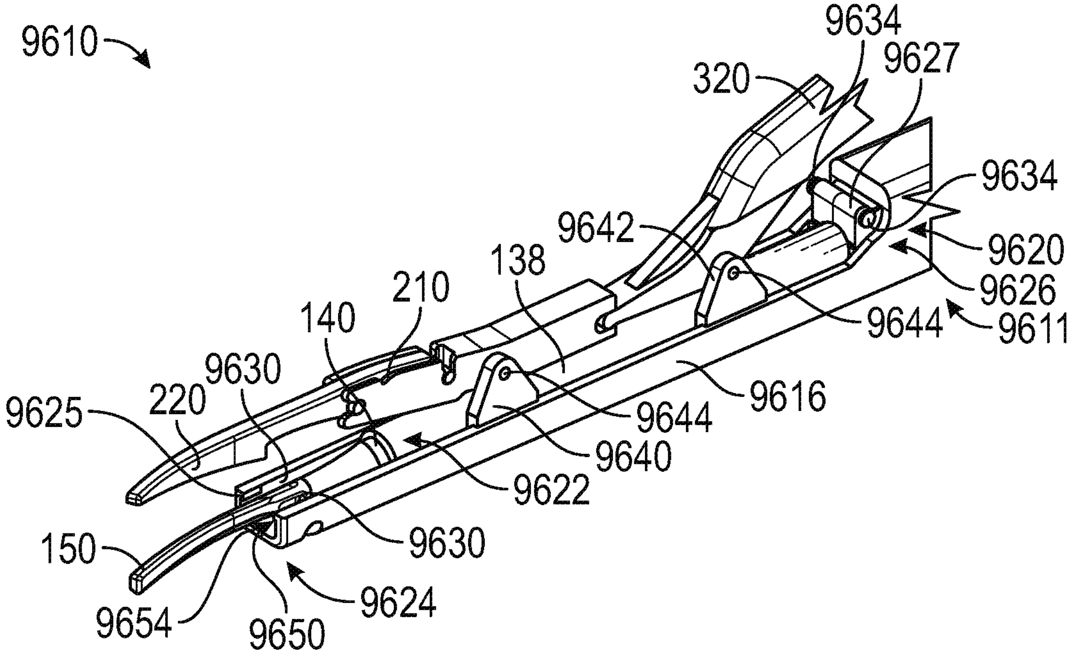
FIG. 31 depicts an enlarged perspective view of the surgical instrument of FIG. 30.

FIGS. 29-35C illustrate a fourth exemplary surgical instrument (9610) including a shaft assembly (9611) with a first accessible outer sheath (9612). Surgical instrument (9610) further includes handle assembly (110), clamp arm assembly (210) with clamp pad assembly (220), clamp arm actuator (320), and tube (138) through which waveguide (140) extends to ultrasonic blade (150) along the longitudinal axis. With respect to FIGS. 29-30, accessible outer sheath (9612) radially surrounds at least a portion of waveguide (140) about the longitudinal axis and includes a sheath body (9616), a hinge cover (9618), and a sheath securement (9620). Sheath body (9616) removably receives hinge cover (9618) thereagainst to define a generally U-shape, and sheath securement (9620) detachably couples hinge cover (9618) against sheath body (9616). During treatment, hinge cover (9618) generally remains in a covered configuration as shown in FIG. 29. The clinician selectively detaches hinge cover (9618) from sheath body (9616) as shown in FIGS. 30-31 for accessing an inner portion (9622) of surgical instrument (9610) about tube (138) as desired, such as for more easily cleaning and/or sterilizing inner portion (9622) following treatment of the patient.

Figure 32:
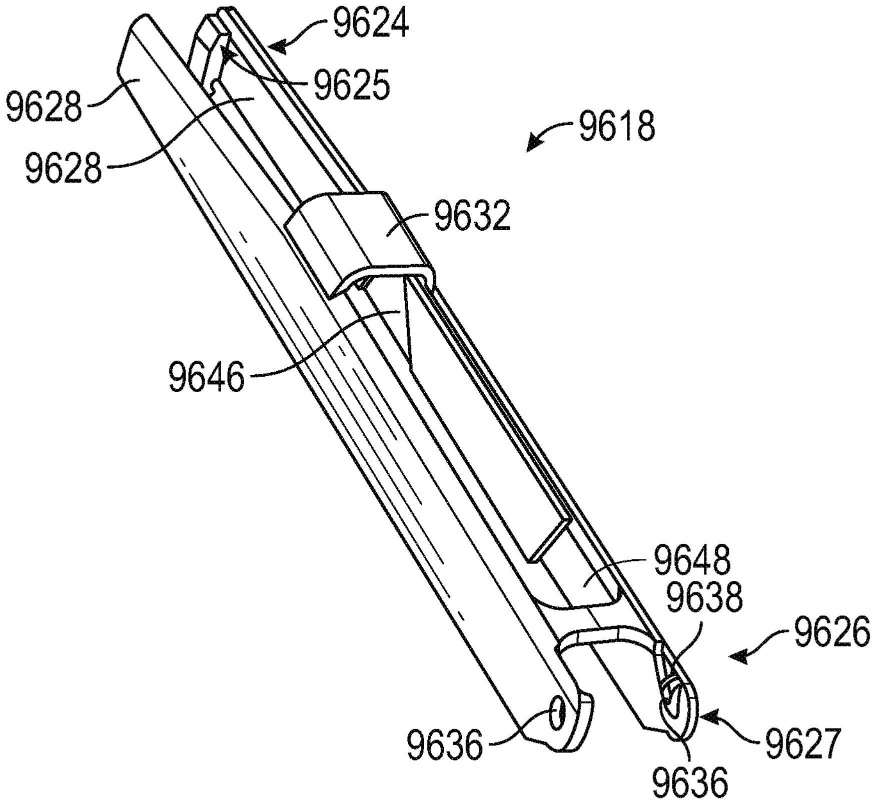
FIG. 32 depicts a perspective view of the hinge cover of FIG. 30.

FIG. 31 and FIG. 32 show sheath body (9616), hinge cover (9618), and sheath securement (9620) in greater detail. To this end, sheath securement (9620) includes a distal securement (9624) having a snap coupling (9625) and a proximal securement (9626) having a hinge coupling (9627). Snap coupling (9625) includes a pair of offset elongated resilient tabs (9628) configured to releasably engage a pair of shoulders (9630), respectively. In the present example, each elongated tab (9628) extends from hinge cover (9618), whereas shoulders (9630) are positioned on sheath body (9616). In order to accommodate inward resilient deflection for selectively disengagement from shoulders (9630), elongated tabs (9628) distally extend relative to a laterally extending buttress (9632), which provides structural support through hinge cover (9618).

Hinge coupling (9627) of proximal securement (9626) includes a pair of laterally extending and opposing pins (9634) configured to be pivotally received within a pair of bores (9636), respectively. In the present example, each pin (9635) extends laterally outward from sheath body (9616), whereas each bore (9636) extends through hinge cover (9618). Hinge cover (9618) generally pivots about pins (9635) relative to sheath body (9616), but is also fully removable from sheath body (9616) upon over rotation of hinge cover (9618) in the proximal direction. More particularly, a slot (9638) extends through an inner surface of hinge cover (9618) to each bore (9636). Thus, while each pin (9634) is generally captured in each bore (9636), each slot (9638) is configured to provide each pin (9634) with a path through which to travel for selective removal as discussed below in greater detail.

In addition, a distal mount (9640) and a proximal mount (9642) extend upward from each lateral side of sheath body (9612) adjacent to tube (138) within inner portion (9622). Distal and proximal mounts (9640, 9642) each have a lateral hole (9644) extending therethrough in order to pivotally mount clamp arm assembly (210) and clamp arm actuator (320) thereto. Hinge cover (9618) has a pair of distal mount recesses (9646) and a pair of proximal mount recesses (9648) configured to provide clearance for distal and proximal mounts (9640, 9642) along an inner surface of hinge cover (9618).

Figure 33A:
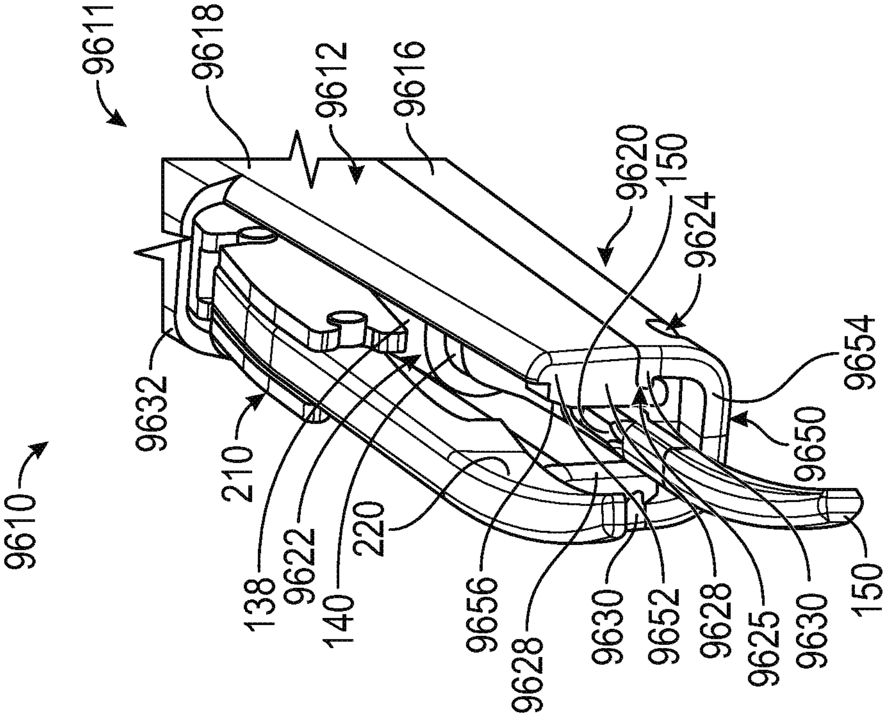
FIG. 33A depicts an enlarged perspective view of the surgical instrument of FIG. 29 with a clamp arm assembly in an opened position and the hinge cover in a covered configuration.
Figure 33B:
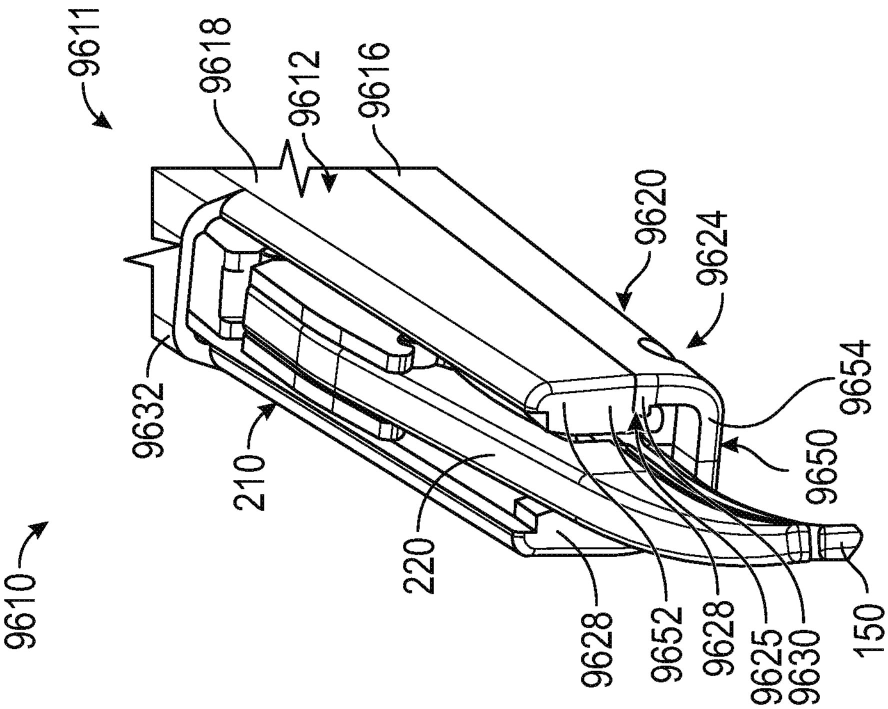
FIG. 33B depicts the enlarged perspective view of the surgical instrument similar to FIG. 33A, but showing the clamp arm assembly in the closed position.
Figure 33C:
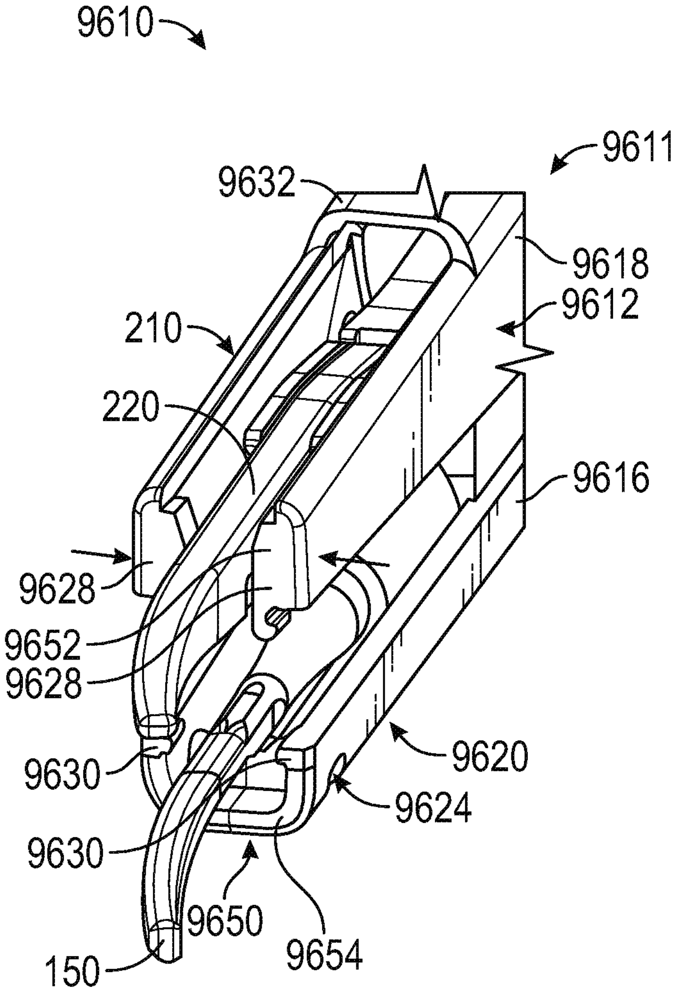
FIG. 33C depicts the enlarged perspective view of the surgical instrument similar to FIG. 33A, but showing the hinge cover being detached from the covered configuration.
Figure 34A:
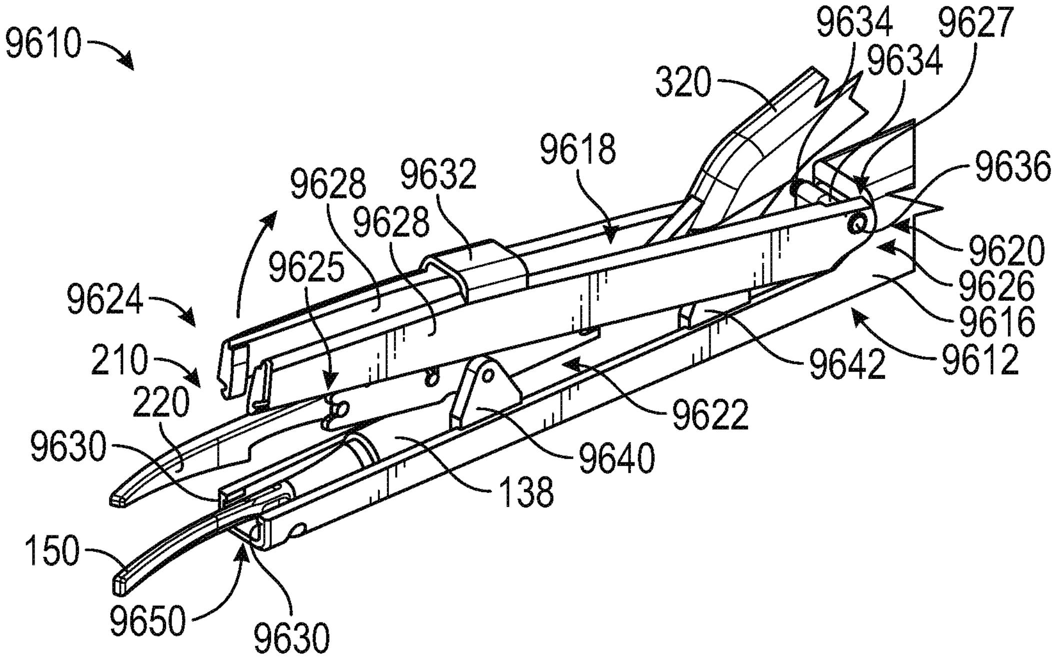
FIG. 34A depicts an enlarged perspective view of the surgical instrument of FIG. 29 with the hinge cover being detached from the covered configuration.
Figure 34B:
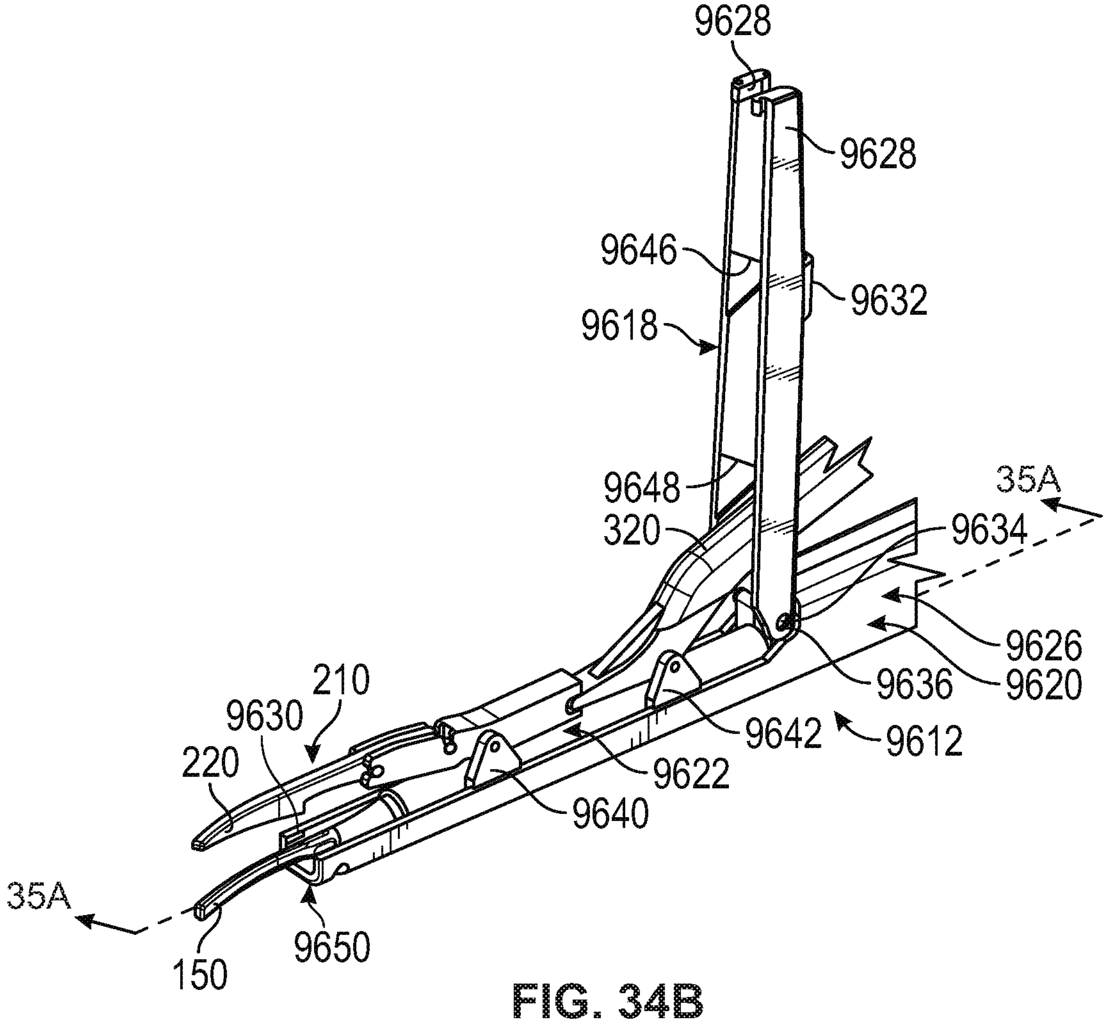
FIG. 34B depicts the enlarged perspective view of the surgical instrument similar to FIG. 34A with the hinge cover further detached from the covered configuration.

FIGS. 33A-33B show a distal tissue stop (9650) configured to inhibit tissue from being proximally introduced into inner portion (9622) of surgical instrument (9610) beyond distal tissue stop (9650). In the present example, an upper portion (9652) of distal tissue stop (9650) is a distal face of hinge cover (9618), whereas a lower portion (9654) of distal tissue stop (9650) is a distal face of sheath body (9616). Clamp pad assembly (220) is movably received within a clamp channel (9656) between lateral portions of distal tissue stop (9660) to thereby provide ample clearance to move clamp pad assembly (220) between open and closed positions as discussed above in greater detail.

Figure 35A:
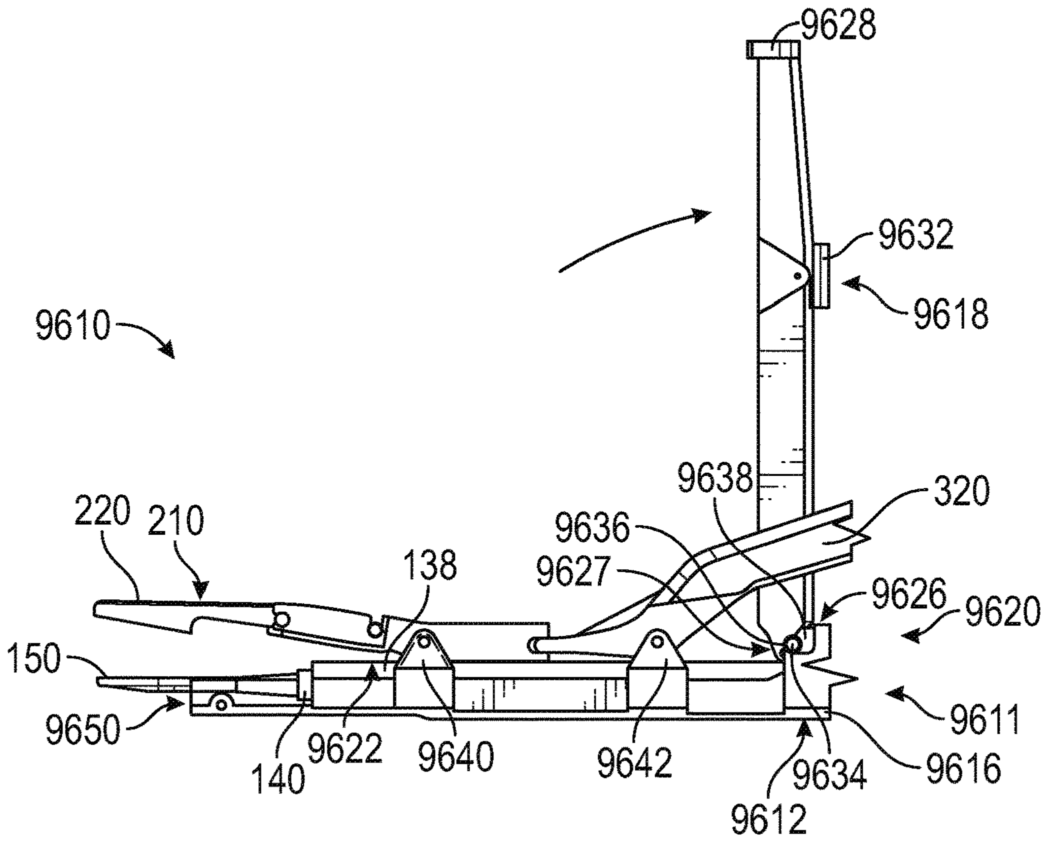
FIG. 35A depicts an enlarged cross-sectional view of the surgical instrument of FIG. 34B taken along section line 35A-35A of FIG. 34B with the hinge cover rotated to a transverse orientation.
Figure 35B:
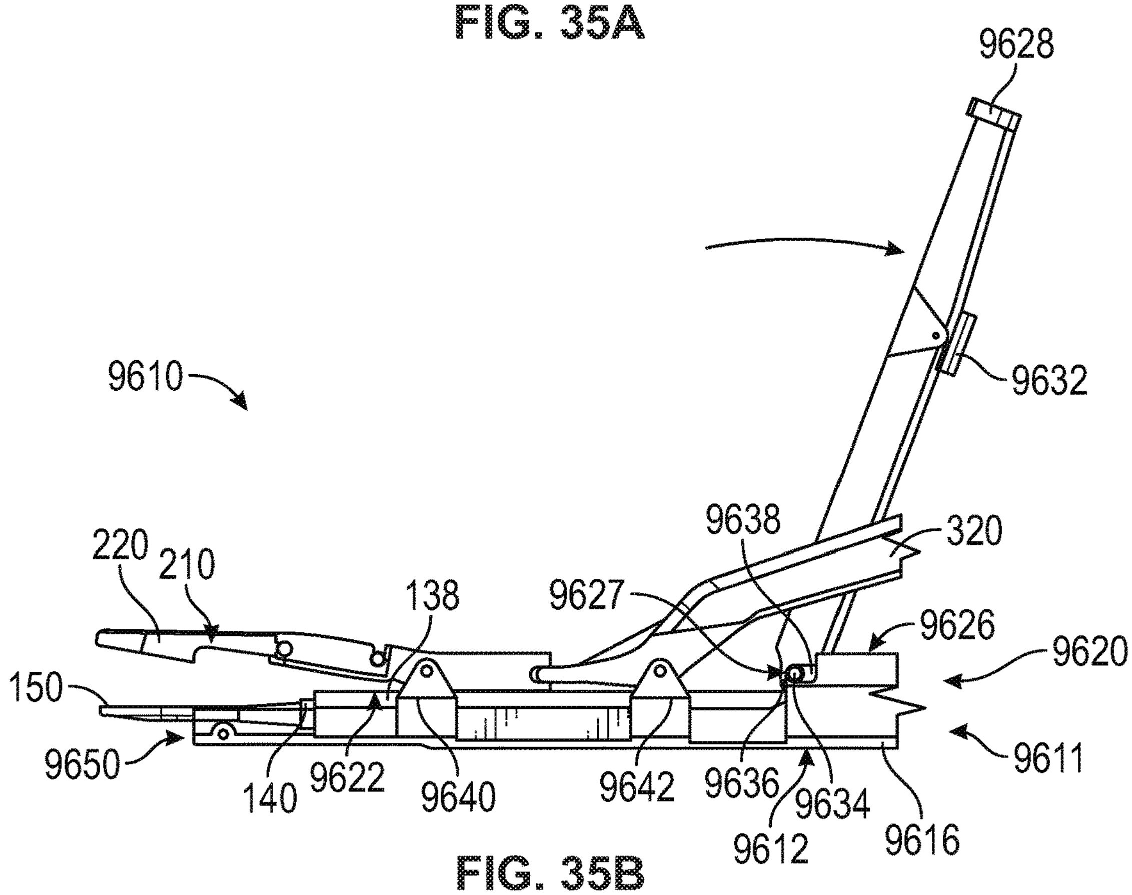
FIG. 35B depicts the enlarged cross-sectional view of the surgical instrument similar to FIG. 35A, but having the hinge cover over rotated beyond the transverse orientation for decoupling the hinge cover therefrom.
Figure 35C:
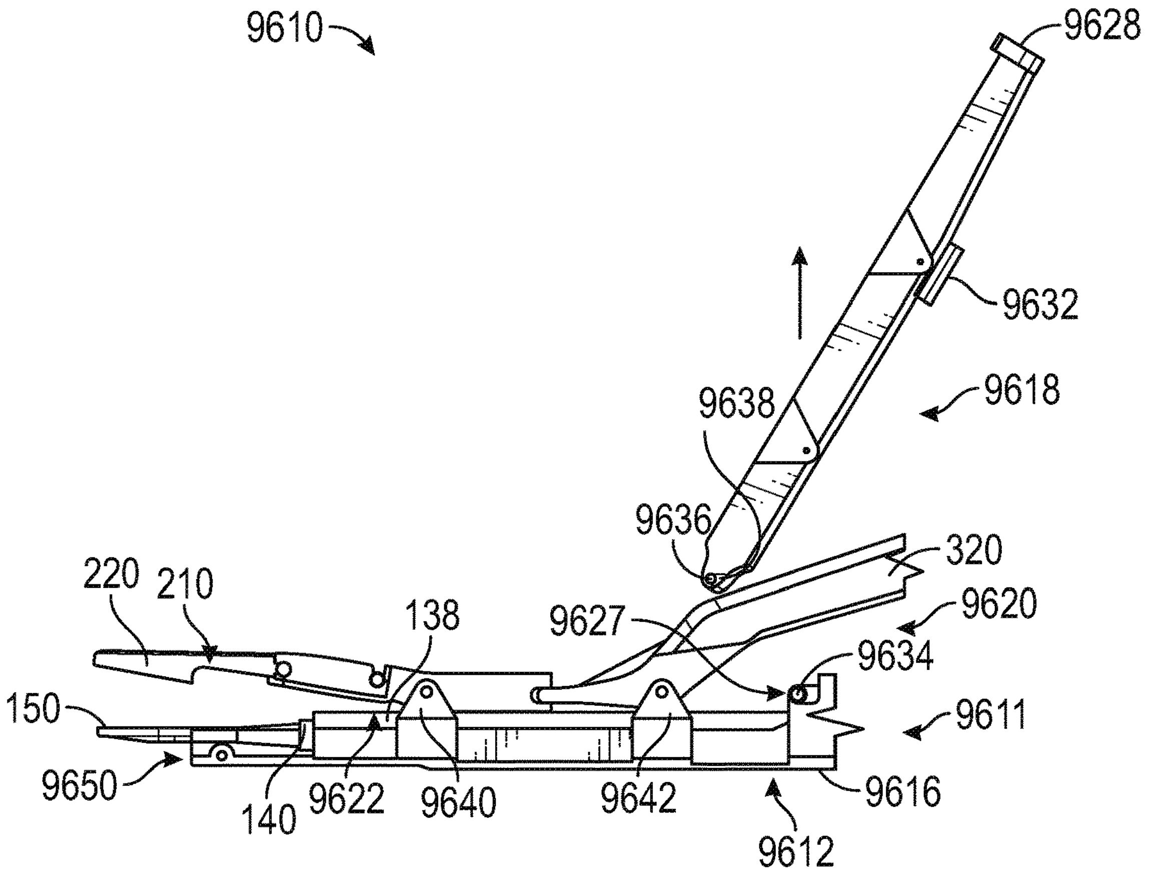
FIG. 35C depicts the enlarged cross-sectional view of the surgical instrument similar to FIG. 35B, but having the hinge cover decoupled therefrom.

In use, with respect to FIGS. 33A-35C, clinician accesses inner portion (9622) of surgical instrument (9610) by detaching hinge cover (9618) from sheath body (9616). More particularly, clinician selectively manipulates elongated tabs (9628) inward as shown in FIG. 33C through clamp channel (9656) until transversely clear of and disengaged from shoulders (9630). Once proximal securement (9626) is thereby disengaged, hinge cover (9618) proximally pivots from a longitudinal orientation to a transverse orientation as shown in FIGS. 34A-34B. Pins (9634) generally remain within bores (9636) during rotation from the longitudinal orientation of the covered configuration to the transverse orientation. However, as shown in FIGS. 35A-35C, over rotation of hinge cover (9618) proximally beyond the transverse orientation aligns slots (9638) respectively with pins (9634) such that hinge cover (9618) may be selectively removed from sheath body (9616) for accessing inner portion (9622). The clinician cleans surgical instrument (9610) using any one or more known cleaning methods for such instruments. Upon desirable cleaning, clinician reattaches hinge cover (9618) in generally the reverse order of detaching hinge cover (9618) as described above.

B. A Magnetic Cover for a Second Accessible Outer Sheath

Figure 36:
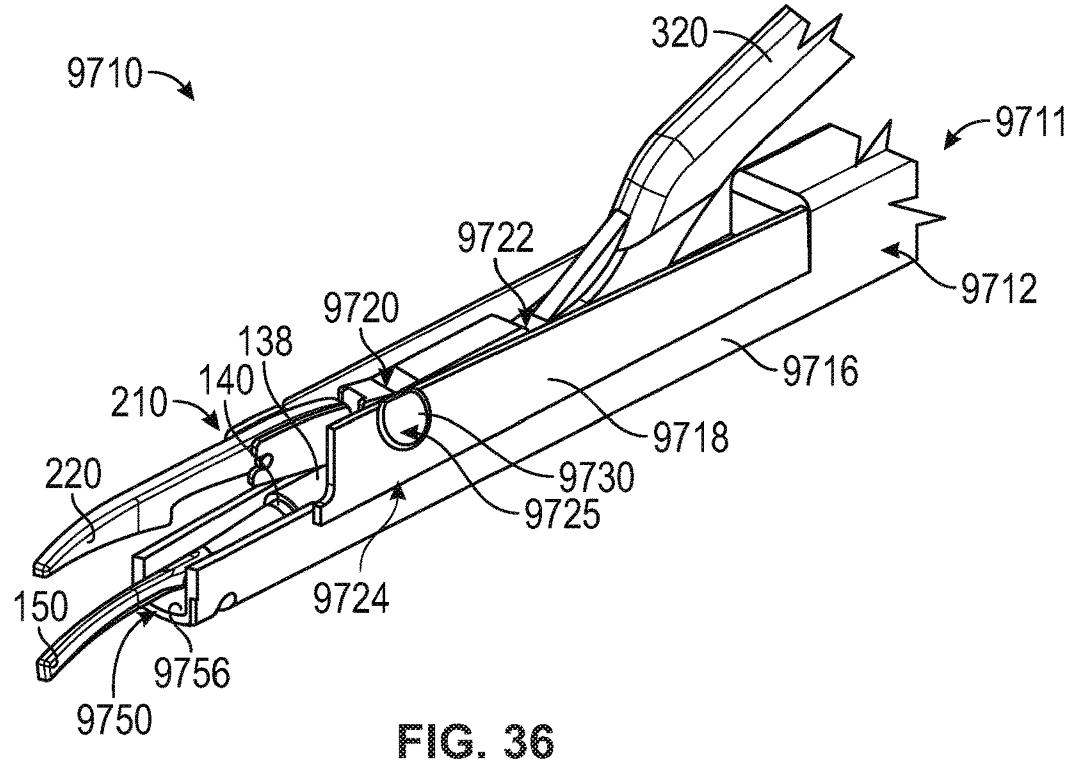
FIG. 36 depicts a perspective view of a fifth exemplary surgical instrument having a second accessible outer sheath with a detachable magnetic cover.
Figure 37:
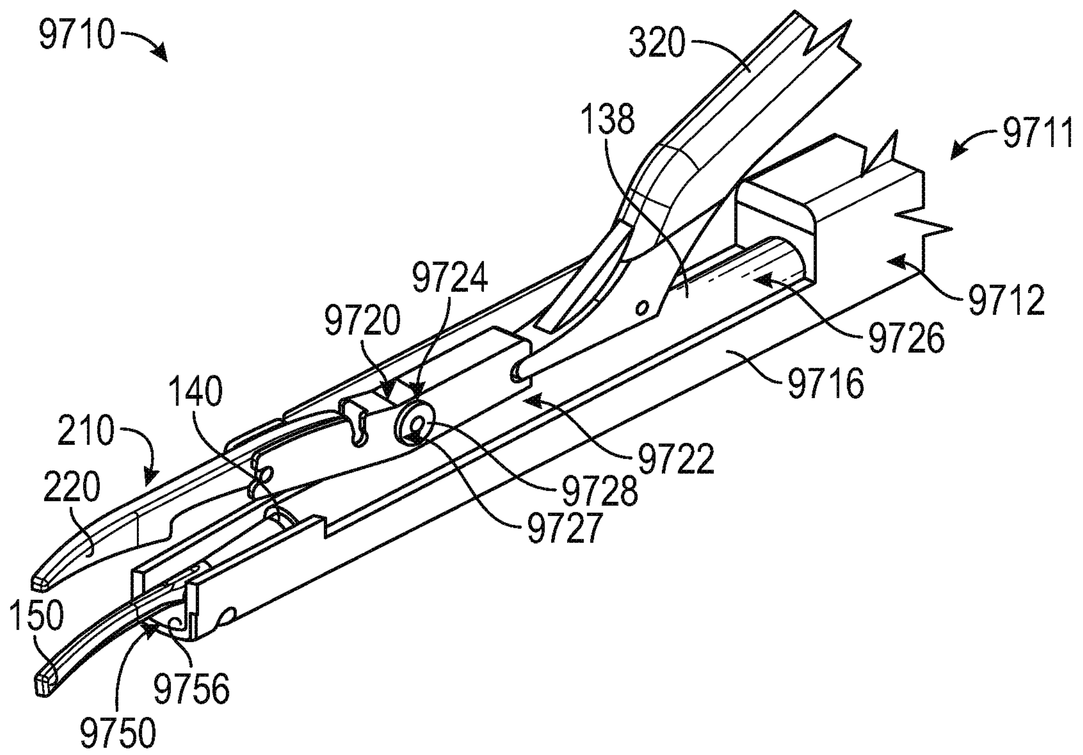
FIG. 37 depicts an enlarged perspective view of the surgical instrument of FIG. 36 with the magnetic cover decoupled therefrom.

FIGS. 36-39B illustrate a fifth exemplary surgical instrument (9710) including a shaft assembly (9711) with a second accessible outer sheath (9712). With respect to FIGS. 36-37, accessible outer sheath (9712) radially surrounds at least a portion of waveguide (140) about the longitudinal axis and includes a sheath body (9716), a magnetic cover (9718), and a sheath securement (9720). Sheath body (9716) removably receives magnetic cover (9718) thereagainst to define a generally U-shape, and sheath securement (9720) detachably couples magnetic cover (9718) against sheath body (9716). During treatment, magnetic cover (9718) generally remains in a covered configuration as shown in FIG. 36. The clinician selectively detaches magnetic cover (9718) from sheath body (9716) as shown in FIG. 37 for accessing an inner portion (9722) of surgical instrument (9710) about tube (138) as desired, such as for more easily cleaning and/or sterilizing inner portion (9722) following treatment of the patient.

Figure 38:
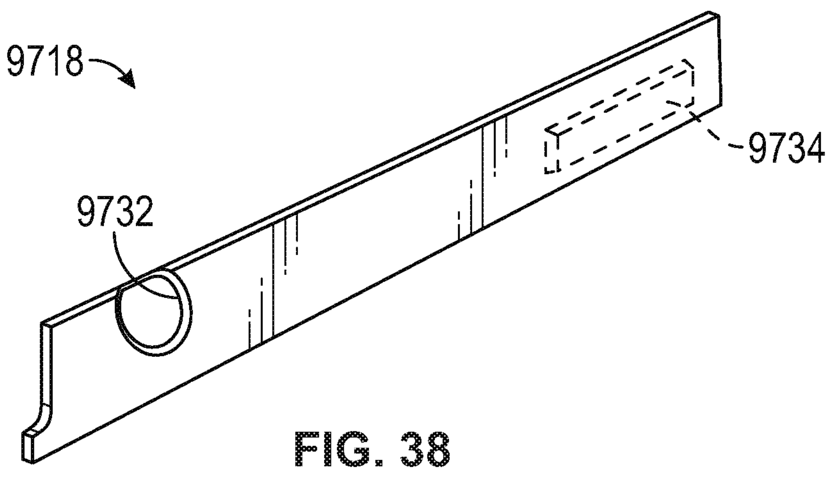
FIG. 38 depicts a perspective view of the magnetic cover of FIG. 36.

FIGS. 36-38 show sheath body (9716), magnetic cover (9718), and sheath securement (9720) in greater detail. To this end, sheath securement (9720) includes a distal securement (9724) having a distal magnetic coupling (9725) and a proximal securement (9726) having a proximal magnetic coupling (9727). Distal magnetic coupling (9725) includes a magnetically attractive base (9728) secured to clamp arm assembly (210) and a magnetic coupler, such as a disc magnet (9730), configured to a positioned opposite of base (9728). Thereby, disc magnet (9730), while magnetically attracted to base (9728) in proximity of base (9728) sandwiches magnetic cover (9718) therebetween. Magnetic cover (9718) further includes a cylindrical recess (9732) configured to receive disc magnet (9730) to both increase magnetic attraction of disc magnet (9730) to base (9728) as well as position disc magnet (9730) relatively flush with an outer surface thereon. In the present example, disc magnet (9730) is fixed within cylindrical recess (9732) and base (9728) is a metallic material configured to attract disc magnet (9730). Alternatively, base (9728) may be magnetic for increased securement with disc magnet (9730).

Proximal magnetic coupling (9727) of proximal securement (9726) includes an inner magnet (9734) secured to an inner surface of magnetic cover (9718) and extending inward toward tube (138). Tube (138) is magnetically attractive such that inner magnet (9734) is configured to engage tube (138) for removably coupling magnetic cover (9718) to tube (138). In the present example, tube (138) is a metallic material configured to attract inner magnet (9734). Alternatively, tube (138) may be magnetic or having a magnet thereon for increased securement with inner magnet (9734).

In addition, distal mount (9640) (see FIG. 31) and proximal mount (9642) (see FIG. 31) extend upward from sheath body (9712) adjacent to tube (138) and opposite from magnetic cover (9718). Distal and proximal mounts (9640, 9642) (see FIG. 31) are generally similar to those discussed above. However, rather than having such mounts (9640, 9642) (see FIG. 31) on each lateral side, mounts (9640, 9642) (see FIG. 31) are on the one side opposite from magnetic cover (9718) to thereby pivotally support clamp arm assembly (210) and clamp arm actuator (320) for use.

Figure 39A:
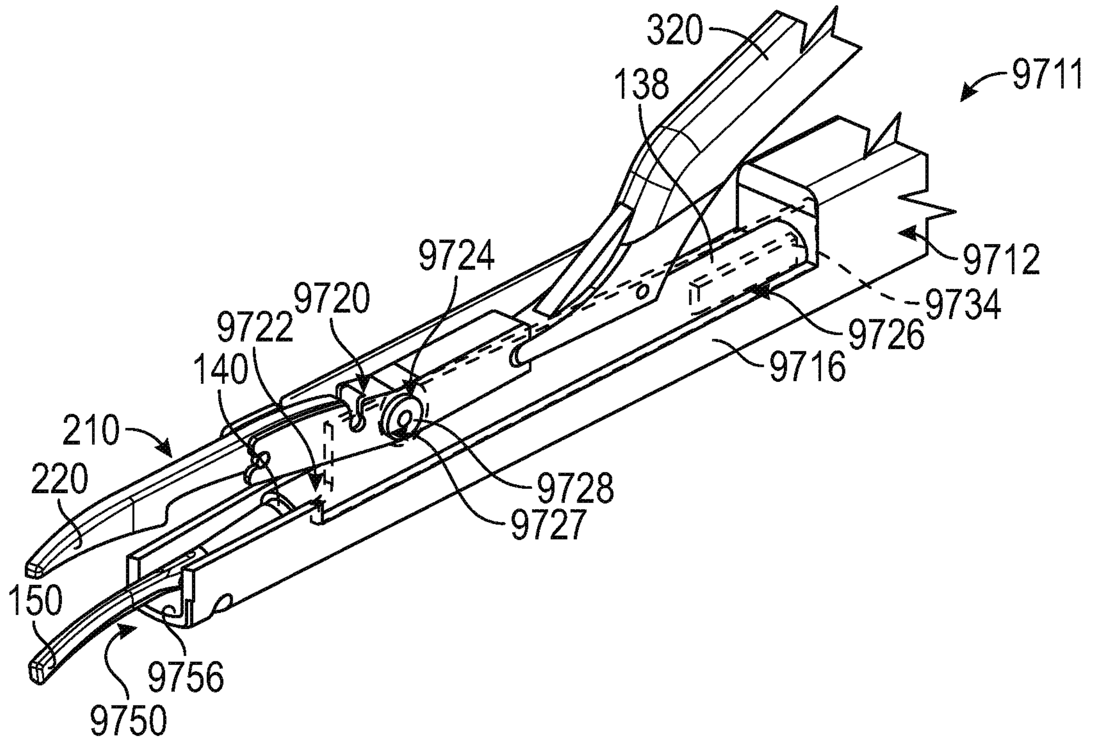
FIG. 39A depicts an enlarged perspective view of the surgical instrument of FIG. 36 with the magnetic cover hidden for greater clarity of various features.

FIG. 39A shows a distal tissue stop (9750) configured to inhibit tissue from being proximally introduced into inner portion (9722) of surgical instrument (9710) beyond distal tissue stop (9750). In the present example, distal tissue stop (9750) is a distal face of sheath body (9716). Clamp pad assembly (220) is movably received within a clamp channel (9756) between lateral portions of distal tissue stop (9760)

to thereby provide ample clearance to move clamp pad assembly (220) between open and closed positions as discussed above in greater detail.

Figure 39B:
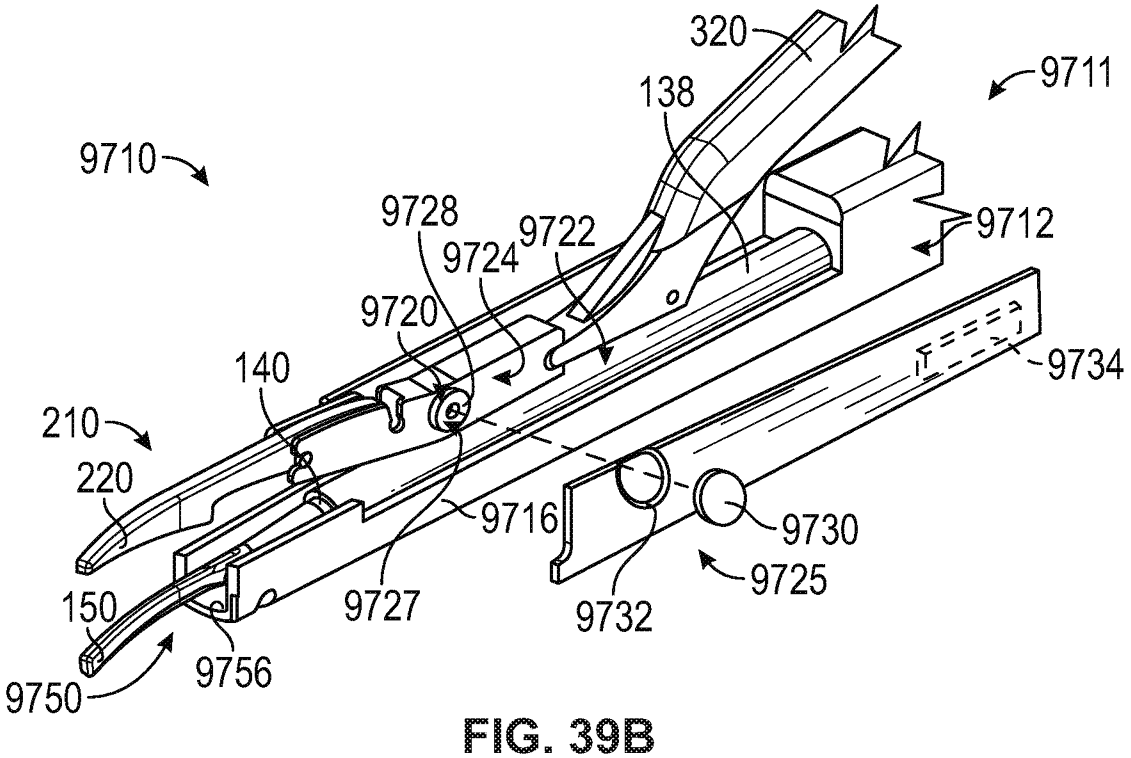
FIG. 39B depicts the enlarged perspective view of the surgical instrument similar to FIG. 39A, but showing the magnetic cover being decoupled therefrom.

In use, with respect to FIGS. 39A-39B, clinician accesses inner portion (9722) of surgical instrument (9710) by detaching magnetic cover (9718) from sheath body (9716). More particularly, clinician outwardly pulls on magnetic cover (9718) with sufficient force to overcome the magnetic attraction between disc magnet (9730) and base (9728) as well as between inner magnet (9734) and tube (138). Once distal and proximal securements (9724, 9726) are thereby disengaged, magnetic cover (9718) is simply removed from sheath body (9716) for accessing inner portion (9722). The clinician cleans surgical instrument (9710) using any one or more known cleaning methods for such instruments. Upon desirable cleaning, clinician reattaches magnetic cover (9718) in generally the reverse order of detaching magnetic cover (9718) as described above. In addition, clinician sterilizes surgical instrument (9710) following reattachment of magnetic cover (9718).

C. A Pin Cover for a Third Accessible Outer Sheath

Figure 40:
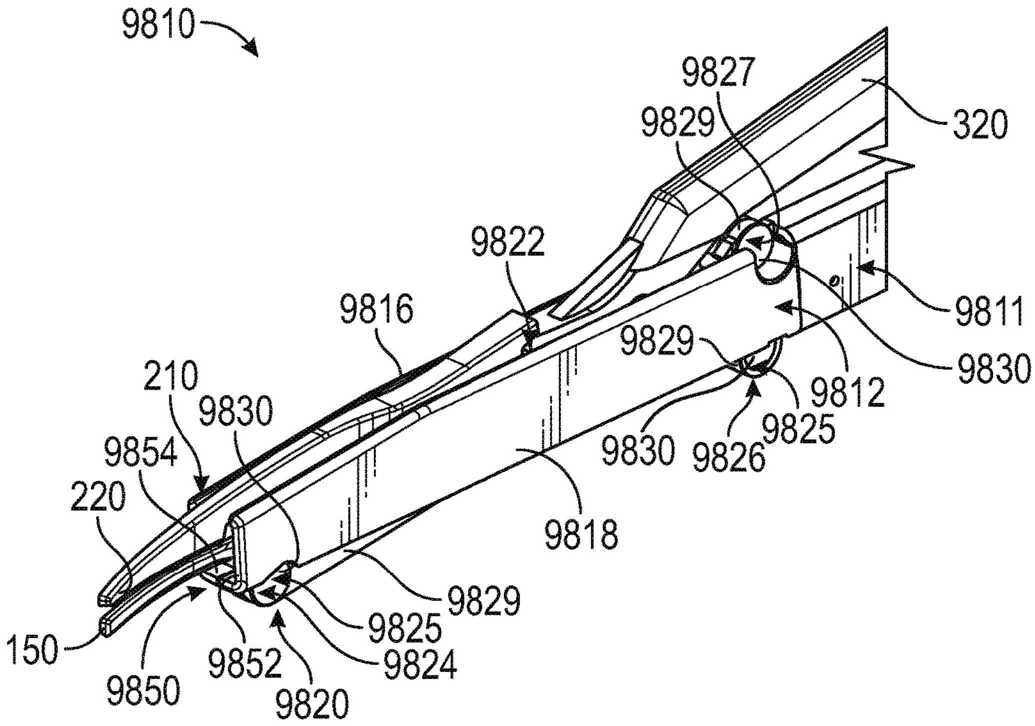
FIG. 40 depicts a perspective view of a sixth exemplary surgical instrument having a third accessible outer sheath with a detachable pin cover.
Figure 41:
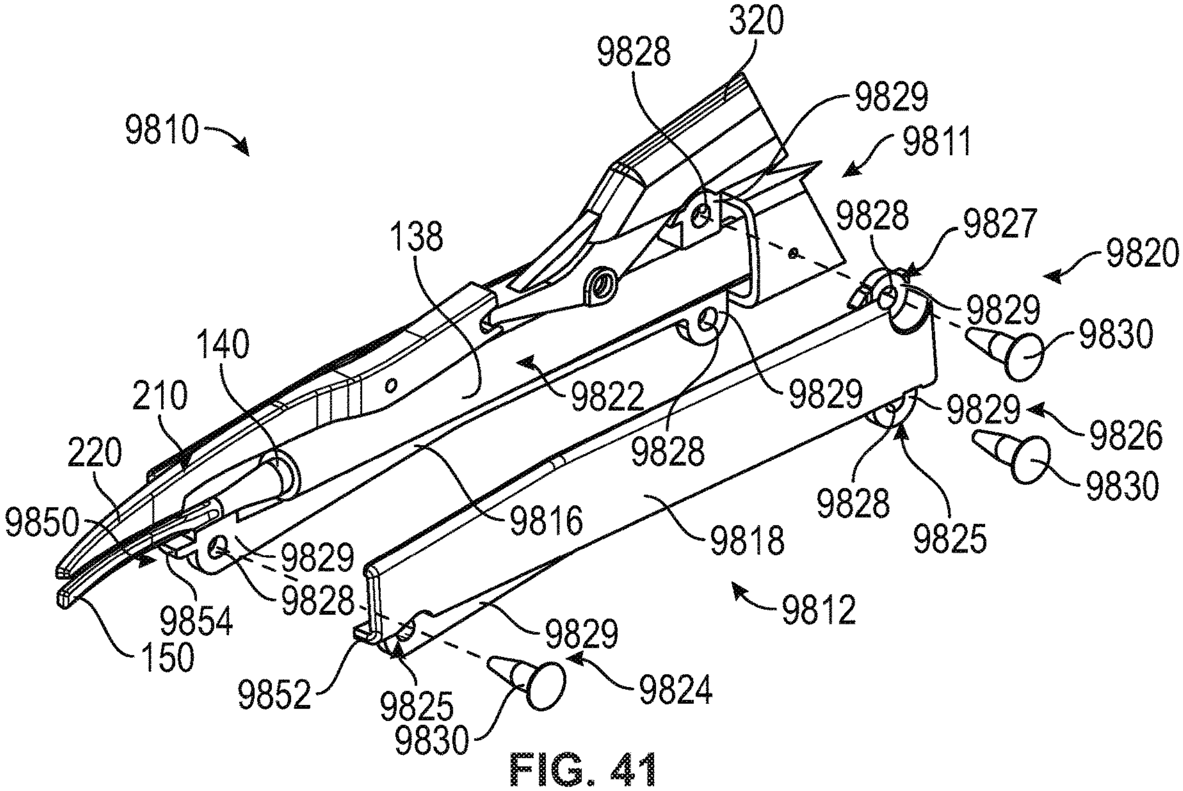
FIG. 41 depicts an enlarged partially exploded perspective view of the surgical instrument of FIG. 40 that includes the pin cover, which has a cover body and a plurality of pins.

FIGS. 40-41 illustrate a sixth exemplary surgical instrument (9810) including a shaft assembly (9811) with a third accessible outer sheath (9812). Accessible outer sheath (9812) radially surrounds at least a portion of waveguide (140) about the longitudinal axis and includes a sheath body (9816), a pin cover (9818), and a sheath securement (9820). Sheath body (9816) removably receives pin cover (9818) thereagainst to define a generally U-shape, and sheath securement (9820) detachably couples pin cover (9818) against sheath body (9816). During treatment, pin cover (9818) generally remains in a covered configuration as shown in FIG. 40. The clinician selectively detaches pin cover (9818) from sheath body (9816) as shown in FIG. 41 for accessing an inner portion (9822) of surgical instrument (9810) about tube (138) as desired, such as for more easily cleaning and/or sterilizing inner portion (9822) following treatment of the patient.

Sheath securement (9820) includes a distal securement (9824) having a lower pin coupling (9825) and a proximal securement (9826) having another lower pin coupling (9825) and an upper pin coupling (9827). Each of lower and upper pin coupling (9825, 9827) includes a pin hole (9828) extending laterally through a mounting flange (9829) and a pin (9830). More particularly, sheath body (9816) and pin cover (9818) have a pair of cooperating pin holes (9828) through mounting flange (9829) for each lower and upper pin coupling (9825, 9827). Pin (9838) is configured to be received the cooperating pair of pin holes (9828) while coaxially aligned for removably attaching pin cover (9818) to sheath body (9816). In the present example, pin (9838) is configured to frictionally engaged mounting flange (9829) within pin hole (9828) for securement. Of course, engagement, such as other fasteners, may be similarly used. The invention is thus not intended to be unnecessarily limited to frictionally engaged pins (9830).

In addition, distal mount (9640) (see FIG. 31) and proximal mount (9642) (see FIG. 31) extend upward from sheath body (9812) adjacent to tube (138) and opposite from pin cover (9818). Distal and proximal mounts (9640, 9642) (see FIG. 31) are generally similar to those discussed above. However, rather than have such mounts (9640, 9642) (see FIG. 31) on each lateral side, mounts (9640, 9642) (see FIG. 31) are on the one side opposite from pin cover (9818) to thereby pivotally support clamp arm assembly (210) and clamp arm actuator (320) for use.

Accessible outer sheath (9812) also has a distal tissue stop (9850) configured to inhibit tissue from being proximally introduced into inner portion (9822) of surgical instrument (9810) beyond distal tissue stop (9850). In the present example, one lateral portion (9852) of distal tissue stop (9850) is a distal face of pin cover (9818), whereas another lateral portion (9854) of distal tissue stop (9850) is a distal face of sheath body (9816). Clamp pad assembly (220) is movably received within a clamp channel (9856) between lateral portions (9852, 9854) of distal tissue stop (9860) to thereby provide ample clearance to move clamp pad assembly (220) between open and closed positions as discussed above in greater detail.

In use, with respect to FIGS. 40-41, clinician accesses inner portion (9822) of surgical instrument (9810) by detaching pin cover (9818) from sheath body (9816). More particularly, clinician selectively withdraws pins (9830) from each pin hole (9828) for each of distal and proximal securements (9824, 9826). Once distal and proximal securements (9825, 9826) are thereby disengaged, pin cover (9818) is simply removed from sheath body (9816) for accessing inner portion (9822). The clinician cleans surgical instrument (9810) using any one or more known cleaning methods for such instruments. Upon desirable cleaning, clinician reattaches pin cover (9818) in generally the reverse order of detaching pin cover (9818) as described above. In addition, clinician sterilizes surgical instrument (9810) following reattachment of pin cover (9818).

D. A First Snap Cover for a Fourth Accessible Outer Sheath

Figure 42:
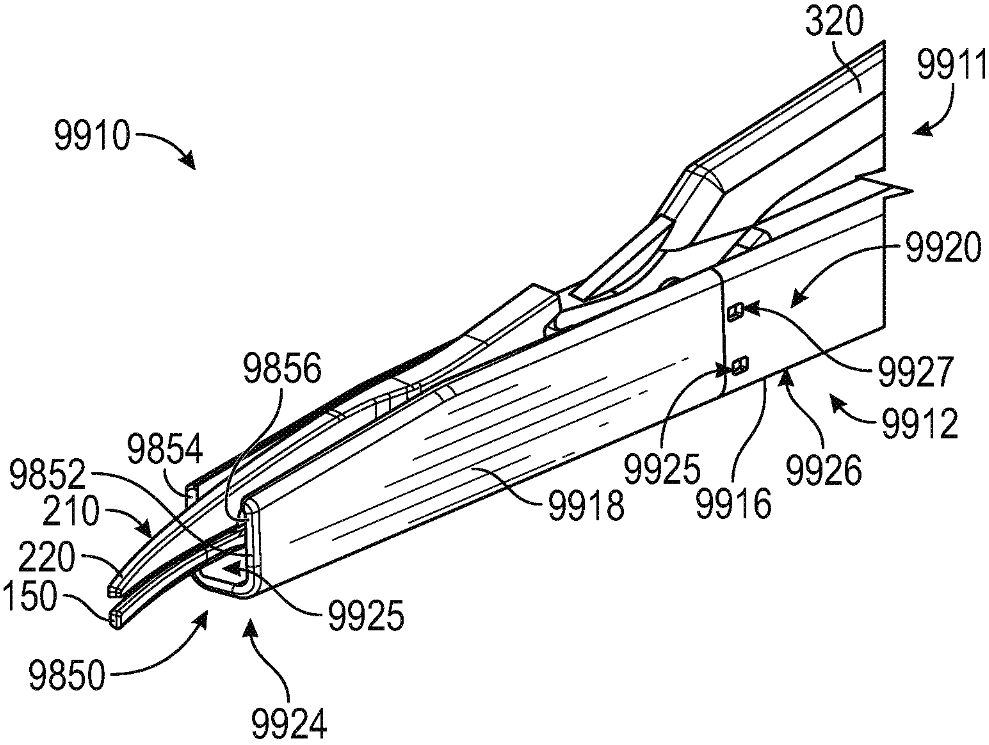
FIG. 42 depicts a perspective view of a seventh exemplary surgical instrument having a fourth accessible outer sheath with a detachable first snap cover.
Figure 43:
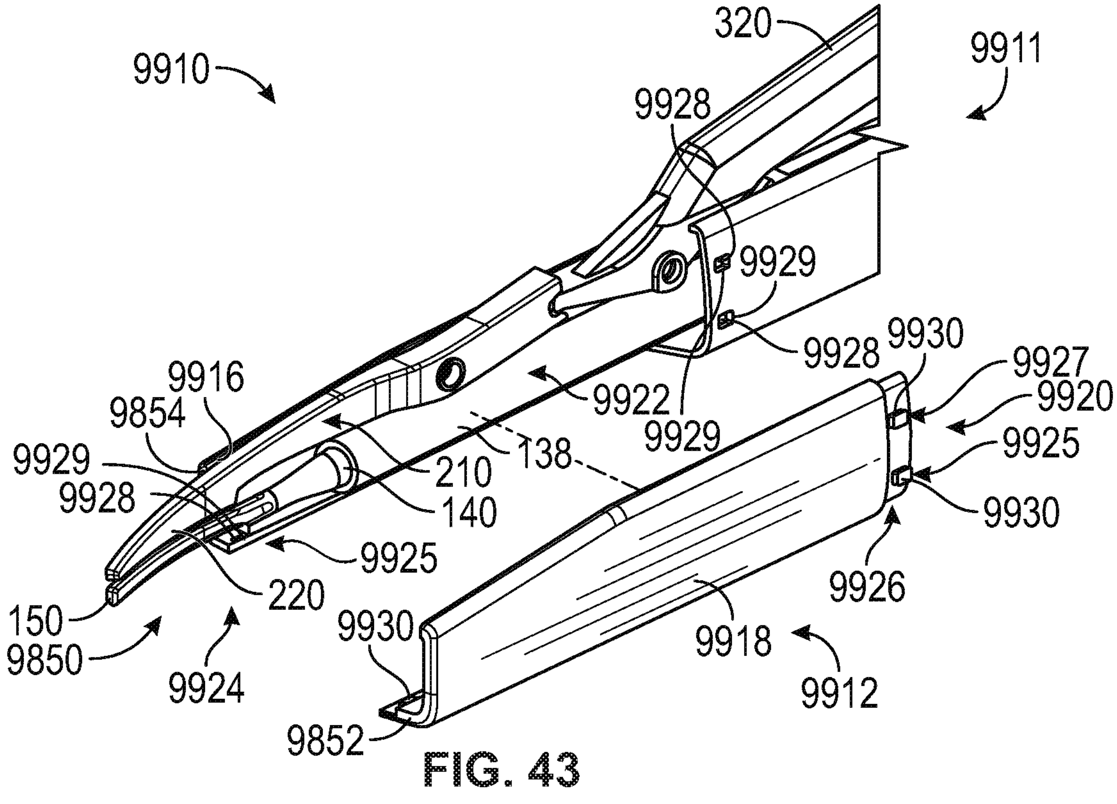
FIG. 43 depicts an enlarged partially exploded perspective view of the surgical instrument of FIG. 42.

FIGS. 42-46 illustrate a seventh exemplary surgical instrument (9910) including a shaft assembly (9911) with a fourth accessible outer sheath (9912). With respect to FIG. 42 and FIG. 43, accessible outer sheath (9912) radially surrounds at least a portion of waveguide (140) about the longitudinal axis and includes a sheath body (9916), a first snap cover (9918), and a sheath securement (9920). Sheath body (9916) removably receives snap cover (9918) thereagainst to define a generally U-shape, and sheath securement (9920) detachably couples snap cover (9918) against sheath body (9916). During treatment, snap cover (9918) generally remains in a covered configuration as shown in FIG. 42. The clinician selectively detaches snap cover (9918) from sheath body (9916) as shown in FIG. 43 for accessing an inner portion (9922) of surgical instrument (9910) about tube (138) as desired, such as for more easily cleaning and/or sterilizing inner portion (9922) following treatment of the patient.

Figure 44:
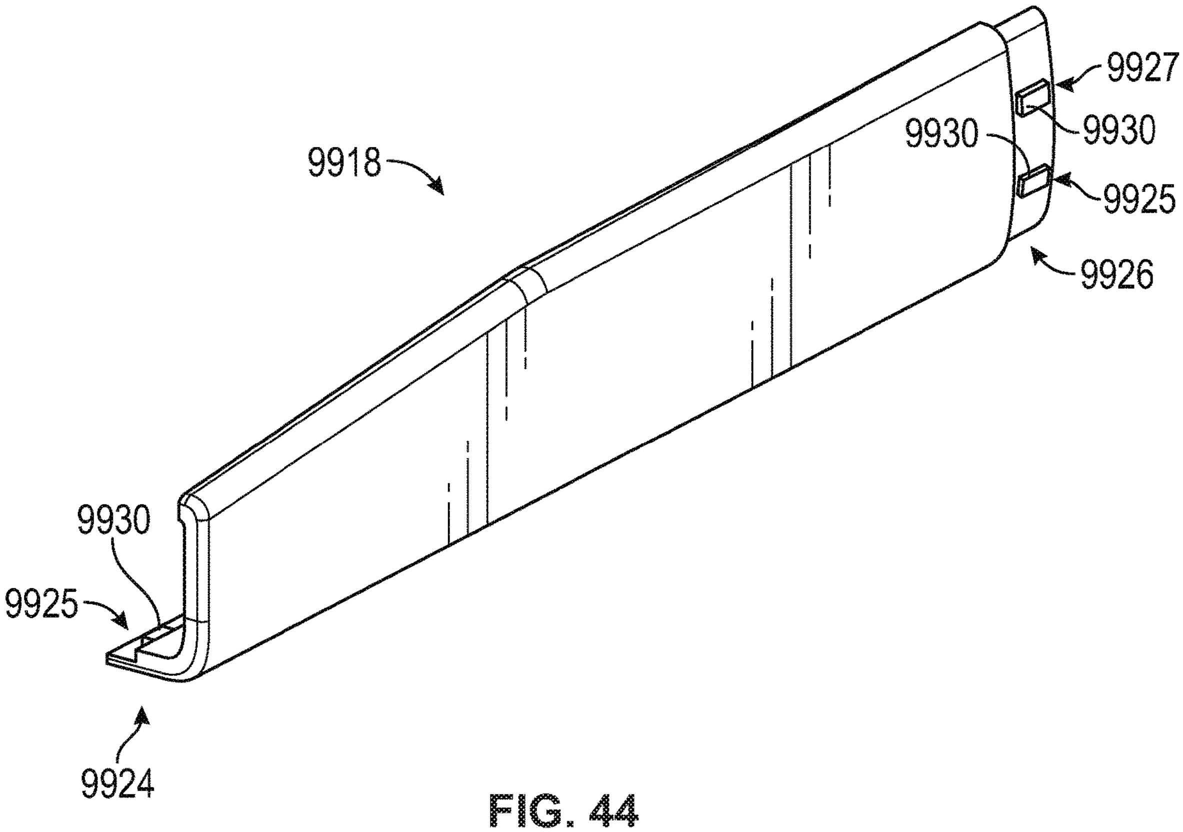
FIG. 44 depicts an exterior perspective view of the snap cover of FIG. 43.
Figure 45:
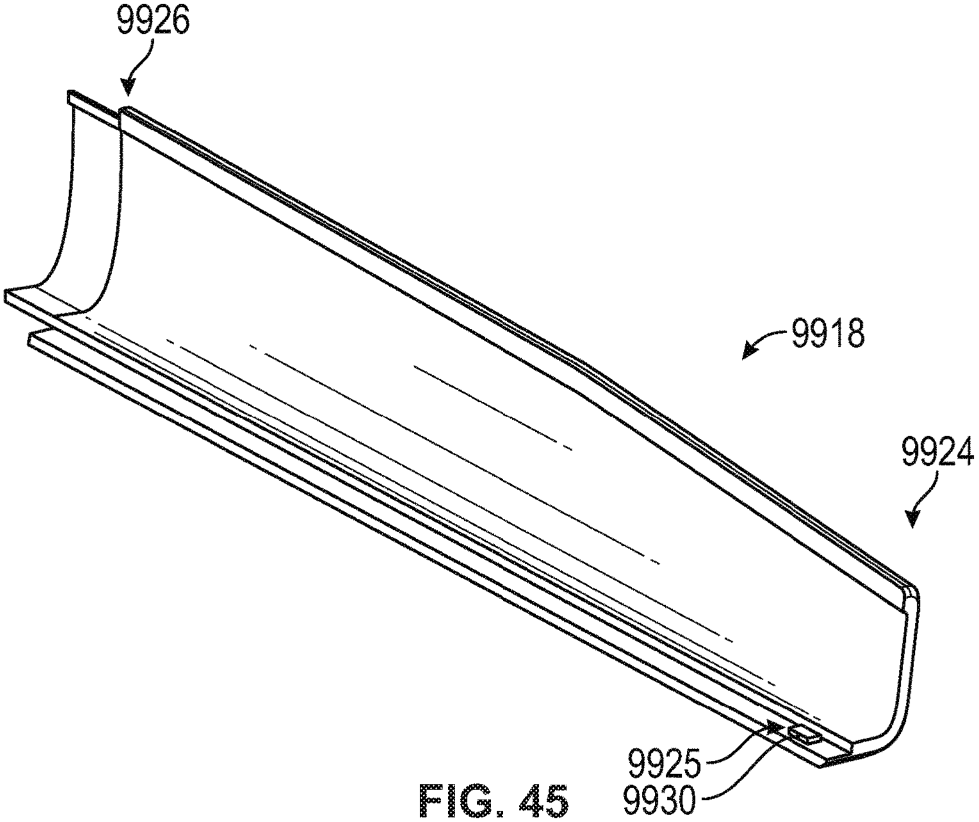
FIG. 45 depicts an interior perspective view of the snap cover of FIG. 43.

Sheath securement (9920) includes a distal securement (9924) having a lower snap coupling (9925) and a proximal securement (9926) having another lower snap coupling (9925) and an upper snap coupling (9927). Each of lower and upper snap coupling (9925, 9927) includes a snap hole (9928) extending through sheath body (9916) to define at least one adjacent shoulder (9929) thereon and a resilient tab (9930), which extends from snap cover (9918). Each resilient tab (9930) is configured to extend through snap hole (9928) to releasably engage shoulder (9929). As shown in FIGS. 43-45, snap hole (9928) of distal securement (9924) extends transversely through sheath body (9916) to receive resilient tab (9930) of distal securement (9924), which extends transversely upward from an inner surface of snap cover (9918). In contrast, upper and lower snap holes (9928) of proximal securement (9926) extend laterally through sheath body (9916) to respectively receive upper and lower resilient tabs (9930) of proximal securement (9926), which extend laterally outward an outer surface of snap cover (9918).

Figure 46:
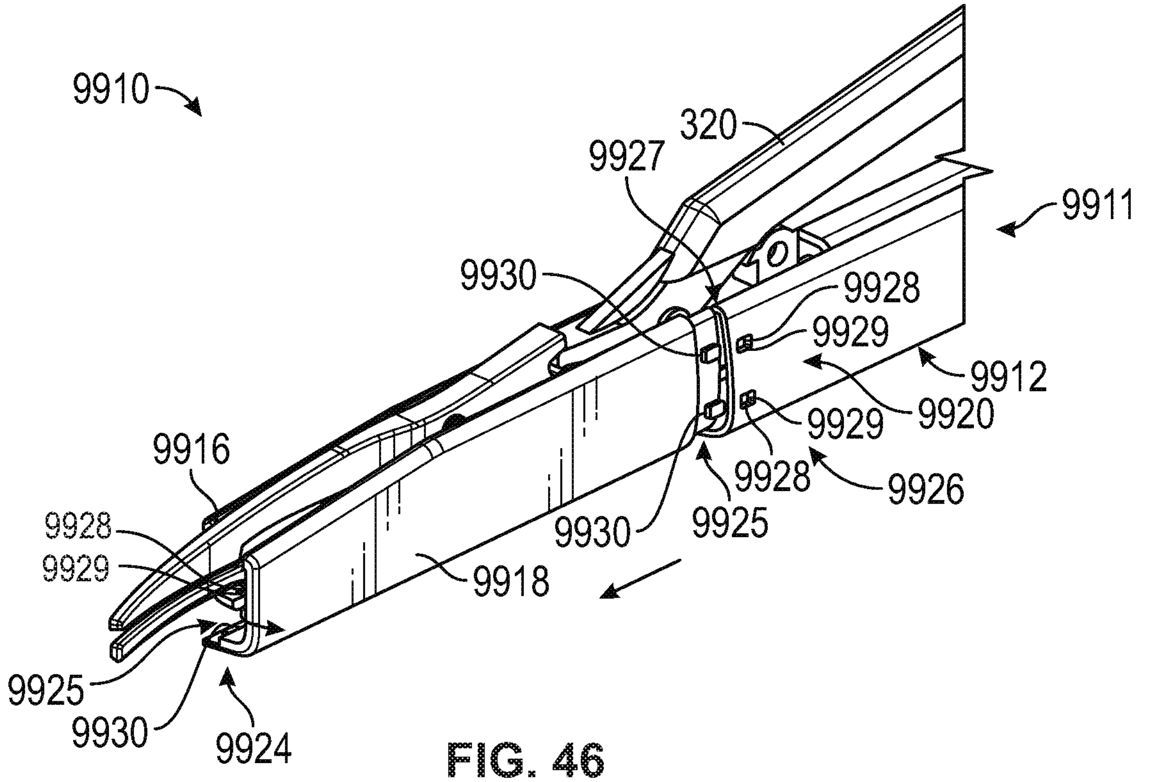
FIG. 46 depicts an enlarged perspective view of the surgical instrument of FIG. 42 with the snap cover being detached therefrom.
Figure 47:
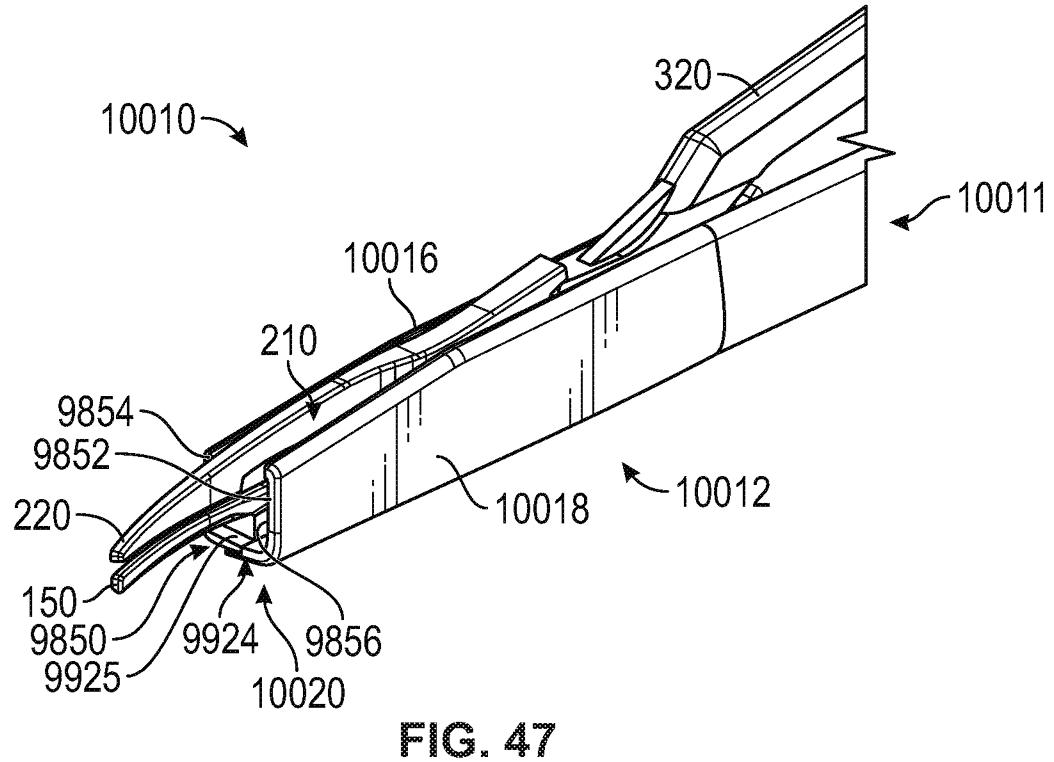
FIG. 47 depicts a perspective view of an eighth exemplary surgical instrument having a fifth accessible outer sheath with a detachable second snap cover.

In use, with respect to FIG. 46, clinician accesses inner portion (9922) of surgical instrument (9910) by detaching snap cover (9918) from sheath body (9916). More particularly, clinician selectively pivots a distal portion of snap cover (9918) laterally outward to overcome the resilient engagement between resilient tab (9930) and shoulder (9929) of distal securement (9924). Once distal securement is disengaged, clinician distally withdraws snap cover (9918) to overcome the resilient engagement between resilient tab (9930) and shoulder (9929) of proximal securement (9926) for removal of snap cover (9918) and access to inner portion (9922). The clinician cleans surgical instrument (9910) using any one or more known cleaning methods for such instruments. Upon desirable cleaning, clinician reattaches snap cover (9918) in generally the reverse order of detaching snap cover (9918) as described above.

E. A Second Snap Cover for a Fifth Accessible Outer Sheath

FIGS. 47-51 illustrate an eighth exemplary surgical instrument (10010) including a shaft assembly (10011) with a fifth accessible outer sheath (10012). With respect to FIG. 47 and FIG. 48, accessible outer sheath (10012) radially surrounds at least a portion of waveguide (140) about the longitudinal axis and includes a sheath body (10016), a second snap cover (10018), and a sheath securement (10020). Aside from differences noted below, snap cover (10018) is similar to snap cover (9918) (see FIG. 46) discussed above for accessing inner portion (9922) of surgical instrument (10010).

Figure 48:
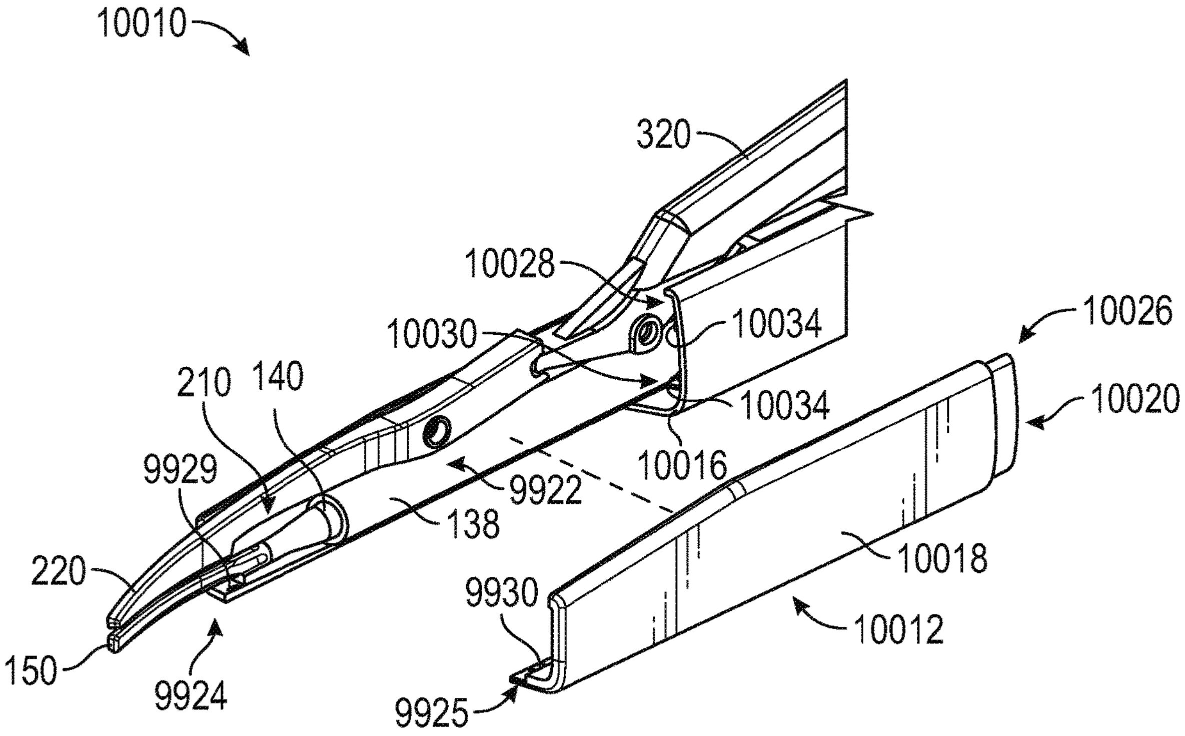
FIG. 48 depicts an enlarged partially exploded perspective view of the surgical instrument of FIG. 47.
Figure 49:
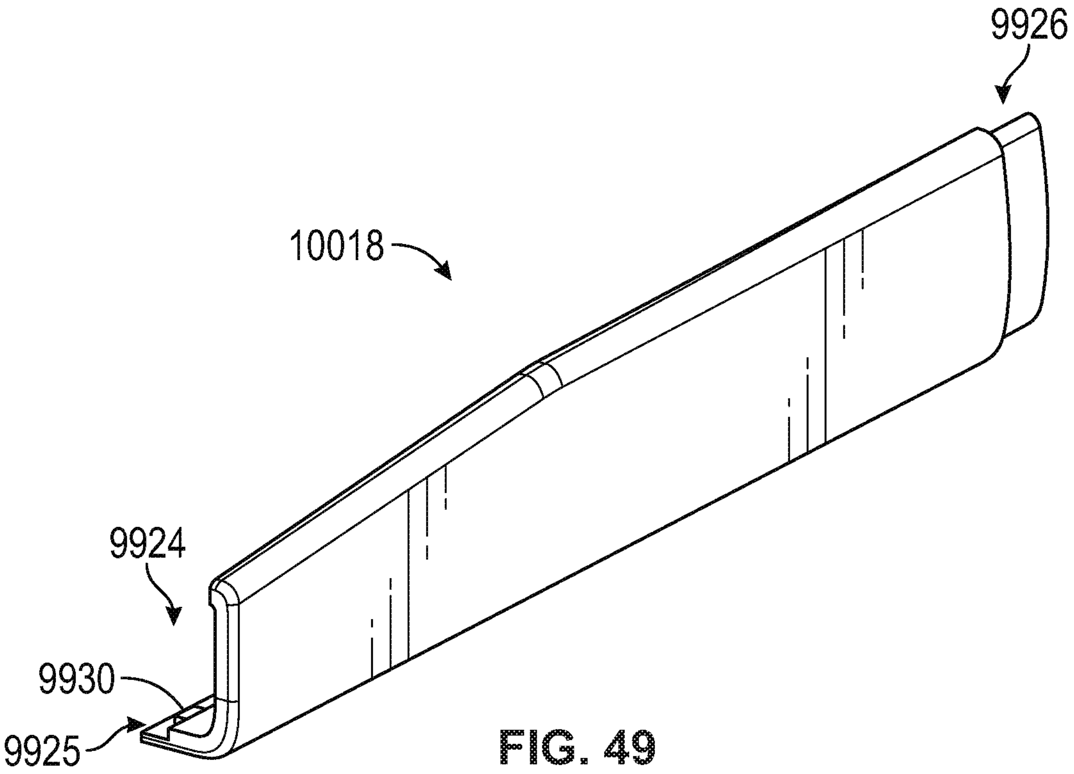
FIG. 49 depicts an exterior perspective view of the snap cover of FIG. 48.
Figure 50:
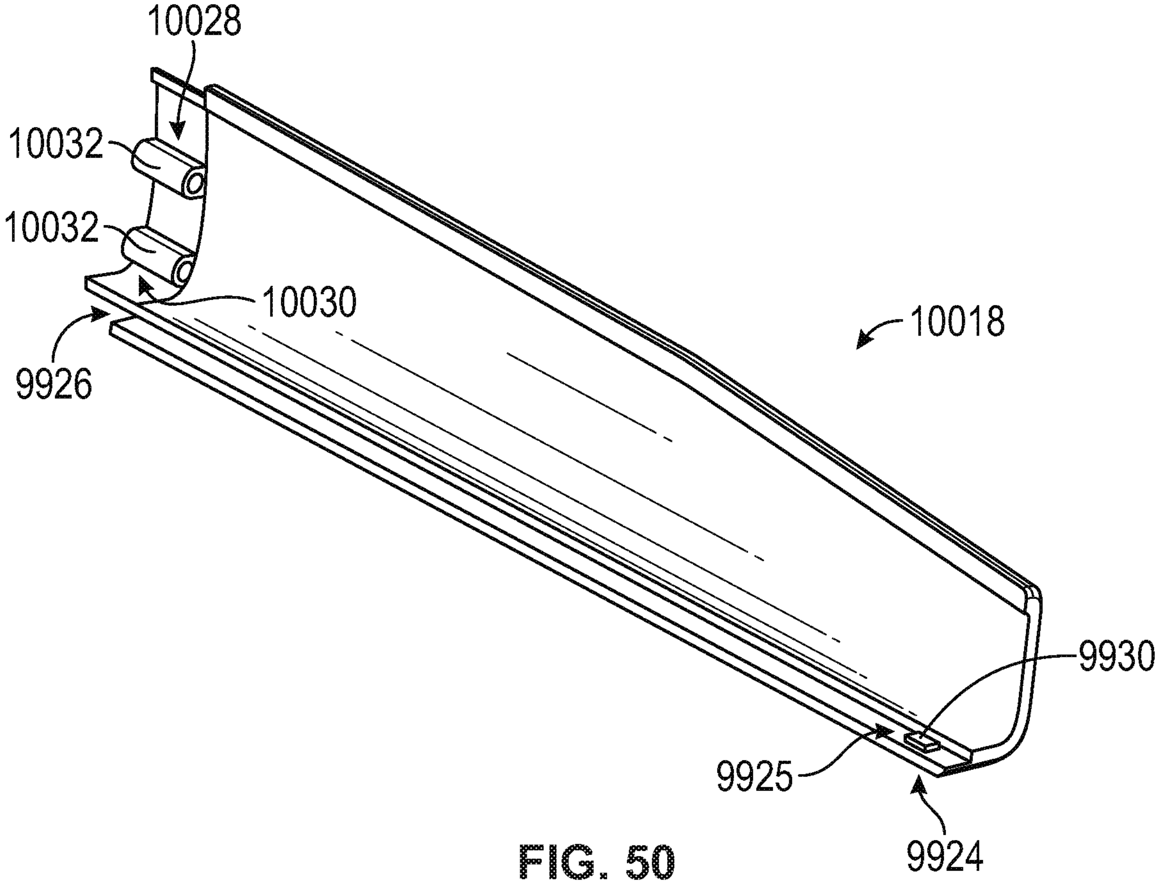
FIG. 50 depicts an interior perspective view of the snap cover of FIG. 48.

To this end, sheath securement (10020) includes distal securement (9924) discussed above, but has a proximal securement (10026) having an upper tubular coupling (10028) and a lower tubular coupling (10030). Each of upper and lower tubular coupling (10028, 10030) includes an outer tube (10032) longitudinally extending along an inner surface of snap cover (10018) and an inner tube (10034) longitudinally extending along an inner surface of sheath body (10016). As shown in FIGS. 48-50, outer tubes (10032) on snap cover (10018) are configured to respectively align with and slidably receive inner tubes (10034). Proximal securement (10026) thereby inhibits movement of snap cover (10018) relative to sheath body (10016), but for distal movement, which is inhibited by distal securement (9924).

Figure 51:
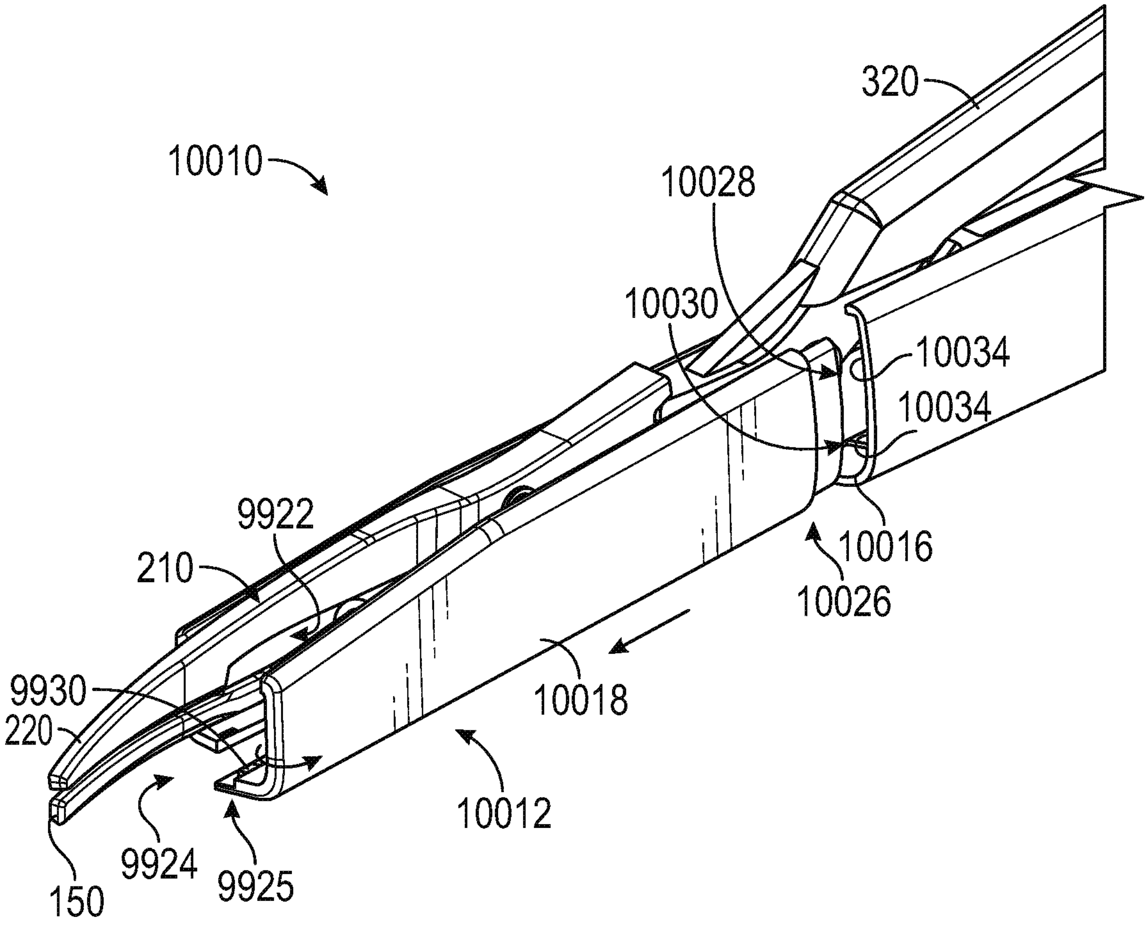
FIG. 51 depicts an enlarged perspective view of the surgical instrument of FIG. 47 with the snap cover being detached therefrom.

In use, with respect to FIG. 51, clinician accesses inner portion (9922) of surgical instrument (10010) by detaching snap cover (10018) from sheath body (10016). More particularly, clinician selectively pivots a distal portion of snap cover (10018) laterally outward to overcome the resilient engagement between resilient tab (9930) and shoulder (9929) of distal securement (9924). Once distal securement is disengaged, clinician distally withdraws snap cover (10018) to until inner tubes (10034) are removed from outer tubes (10032) for removal of snap cover (10018) and access to inner portion (9922). The clinician cleans surgical instrument (10010) using any one or more known cleaning methods for such instruments. Upon desirable cleaning, clinician reattaches snap cover (10018) in generally the reverse order of detaching snap cover (10018) as described above.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A device comprising: (a) an ultrasonic blade disposed in a tube; (b) a proximal form portion; and (c) a distal form portion.

Example 2

The device of Example 1, wherein the proximal form portion defines an internal channel.

Example 3

The device of example 1, wherein the proximal form portion includes a shutoff portion and a sleeve portion extending therefrom.

Example 4

A method of forming a seal between a tube and a waveguide, the method comprising: (a) extending a shutoff portion of a proximal form portion into a cavity defined between the tube and the waveguide; (b) coupling a distal form portion with the tube, wherein the waveguide extends through the distal form portion, wherein the proximal form portion, the distal form portion, and the tube define a mold space therebetween; (c) transferring a sealing material through the distal form portion and into the mold space; and (d) allowing the material in the mold space to cure and form a seal.

Example 5

A method of forming a seal between a tube and a waveguide, the method comprising: (a) constructing a form within a cavity defined between the tube and the waveguide, wherein the form defines a mold space; (b) transferring a sealing material through the form and into the mold space; and (c) allowing the material in the mold space to cure and form a seal between the tube and the waveguide.

Example 6

A surgical instrument, comprising: (a) a body assembly; (b) an ultrasonic waveguide extending through the body assembly along a longitudinal axis; (c) an ultrasonic blade connected to a distal end of the ultrasonic waveguide; (d) a clamp arm assembly configured to move from an opened position for receiving a tissue toward a closed position for clamping the tissue relative to the ultrasonic blade, wherein the clamp arm assembly includes: (i) a clamp body, and (ii) a clamp pad connected to the clamp body facing the ultrasonic blade; (e) a clamp arm actuator operatively connected to the clamp arm assembly and configured to selectively move from a first position toward a second position relative to the body to thereby respectively direct the clamp arm assembly from the opened position toward the closed position; and (f) an outer sheath radially surrounding at least a portion of the ultrasonic waveguide about the longitudinal axis, wherein the outer sheath includes: (i) a sheath body operatively connected to the body assembly and affixed relative to the ultrasonic waveguide, (ii) a cover removably received against the sheath body, and (iii) a sheath securement feature configured to detachably couple the cover to the sheath body such that the cover is configured to be selectively detached from the sheath body for accessing the ultrasonic waveguide within the outer sheath.

Example 7

The surgical instrument of Example 6, wherein the outer sheath is generally U-shaped.

Example 8

The surgical instrument of any of Example 6 through Example 7, wherein the outer sheath further includes a distal tissue stop configured to inhibit tissue from being proximally introduced beyond the distal tissue stop.

Example 9

The surgical instrument of Example 8, wherein the distal tissue stop has a first stop portion and a second stop portion, and wherein the first and second stop portions of the distal tissue stop are respectively positioned on the sheath body and the cover.

Example 10

The surgical instrument of any of Example 6 through Example 9, wherein the sheath securement feature includes a hinge coupling such that the cover is pivotable relative to the sheath body.

Example 11

The surgical instrument of Example 10, wherein the hinge coupling includes a pin extending from the cover or the sheath body and a bore extending through the other of the cover or the sheath body, wherein the bore is configured to rotatably receive the pin therein.

Example 12

The surgical instrument of Example 11, wherein the hinge coupling further includes a slot in communication with the bore, wherein the pin is configured to be removed from the bore through the slot to thereby decouple the cover from the sheath body.

Example 13

The surgical instrument of any of Example 6 through Example 12, wherein the sheath securement feature includes a snap coupling having a resilient tab configured to releasably engage a shoulder.

Example 14

The surgical instrument of any of Example 6 through Example 13, wherein the sheath securement feature includes a protrusion and channel, wherein the channel is configured to slidably receive the protrusion.

Example 15

The surgical instrument of any of Example 6 through Example 14, wherein the sheath securement feature includes a magnetic coupler configured to magnetically couple the cover relative to the sheath body.

Example 16

The surgical instrument of Example 15, wherein the magnetic coupler is configured to magnetically couple to at least one of the clamp arm assembly, the clamp arm actuator, or a tube about the ultrasonic waveguide.

Example 17

The surgical instrument of any of Example 6 through Example 16, wherein the sheath securement feature includes a pin hole and a pin, wherein the pin hole is configured to removably receive the pin.

Example 18

The surgical instrument of Example 17, wherein the pin is configured to have a friction fit within the pin hole.

Example 19

The surgical instrument of any of Example 6 through Example 18, wherein the sheath securement feature has a proximal securement portion and a distal securement portion, and wherein each of the proximal and distal securement portions are configured to detachably couple the cover to the sheath body.

Example 20

The surgical instrument of any of Example 6 through Example 19, further comprising a seal radially interposed between the ultrasonic waveguide and the outer sheath, wherein the seal is configured to prevent proximal fluid communication through a cylindraceous gap defined between the ultrasonic waveguide and the outer sheath.

Example 21

A method of accessing an inner portion of an ultrasonic instrument, wherein the ultrasonic instrument includes (a) a body assembly; (b) an ultrasonic waveguide extending through the body assembly along a longitudinal axis; (c) an ultrasonic blade connected to a distal end of the ultrasonic waveguide; (d) a clamp arm assembly configured to move from an opened position for receiving a tissue toward a closed position for clamping the tissue relative to the ultrasonic blade, wherein the clamp arm assembly includes: (i) a clamp body, and (ii) a clamp pad connected to the clamp body facing the ultrasonic blade; (e) a clamp arm actuator operatively connected to the clamp arm assembly and configured to selectively move from a first position toward a second position relative to the body to thereby respectively direct the clamp arm assembly from the opened position toward the closed position; and (f) an outer sheath radially surrounding at least a portion of the ultrasonic waveguide about the longitudinal axis, wherein the outer sheath includes: (i) a sheath body operatively connected to the body assembly and affixed relative to the ultrasonic waveguide, (ii) a cover removably received against the sheath body, and (iii) a sheath securement feature configured to detachably couple the cover to the sheath body such that the cover is configured to be selectively detached from the sheath body for accessing the ultrasonic waveguide within the outer sheath, the method comprising: (a) decoupling the cover from the sheath body to thereby reveal an inner portion of the ultrasonic instrument through an access space; and (b) accessing the inner portion of the ultrasonic instrument through the access space.

Example 22

The method of Example 21, further comprising cleaning the inner portion of the ultrasonic instrument while accessing the inner portion through the access space.

Example 23

The method of any of Example 21 through Example 22, wherein the act of decoupling further comprises pivoting the cover relative to the sheath body.

Example 24

The method of any of Example 21 through Example 23, wherein the act of decoupling further comprises sliding the cover relative to the sheath body.

Example 25

The method of any of Example 21 through Example 24, wherein the act of decoupling further comprises deflecting the cover relative to the sheath body.

Example 26

The method of Example 25, wherein deflecting the cover further includes deflecting one portion of the cover relative to another portion of the cover.

Example 27

A device comprising: (a) a tube; (b) an ultrasonic waveguide disposed in the tube; (c) an ultrasonic blade extending distally from the ultrasonic waveguide; (d) a proximal form portion, wherein the proximal form portion includes: (i) a shutoff portion, and (ii) a sleeve portion extending from the shutoff portion; and (e) a distal form portion, wherein the proximal form portion, the distal form portion, and the tube together define a mold space therebetween, wherein the mold space is configured to receive a sealing material through the distal form portion that forms a seal between the tube and the ultrasonic waveguide.

VI. Miscellaneous

While various examples herein describe two or more modular components being releasably coupled together, it should be understood that some variations may eliminate such modularity and releasable couplings. For instance, some versions of instrument (10) may provide first modular assembly (100) and second modular assembly (200) as a single combined unit that does not permit second modular assembly (200) to be removed form first modular assembly (100). In some such versions, coupling member (300) would either me omitted (with some other feature being used to provide permanent coupling between first modular assembly (100) and second modular assembly (200)); or coupling member (300) may be modified such that coupling member (300) may not be manipulated to decouple second modular assembly (200) from first modular assembly (100). Similarly, some versions of instrument (301) may prevent clamp arm assembly (400) from being removed from shaft assembly (330). For instance, latch member (412) may be omitted and clamp arm assembly (400) may be permanently coupled with shaft assembly (330).

It should be understood that the various teachings herein may be readily combined with the various teachings of U.S. Pub. No. 2017/0105754, entitled "Surgical Instrument with Dual Mode End Effector and Side-Loaded Clamp Arm Assembly," published on Apr. 20, 2017, the disclosure of which is incorporated by reference herein. Various suitable ways in which the teachings herein may be combined with the teachings of U.S. Pub. No. 2017/0105754 will be apparent to those of ordinary skill in the art.

It should be understood that the various teachings herein may be readily combined with the various teachings of U.S. Pub. No. 2017/0105755, entitled "Surgical Instrument with Dual Mode End Effector and Compound Lever with Detents," published on Apr. 20, 2017, the disclosure of which is incorporated by reference herein. Various suitable ways in which the teachings herein may be combined with the teachings of U.S. Pub. No. 2017/0105755 will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," published on Apr. 20, 2017, the disclosure of which is incorporated by reference herein. Various suitable ways in which the teachings herein may be combined with the teachings of U.S. Pub. No. 2017/0105788 will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/798,680, entitled "Surgical Instrument with Removable Clamp Arm Assembly," filed on Oct. 31, 2017, published as U.S. Pub. No. 2018/0132883 on May 17, 2018, the disclosure of which is incorporated by reference herein. Various suitable ways in which the teachings herein may be combined with the teachings of U.S. patent application Ser. No. 15/798,680, published as U.S. Pub. No. 2018/0132883 on May 17, 2018, will be apparent to those of ordinary skill in the art in view of the teachings herein.

In addition to the foregoing, the teachings herein may be readily combined with the teachings of U.S. patent application Ser. No. 15/798,703, entitled "Surgical Instrument with Removable End Effector Components," filed on Oct. 31, 2017, published as U.S. Pub. No. 2018/0132887 on May 17, 2018, the disclosure of which is incorporated by reference herein. Various suitable ways in which the teachings herein may be combined with the teachings of U.S. patent application Ser. No. 15/798,703, published as U.S. Pub. No. 2018/0132887 on May 17, 2018, will be apparent to those of ordinary skill in the art in view of the teachings herein.

In addition to the foregoing, the teachings herein may be readily combined with the teachings of U.S. patent application Ser. No. 15/798,720, entitled "Surgical Instrument with Selectively Actuated Gap-Setting Features for End Effector, " filed on Oct. 31, 2017, published as U.S. Pub. No. 2018/0132888 on May 17, 2018, the disclosure of which is incorporated by reference herein. Various suitable ways in which the teachings herein may be combined with the teachings of U.S. patent application Ser. No. 15/798,720, published as U.S. Pub. No. 2018/0132888 on May 17, 2018, will be apparent to those of ordinary skill in the art in view of the teachings herein.

In addition to the foregoing, the teachings herein may be readily combined with the teachings of U.S. patent application Ser. No. 15/798,835, entitled "Surgical Instrument with Spot Coagulation Control Algorithm," filed on Oct. 31, 2017, published as U.S. Pub. No. 2018/0132926 on May 17, 2018, the disclosure of which is incorporated by reference herein. Various suitable ways in which the teachings herein may be combined with the teachings of U.S. patent application Ser. No. 15/798,835, published as U.S. Pub. No. 2018/0132926 on May 17, 2018, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) a body assembly;

(b) an ultrasonic waveguide extending through the body assembly along a longitudinal axis;

(c) an ultrasonic blade connected to a distal end of the ultrasonic waveguide;

(d) a clamp arm assembly configured to move from an opened position for receiving a tissue toward a closed position for clamping the tissue relative to the ultrasonic blade, wherein the clamp arm assembly includes:

(i) a clamp body, and (ii) a clamp pad connected to the clamp body facing the ultrasonic blade;

(e) a clamp arm actuator operatively connected to the clamp arm assembly and configured to selectively move from a first position toward a second position relative to the body to thereby respectively direct the clamp arm assembly from the opened position toward the closed position; and (f) an outer sheath radially surrounding at least a portion of the ultrasonic waveguide about the longitudinal axis, wherein the outer sheath includes:

(i) a sheath body operatively connected to the body assembly and affixed relative to the ultrasonic waveguide, wherein the sheath body includes a pathway that receives the ultrasonic waveguide and at least a portion of the clamp arm assembly, (ii) a cover removably received against the sheath body, and (iii) a sheath securement feature configured to detachably couple the cover to the sheath body such that the cover is configured to be selectively detached from the sheath body for accessing the ultrasonic waveguide within the outer sheath.

2. The surgical instrument of claim 1, wherein the outer sheath is generally U-shaped.

3. The surgical instrument of claim 1, wherein the outer sheath further includes a distal tissue stop configured to inhibit tissue from being proximally introduced beyond the distal tissue stop.

4. The surgical instrument of claim 3, wherein the distal tissue stop has a first stop portion and a second stop portion, and wherein the first and second stop portions of the distal tissue stop are respectively positioned on the sheath body and the cover.

5. The surgical instrument of claim 1, wherein the sheath securement feature includes a hinge coupling such that the cover is pivotable relative to the sheath body.

6. The surgical instrument of claim 5, wherein the hinge coupling includes a pin extending from the cover or the sheath body and a bore extending through the other of the cover or the sheath body, wherein the bore is configured to rotatably receive the pin therein.

7. The surgical instrument of claim 6, wherein the hinge coupling further includes a slot in communication with the bore, wherein the pin is configured to be removed from the bore through the slot to thereby decouple the cover from the sheath body.

8. The surgical instrument of claim 1, wherein the sheath securement feature includes a snap coupling having a resilient tab configured to releasably engage a shoulder.

9. The surgical instrument of claim 1, wherein the sheath securement feature includes a protrusion and channel, wherein the channel is configured to slidably receive the protrusion.

10. The surgical instrument of claim 1, wherein the sheath securement feature includes a magnetic coupler configured to magnetically couple the cover relative to the sheath body.

11. The surgical instrument of claim 10, wherein the magnetic coupler is configured to magnetically couple to at least one of the clamp arm assembly, the clamp arm actuator, or a tube about the ultrasonic waveguide.

12. The surgical instrument of claim 1, wherein the sheath securement feature includes a pin hole and a pin, wherein the pin hole is configured to removably receive the pin.

13. The surgical instrument of claim 12, wherein the pin is configured to have a friction fit within the pin hole.

14. The surgical instrument of claim 1, wherein the sheath securement feature has a proximal securement portion and a distal securement portion, and wherein each of the proximal and distal securement portions are configured to detachably couple the cover to the sheath body.

15. The surgical instrument of claim 1, further comprising a seal radially interposed between the ultrasonic waveguide and the outer sheath, wherein the seal is configured to prevent proximal fluid communication through a cylindraceous gap defined between the ultrasonic waveguide and the outer sheath.

16. A method of accessing an inner portion of an ultrasonic instrument, wherein the ultrasonic instrument includes:

(a) a body assembly;

(b) an ultrasonic waveguide extending through the body assembly along a longitudinal axis;

(c) an ultrasonic blade connected to a distal end of the ultrasonic waveguide;

(d) a clamp arm assembly configured to move from an opened position for receiving a tissue toward a closed position for clamping the tissue relative to the ultrasonic blade, wherein the clamp arm assembly includes:

(i) a clamp body, and (ii) a clamp pad connected to the clamp body facing the ultrasonic blade;

(e) a clamp arm actuator operatively connected to the clamp arm assembly and configured to selectively move from a first position toward a second position relative to the body to thereby respectively direct the clamp arm assembly from the opened position toward the closed position; and (f) an outer sheath radially surrounding at least a portion of the ultrasonic waveguide about the longitudinal axis, wherein the outer sheath includes:

(i) a sheath body operatively connected to the body assembly and affixed relative to the ultrasonic waveguide, (ii) a cover removably received against the sheath body, and (iii) a sheath securement feature configured to detachably couple the cover to the sheath body such that the cover is configured to be selectively detached from the sheath body for accessing the ultrasonic waveguide within the outer sheath, the method comprising:

(a) decoupling the cover from the sheath body to thereby reveal an inner portion of the ultrasonic instrument through an access space, wherein the act of decoupling further comprises pivoting the cover relative to the sheath body; and (b) accessing the inner portion of the ultrasonic instrument through the access space.

17. The method of claim 16, further comprising cleaning the inner portion of the ultrasonic instrument while accessing the inner portion through the access space.

18. The method of claim 16, wherein the act of decoupling further comprises sliding the cover relative to the sheath body.

19. A surgical instrument, comprising:

(a) a body assembly;

(b) an ultrasonic waveguide extending through the body assembly along a longitudinal axis;

(c) an ultrasonic blade connected to a distal end of the ultrasonic waveguide;

(d) a clamp arm assembly configured to move from an opened position for receiving a tissue toward a closed position for clamping the tissue relative to the ultrasonic blade, wherein the clamp arm assembly includes:

(i) a clamp body, and (ii) a clamp pad connected to the clamp body facing the ultrasonic blade;

(e) a clamp arm actuator operatively connected to the clamp arm assembly and configured to selectively move from a first position toward a second position relative to the body to thereby respectively direct the clamp arm assembly from the opened position toward the closed position; and (f) an outer sheath radially surrounding at least a portion of the ultrasonic waveguide about the longitudinal axis, wherein the outer sheath includes:

(i) a sheath body operatively connected to the body assembly and affixed relative to the ultrasonic waveguide, (ii) a cover removably received against the sheath body, and (iii) a sheath securement feature configured to detachably couple the cover to the sheath body such that the cover is configured to be selectively detached from the sheath body for accessing the ultrasonic waveguide within the outer sheath, wherein the sheath securement feature includes a hinge coupling such that the cover is pivotable relative to the sheath body.

20. The surgical instrument of claim 19, wherein the hinge coupling includes a pin extending from the cover or the sheath body and a bore extending through the other of the cover or the sheath body, wherein the bore is configured to rotatably receive the pin therein.

21. The surgical instrument of claim 20, wherein the hinge coupling further includes a slot in communication with the bore, wherein the pin is configured to be removed from the bore through the slot to thereby decouple the cover from the sheath body.

* * * * *